(12) United States Patent
Engelhardt et al.

(10) Patent No.: US 9,296,748 B2
(45) Date of Patent: Mar. 29, 2016

(54) PYRIDINONES

(71) Applicant: Boehringer Ingelheim International GmbH, Ingelheim am Rhein (DE)

(72) Inventors: Harald Engelhardt, Ebreichsdorf (AT); Laetitia Martin, Vienna (AT); Christian Smethurst, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/714,521

(22) Filed: May 18, 2015

(65) Prior Publication Data

US 2015/0246919 A1    Sep. 3, 2015

Related U.S. Application Data

(63) Continuation of application No. 14/456,038, filed on Aug. 11, 2014, now abandoned.

(30) Foreign Application Priority Data

Aug. 14, 2013  (EP) ..................................... 13180404

(51) Int. Cl.
    C07D 401/04    (2006.01)
    C07D 401/14    (2006.01)
    C07D 471/04    (2006.01)
    C07D 487/04    (2006.01)
    C07D 403/04    (2006.01)
    C07D 403/14    (2006.01)
    C07D 405/14    (2006.01)
    C07D 413/14    (2006.01)
    C07D 473/32    (2006.01)

(52) U.S. Cl.
    CPC ............ *C07D 471/04* (2013.01); *C07D 401/04* (2013.01); *C07D 401/14* (2013.01); *C07D 403/04* (2013.01); *C07D 403/14* (2013.01); *C07D 405/14* (2013.01); *C07D 413/14* (2013.01); *C07D 473/32* (2013.01)

(58) Field of Classification Search
    USPC ....................................................... 546/273.4
    See application file for complete search history.

(56) References Cited

FOREIGN PATENT DOCUMENTS

| EP | 2439197 A1 |   | 4/2012 |
|----|------------|---|--------|
| EP | 2439197 A1 | * | 4/2012 |
| WO | 2005085231 A1 |  | 9/2005 |
| WO | 2007104053 A2 |  | 9/2007 |
| WO | 2008043019 A1 |  | 4/2008 |
| WO | 2010107739 A2 |  | 9/2010 |

OTHER PUBLICATIONS

Database Registry; Accession No. 1375204-72-0, XP002719777, Jun. 5, 2012.
Database Registry; Accession No. 860784-66-3, XP002719778, Aug. 18, 2005.
Database Registry; Accession No. 400077-28-3, XP002719779, Mar. 11, 2002.
Database Registry; Accession No. 400077-27-2, XP002719780, Mar. 11, 2002.
Database Registry; Accession No. 400077-26-1, XP002719781, Mar. 11, 2002.
Database Registry; Accession No. 400077-24-9, XP002719782, Mar. 11, 2002.
Database Registry; Accession No. 400075-96-9, XP002719783, Mar. 11, 2002.
Database Registry; Accession No. 338774-04-2, XP002719784, May 29, 2001.
Database Registry; Accession No. 338774-03-1, XP002719785, May 29, 2001.
Database Registry; Accession No. 338774-00-8, XP002719786, May 29, 2001.
Database Registry; Accession No. 338773-97-0, XP002719787, May 29, 2001.
Hay et al., The design and 1-21 synthesis of 5- and 6-isoxazolylbenzimidazoles as selective inhibitors of the BET bromodomains, Med Chem Comm. vol. 4, No. 1, 2013, p. 140.
International Search Report, form PCT/ISA 210, and Written Opinion, PCT/ISA/237, for corresponding application PCT/EP2014/067263, date of mailing Nov. 28, 2014.

* cited by examiner

*Primary Examiner* — Laura L Stockton
(74) *Attorney, Agent, or Firm* — Michael P. Morris; Alan R. Stempel

(57) ABSTRACT

The present invention encompasses compounds of general formula (I)

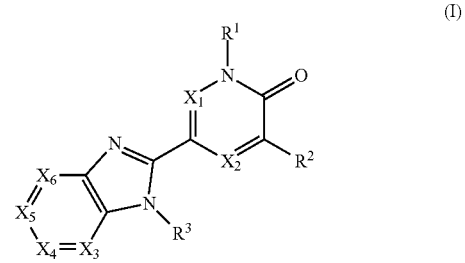

wherein the groups $R^1$ to $R^3$ and $X_1$ through $X_6$ have the meanings given in the claims and in the specification. The compounds of the invention are suitable for the treatment of diseases characterized by excessive or abnormal cell proliferation pharmaceutical preparations containing such compounds and their uses as a medicament.

18 Claims, No Drawings

PYRIDINONES

This invention relates to compounds of the general formula (I)

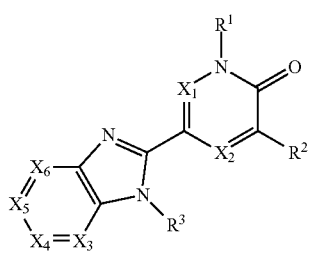

wherein the groups $R^1$ to $R^3$ and $X_1$ through $X_6$ have the meanings given below in this specification. The compounds of the invention are suitable for the treatment of diseases characterized by excessive or abnormal cell proliferation, pharmaceutical preparations containing such compounds and their uses as a medicament. The compounds of the invention are BRD4 inhibitors.

BACKGROUND OF THE INVENTION

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction. Recent research has established a compelling rationale for targeting BRD4 in cancer. BRD4 remains bound to transcriptional start sites of genes expressed during the entry into the G1 phase of the cell cycle, and is functioning to recruit the positive transcription elongation factor complex (P-TEFb), resulting in increased expression of growth promoting genes (Yang and Zhou, Mol. Cell. Biol. 28, 967, 2008). Importantly, BRD4 has been identified as a component of a recurrent t(15;19) chromosomal translocation in an aggressive form of human squamous carcinoma (French et al., Cancer Res. 63, 304, 2003). Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the proliferation and the differentiation block of these malignant cells. In addition, BRD4 has been identified as a critical sensitivity determinant in a genetically defined A ML mouse model (Zuber et al., Nature 2011 478(7370):524-8). Suppression of BRD4 led to robust anti-leukemic effects in vitro and in vivo, accompanied by terminal myeloid differentiation. Interestingly, BRD4 inhibition triggered MYC down-regulation in a broad array of mouse and human leukemia cell lines examined, indicating that small molecule BRD4 inhibitors may provide a means to suppress the MYC pathway in a range of A ML subtypes.

Finally, the other family members of the BET family have also been reported to have some function in controlling or executing aspects of the cell cycle, and have been shown to remain in complex with chromosomes during cell division—suggesting a role in the maintenance of epigenetic memory (Leroy et ai, Mol. Cell. 2008 30(1):51-60).

Examples of bromodomain inhibitors are benzodiazepine derivatives, disclosed in WO2011/054553, and imidazo[4,5] quinoline derivatives, disclosed in WO2011/054846.

Thus, there is the need to provide BRD4 inhibitors useful for the prevention and/or treatment of diseases characterized by excessive or abnormal cell proliferation, such as cancer.

DETAILED DESCRIPTION OF THE INVENTION

The present invention relates to compounds of formula (I)

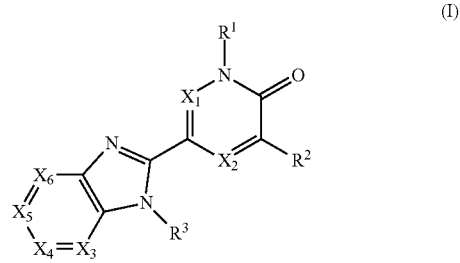

wherein,
$R^1$ is selected from —H or —$C_{1-3}$alkyl and $R^2$ is —$C_{1-3}$ alkyl; or
$R^1$ is —$C_{1-3}$alkyl and $R^2$ is selected from —H, —$C_{1-3}$alkyl, —$C_{1-3}$haloalkyl, —$NH_2$, —NH—$C_{1-3}$alkyl, halogen;
$R^3$ is —$C_{1-4}$alkyl substituted with one or more groups independently selected from halogen, —$C_{1-2}$haloalkyl, —O—$C_{1-3}$alkyl, —O—$C_{1-3}$halolkyl, 4-7 membered heterocycloalkyl, —$C_{3-7}$ cycloalkyl, phenyl and 5-6 membered heteroaryl, wherein the phenyl and the 5-6 membered heteroaryl groups can be optionally substituted with one or more groups independently selected from halogen and —$C_{1-2}$alkyl;
$X_1$ is —CH= or —N=
$X_2$ is —$CR^7$= or —N=,
wherein $X_1$ is —CH= and $X_2$ is —N=, or $X_1$ is —N= and $X_2$ is —CH=, or $X_1$ is —CH= and $X_2$ is —$CR^7$=
$X_3$ is —$CR^8$= or —N=;
$X_4$ is —$CR^4$= or —N=;
$X_5$ is —$CR^5$= or —N=;
$X_6$ is —CH= or —N=;
with the proviso that none or only one or two among $X_3$, $X_4$, $X_5$ and $X_6$ are —N=;
$R^4$ is selected from —H, halogen, —CN, —$NH_2$, —O—$R^6$, —N($C_{1-3}$alkyl)$_2$, —C(O)N($C_{1-3}$alkyl)$_2$ and —$C_{1-5}$alkyl, wherein the —$C_{1-5}$alkyl group can be optionally and independently substituted with one or more groups independently selected from halogen or —CN, or
$R^4$ is selected from 5-6 membered heteroaryl and 4-7 membered heterocycloalkyl, wherein the heteroaryl groups can be optionally and independently substituted with one or more groups independently selected from —C$_{1-3}$alkyl, and the heterocycloalkyl group can be optionally and independently substituted with one or more groups independently selected from —C$_{1-3}$alkyl or =O, or R$^4$ is a —C$_{3-6}$cycloalkyl wherein the cycloalkyl group can be optionally and independently substituted with one or more groups independently selected from C$_{1-3}$alkyl, —C$_{1-3}$haloalkyl and halogen;

R$^5$ is selected from —H, halogen, —NH$_2$, —C$_{1-3}$alkyl, —SO$_2$N(C$_{1-3}$alkyl)$_2$ and 5-6 membered heterocycloalkyl, which heterocycloalkyl can be optionally substituted with one or more groups independently selected from =O, —C$_{1-3}$alkyl, and —C$_{1-5}$haloalkyl;

R$^6$ is selected from 4-7 membered heterocycloalkyl, —C$_{3-7}$ cycloalkyl and —C$_{1-5}$alkyl, wherein the —C$_{1-5}$ alkyl group can be optionally substituted with —C$_{3-7}$ cycloalkyl, R$^7$ is selected from —H, —C$_{1-5}$alkyl and —O—C$_{1-5}$alkyl;

R$^8$ is —H or —C$_{1-3}$alkyl;

wherein the compounds of formula (I) may be optionally be present in the form of salts.

In a preferred embodiment, the invention relates to compounds of formula (Ia) to (If) selected from

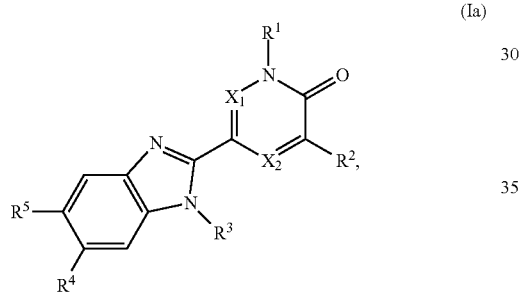
(Ia)

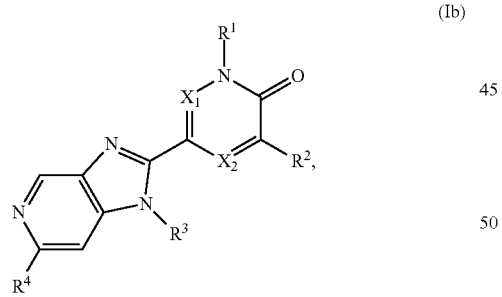
(Ib)

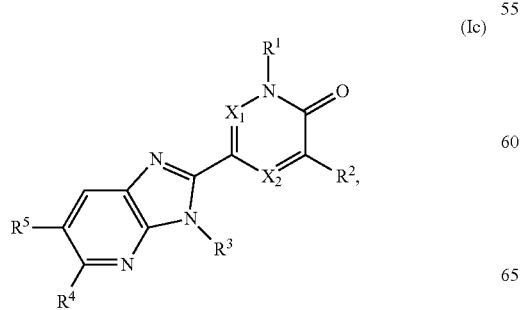
(Ic)

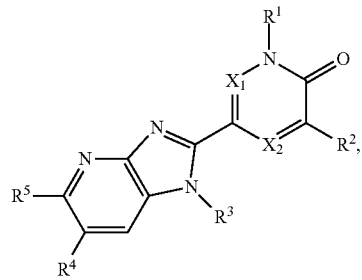
(Id)

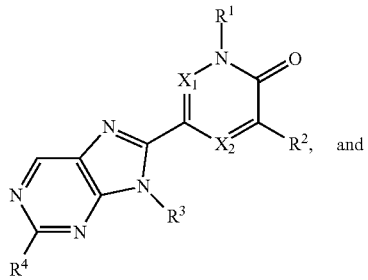
(Ie)

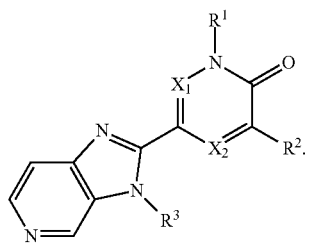
(If)

wherein R$^1$ to R$^5$, X$_1$ and X$_2$ have the meanings given herein above and below.

In a preferred embodiment, the invention relates to compounds of formula

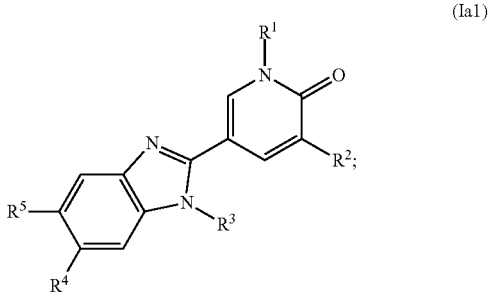
(Ia1)

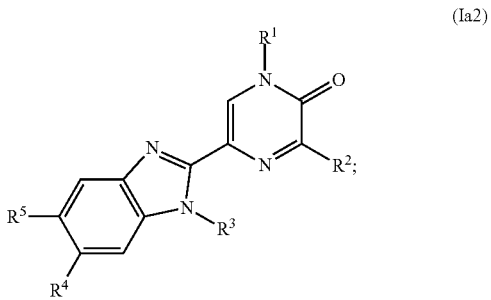
(Ia2)

-continued
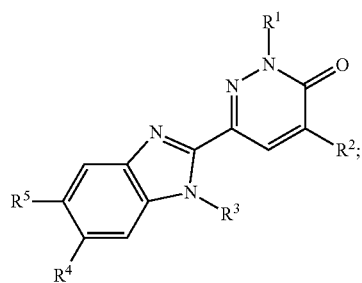
(Ia3)
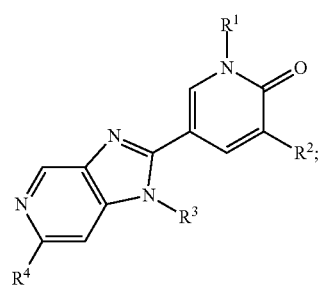
(Ib1)
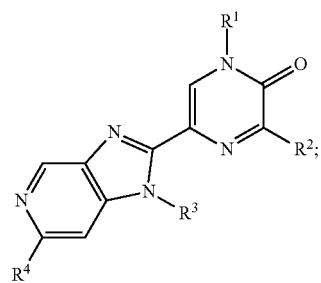
(Ib2)
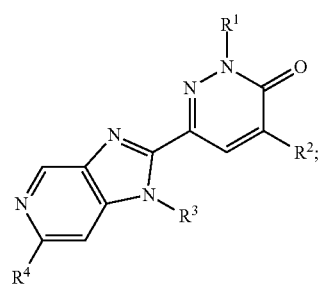
(Ib3)
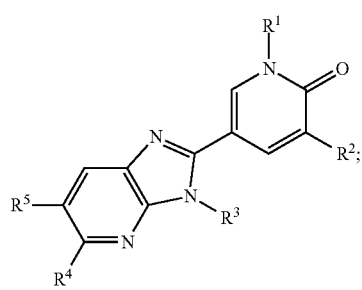
(Ic1)
-continued
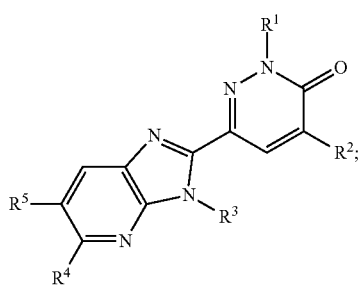
(Ic2)
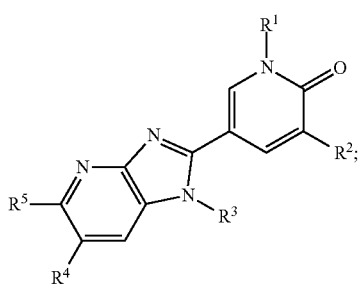
(Id1)
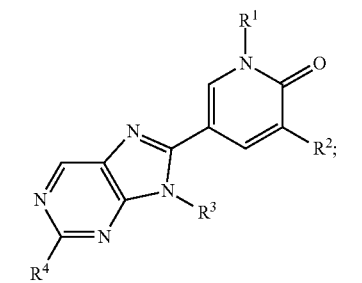
(Ie1)
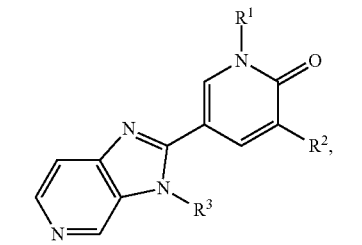
(If1)
wherein $R^1$ to $R^5$ have the meanings given herein above and below.
In a preferred embodiment, the invention relates to compounds of formula
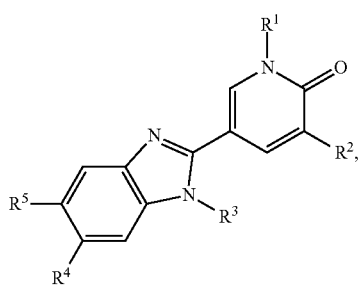
(Ia1)

(Ia2)
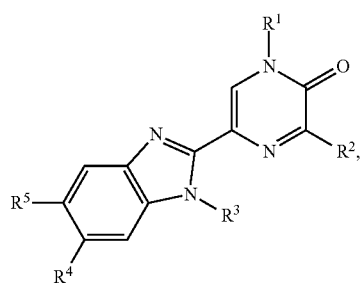
(Ia3)
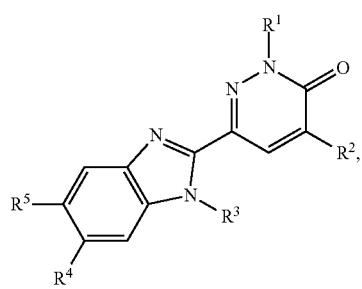
(Ib1)
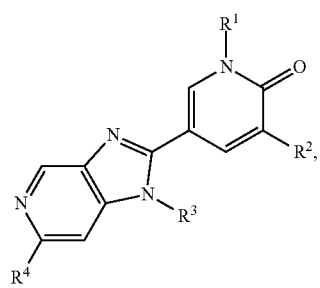
(Ib2)
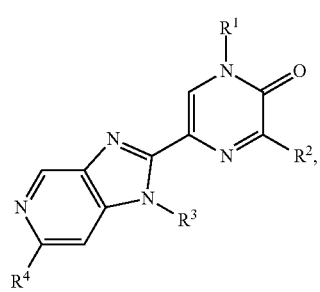
(Ib3)
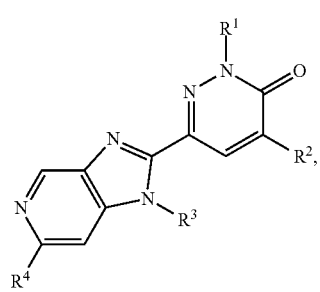
(Ic1)
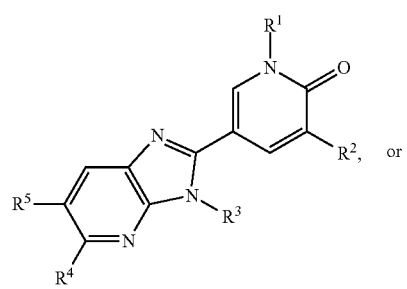
(Ie1)
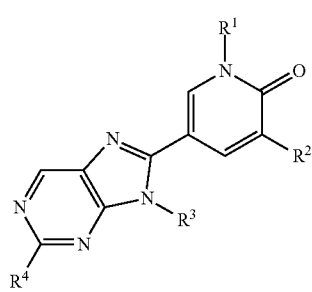
wherein $R^1$ to $R^5$ have the meanings given herein above and below.
In a preferred embodiment, the invention relates to compounds of formula
(I1)
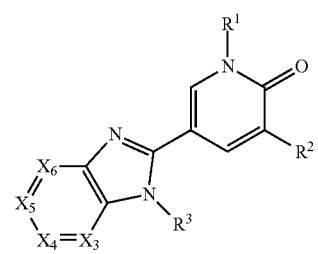
wherein $R^1$ to $R^3$ and $X_3$ to $X_6$ have the meanings given herein above and below.
In a preferred embodiment, the invention relates to compounds of formula
(Ia1)
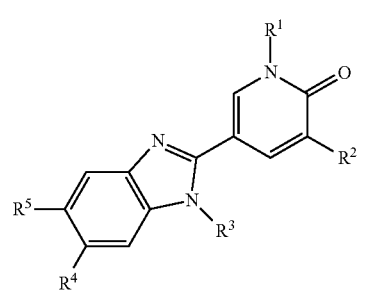 or

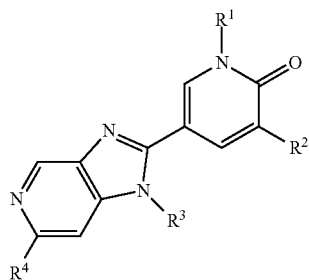
(Ib1)

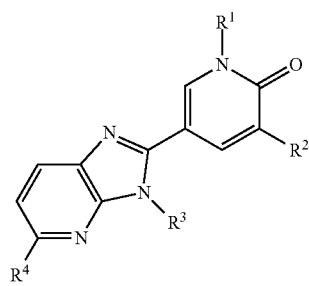
(Ic1)

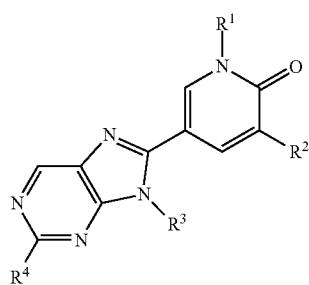
(Ie1)

wherein R¹ to R⁵ have the meanings given herein above and below.

In a preferred embodiment, the invention relates to compounds of formula (I), wherein $X_2$ is —CH= or —N=.

In a preferred embodiment, the invention relates to compounds of formula (I), wherein $X_3$ is —CH= or —N=.

In a preferred embodiment, the invention relates to compounds of formula (I), wherein $X_5$ is —N=.

In a preferred embodiment, the invention relates to compounds of formula (I), wherein $R^7$ is selected from —H, —CH₃, —O—CH₂CH₃. In a most preferred embodiment $R^7$ is —H.

In a preferred embodiment, the invention relates to compounds of formula (I), wherein $R^1$ is —C₁₋₃alkyl.

In a preferred embodiment, the invention relates to compounds of formula (I), wherein $R^1$ is —CH₃.

In a preferred embodiment, the invention relates to compounds of formula (I), wherein $R^2$ is selected from —H, —NH₂, —NH—C₁₋₃alkyl and —C₁₋₃alkyl.

In a preferred embodiment, the invention relates to compounds of formula (I), wherein $R^2$ is selected from —H, —NH₂, —NHCH₃ and —CH₃.

In a preferred embodiment, the invention relates to compounds of formula (I), wherein $R^2$ is —C₁₋₃alkyl.

In a preferred embodiment, the invention relates to compounds of formula (I), wherein $R^2$ is —CH₃.

In a preferred embodiment, the invention relates to compounds of formula (I), wherein $R^3$ is selected from —CH(CH₃)—CH₂—O—CH₃, —CH(CH₃)—CH₂-cyclopropyl, —CH₂-phenyl, —CH₂-pyridyl, —CH(CH₃)phenyl, —CH(CH₃)-pyridyl, wherein the phenyl and pyridyl groups are optionally and independently substituted with —Cl or with one or two —F.

In a preferred embodiment, the invention relates to compounds of formula (I), wherein $R^3$ is selected from —CH(CH₃)—CH₂—O—CH₃, —CH₂-phenyl, —CH₂-pyridyl, —CH(CH₃)phenyl, —CH(CH₃)-pyridyl, wherein the phenyl and pyridyl groups are optionally and independently substituted with —Cl.

In a preferred embodiment, the invention relates to compounds of formula (I), wherein $R^3$ is selected from —CH₂-phenyl or —CH₂-pyridyl, —CH(CH₃)phenyl and —CH(CH₃)-pyridyl.

In a preferred embodiment, the invention relates to compounds of formula (I), wherein $R^3$ is —CH₂-phenyl or —CH(CH₃)phenyl.

In a preferred embodiment, the invention relates to compounds of formula (I), wherein $R^4$ is selected from —H, halogen, —CN, —NH₂, —C₁₋₅alkyl, —N(C₁₋₃alkyl)₂, —C(O)N(C₁₋₃alkyl)₂, —O—C₁₋₅alkyl, —O—CH₂-cyclopropyl, —O-(6 membered heterocycloalkyl), —O-cyclopropyl, 5-6 membered heteroaryl and 4-7 membered heterocycloalkyl, wherein the heterocycloalkyl is optionally substituted with one or more groups independently selected from —C₁₋₃alkyl.

In a preferred embodiment, the invention relates to compounds of formula (I), wherein $R^4$ is selected from —H, halogen, —CN, —NH₂, —C₁₋₅alkyl, —N(C₁₋₃alkyl)₂, —C(O)N(C₁₋₃alkyl)₂, —O—C₁₋₅alkyl, —O—CH₂-cyclopropyl, 5-6 membered heteroaryl and 4-7 membered heterocycloalkyl, wherein the heterocycloalkyl is optionally substituted with one or more groups independently selected from —C₁₋₃alkyl.

In a preferred embodiment, the invention relates to compounds of formula (I), wherein $R^4$ is selected from —H, —F, —Cl, —CN, isopropyl, —NH₂, —N(CH₃)₂, —C(O)N(CH₃)₂, —O—CH₃, —O—CH(CH₃), —O—(CH₂)₂CH₃, —O-tetrahydrofuran, —O-piperidine, —O-cyclopropyl, —O—CH₂-cyclopropyl, imidazole, tetrahydropyran, cyclopropyl substituted with —CF₃, piperazine substituted with —CH₃ or =O, and morpholine optionally substituted with —CH₃ or

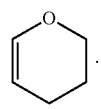

In a preferred embodiment, the invention relates to compounds of formula (I), wherein $R^4$ is selected from —H, —F, —Cl, —CN, isopropyl, —NH₂, —N(CH₃)₂, —C(O)N(CH₃)₂, —O—CH₃, —O—CH₂-cyclopropyl, imidazole, piperazine substituted with —CH₃, and morpholine optionally substituted with —CH₃.

In a preferred embodiment, the invention relates to compounds of formula (I), wherein $R^4$ is selected from —C₁₋₅alkyl or 4-7 membered heterocycloalkyl, which heterocycloalkyl can be optionally substituted with one or more groups independently selected from —C₁₋₃alkyl.

In a preferred embodiment, the invention relates to compounds of formula (I), wherein $R^4$ is 6 membered heterocycloalkyl, which heterocycloalkyl can be optionally substituted with one or more groups independently selected from —C₁₋₃alkyl.

In a preferred embodiment, the invention relates to compounds of formula (I), wherein $R^4$ is selected from isopropyl, piperazine substituted with —$CH_3$ and morpholine optionally substituted with —$CH_3$.

In a preferred embodiment, the invention relates to compounds of formula (I), wherein $R^4$ is selected from tetrahydropyran, piperazine substituted with —$CH_3$ and morpholine optionally substituted with —$CH_3$.

In a preferred embodiment, the invention relates to compounds of formula (I), wherein $R^5$ is selected from —H, —Cl, —$NH_2$, —$SO_2N(CH_3)$, piperazine optionally substituted with —$CH_3$, tetrahydropyran and

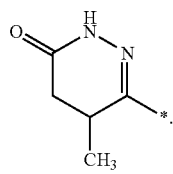

In a preferred embodiment, the invention relates to compounds of formula (I), wherein $R^5$ is selected from —H, —Cl,

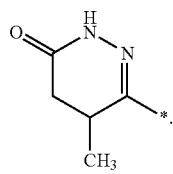

In a further embodiment, the invention relates to compounds of formula (I) for use in the treatment of cancer.

In a further embodiment, the invention relates to compound of general formula (I) according to anyone of the embodiments described herein in the description—or the pharmaceutically acceptable salts thereof—for use in the treatment and/or prevention of cancer.

In a further embodiment, the invention relates to pharmaceutical preparation comprising as active substance one or more compounds of general formula (I) according to anyone of the embodiments described herein in the description optionally in combination with conventional excipients and/or carriers.

In a further embodiment, the invention relates to pharmaceutical preparation comprising a compound of general formula (I) according to anyone of the embodiments described herein in the description—or one of the pharmaceutically acceptable salts thereof—and at least one other cytostatic or cytotoxic active substance, different from formula (I).

The present invention further relates to hydrates, solvates and polymorphs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to compounds of general formula (I)—or the pharmaceutically acceptable salts thereof—for use in the treatment and/or prevention of cancer.

In another aspect the invention relates to the use of the compounds of general formula (I)—or the pharmaceutically acceptable salts thereof—in the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of hematopoietic malignancies, preferably acute myeloid leukemia (AML), multiple myeloma (MM).

In another aspect the invention relates to compounds of general formula (I)—or the pharmaceutically acceptable salts thereof—for use in the treatment and/or prevention of solid tumors, preferably to lung, liver, colon, brain, thyroid, pancreas, breast, ovary and prostate cancer.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named sub-group is the radical attachment point, for example the substitutent —$C_{1-5}$alkyl-$C_{3-10}$cycloalkyl, means a $C_{3-10}$cycloalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy.

Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H$_2$N—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc. By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or H$_2$N—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x\text{-}y}$-alkynylamino or $C_{x\text{-}y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x\text{-}y}$-alkynyleneamino or $H_2N$—$C_{x\text{-}y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —Cl=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms.

Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc. The above definition for cycloalkyl also applies if cycloalkyl is part of another group as in $C_{x\text{-}y}$-cycloalkylamino or $C_{x\text{-}y}$-cycloalkyloxy, for example.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

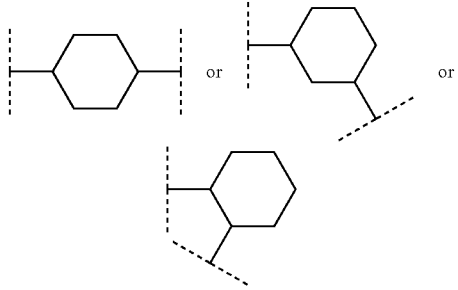

(cyclohexylene).

The above definition for cycloalkylene also applies if cycloalkylene is part of another group as in HO—$C_{x\text{-}y}$-cycloalkyleneamino or $H_2N$—$C_{x\text{-}y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x\text{-}y}$-cycloalkenylamino or $C_{x\text{-}y}$-cycloalkenyloxy, for example.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

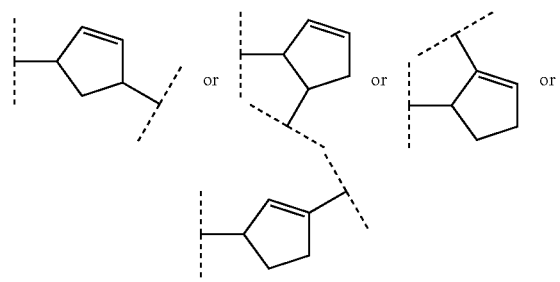

(cyclopentenylene) etc.

The above definition for cycloalkenylene also applies when cycloalkenylene is part of another group as in HO—$C_{x\text{-}y}$-cycloalkenyleneamino or $H_2N$—$C_{x\text{-}y}$-cycloalkenyleneoxy, for example.

Aryl denotes a mono-, bi- or tricyclic group with at least one aromatic carbocycle. Preferably it denotes a a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are e.g.

phenyl and

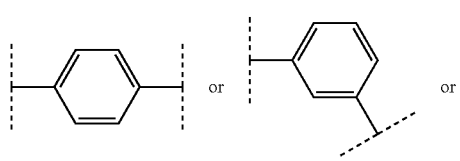

-continued

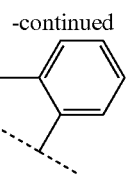

(o,m,p-phenylene), naphthyl and

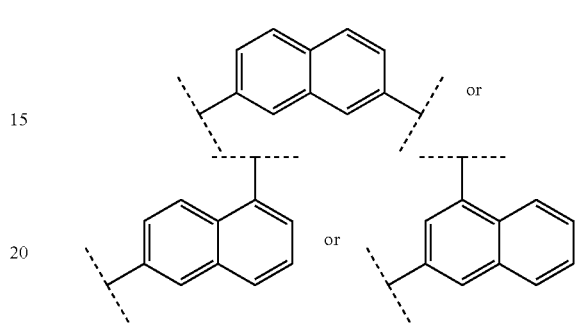

etc.

The above definition for arylene also applies when arylene is part of another group as in HO-aryleneamino or $H_2N$-aryleneoxy for example.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur sulphoxide→SO, sulphone —$SO_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S, S-dioxide, homothiomorpholinyl-S-oxide, 2,3-dihydroazet, 2H-pyrrolyl, 4H-pyranyl, 1,4-dihydro-pyridinyl, 8-azabicyclo[3.2.1]octyl, 8-azabicyclo[5.1.0]oc-tyl, 2-oxa-5-azabicyclo[2.2.1]-heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]-decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4.5]decyl etc.

Further examples are the structures illustrated below, which may be attached via each hydrogen-carrying atom (exchanged for hydrogen):

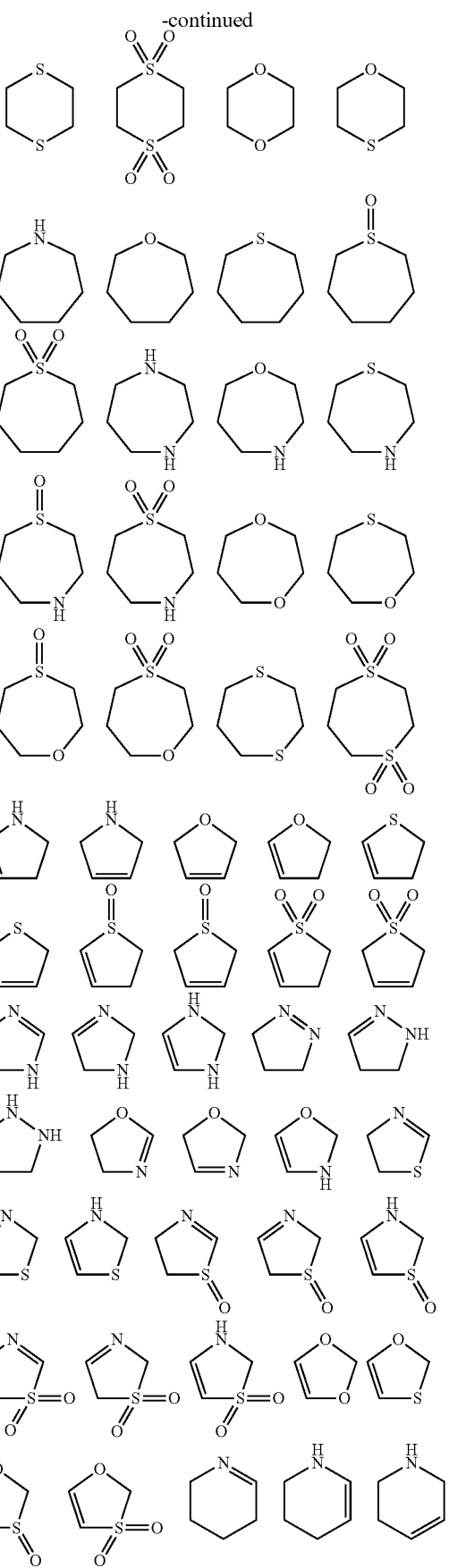

-continued

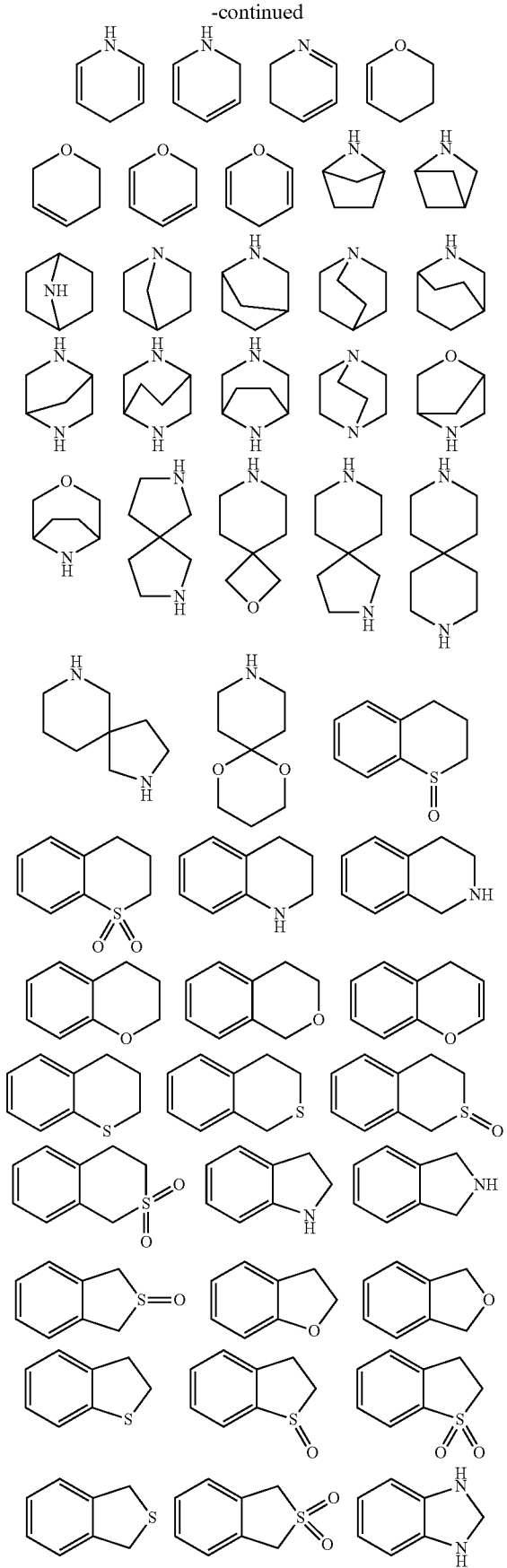

-continued

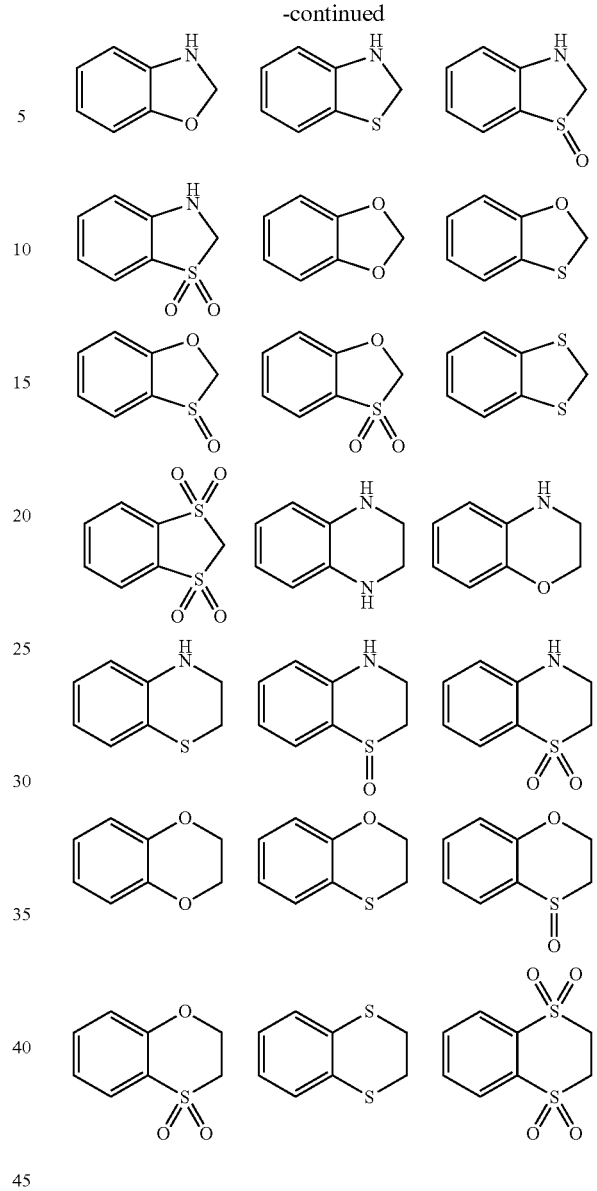

The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and

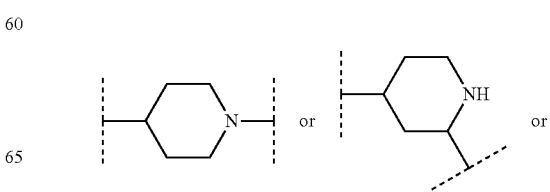

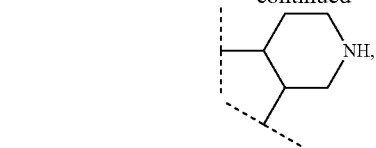

2,3-dihydro-1H-pyrrolyl and

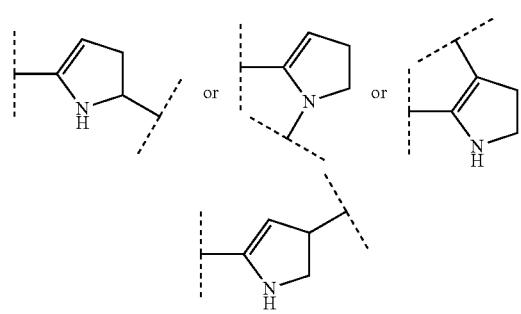

etc.

The above definition of heterocyclylene also applies if heterocyclylene is part of another group as in HO-heterocyclyleneamino or H₂N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

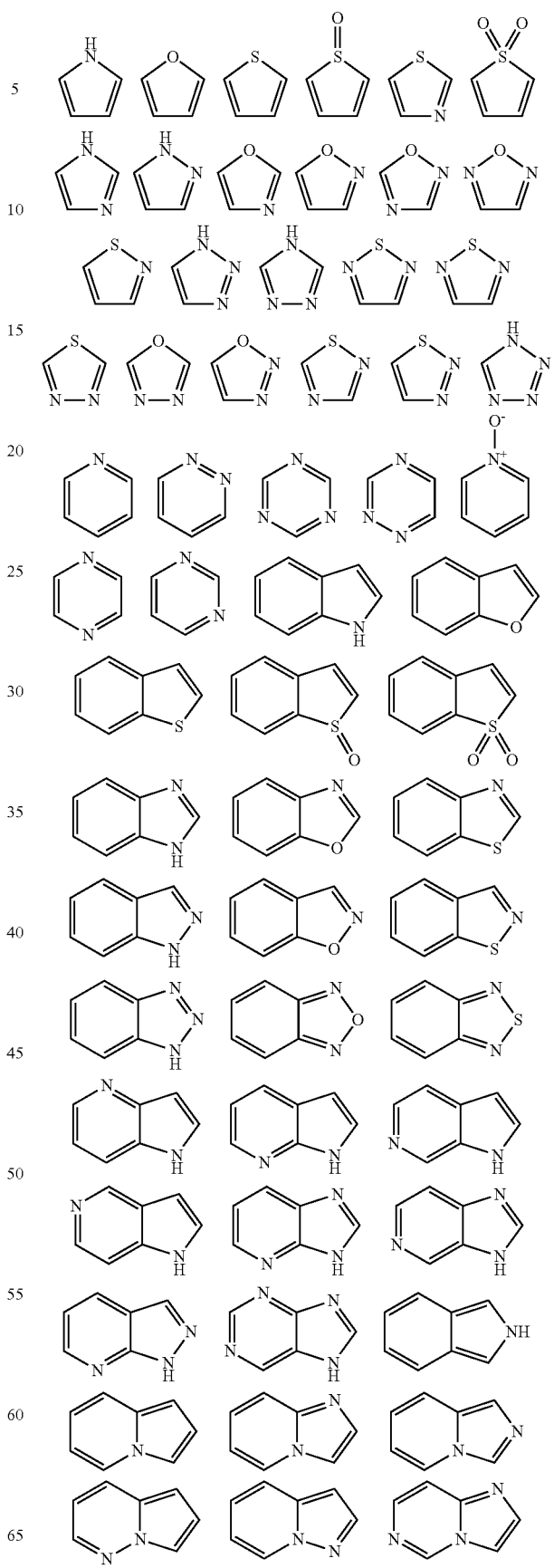

-continued

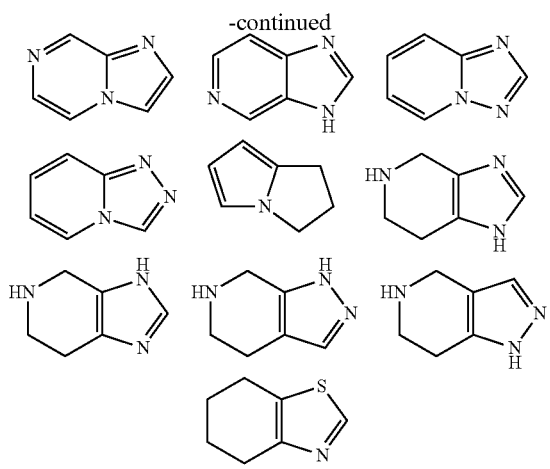

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

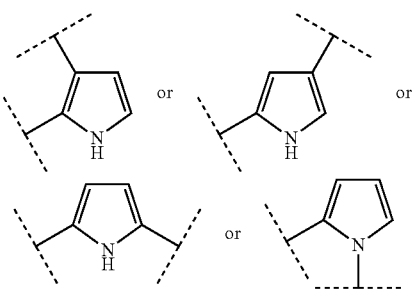

etc.

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =$N_2$ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —$CH_2$— or sulphur atoms of a ring system.

"Substituted with one or more groups" means that the group is substituted with one, two, three, four, five or more groups depending on the valency of the group which is substituted. The skilled person will have no difficulties to establish how many hydrogens can be substituted in a group. Preferably, the referred group is substituted with one, two or three further groups. More preferably, the group is substituted with one or two groups.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof).

Salts of acids other than those mentioned above, which are useful for example for purifying or isolating the compounds from the reaction mixtures (e.g. trifluoroacetates), are also to be regarded as part of the invention.

In a representation such as for example

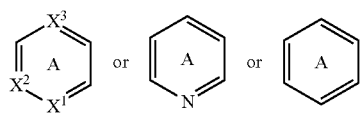

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

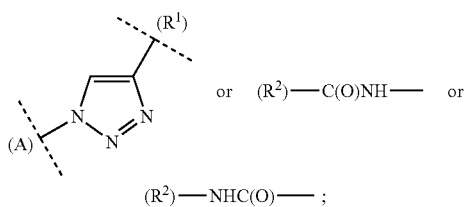

Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| ACN, CH$_3$CN | acetonitrile |
|---|---|
| BINAP | 2,2'-bis(diphenylphosphino)-1,1'-binaphthyl |
| Boc | tert.butoxy carbonyl; di-tert-butyl dicarbonate |
| Boc$_2$O | Boc anhydride |
| CO | carbon monoxide |
| DCM | dichloromethane |

-continued

| dppf | 1,1'-Bis(diphenylphosphino)ferrocene |
|---|---|
| DIPEA | diisopropylethyl amine |
| DMAP | dimethyl-pyridin-4-yl-amine |
| DMF | N,N-dimethylformamide |
| DMSO | dimethylsulphoxide |
| EDTA | ethylenediaminetetraacetic acid |
| EtOAc or EA | ethyl acetate |
| FCS | Fetal calf serum |
| h | hour(s) |
| Hal | halogen |
| HATU | N-[(dimethylamino)-(1H-1,2,3-triazolo[4,5-b]pyridin-1-yl)-methylene]-N-methylmethan-aminium hexafluorophosphate N-oxide |
| HPLC | high performance liquid chromatography |
| K$_2$CO$_3$ | potassium carbonate |
| KOAc | potassium acetate |
| LiHMDS | lithium hexamethyl disilazide |
| M | Molar (mol/L) |
| Min | minute(s) |
| ml | milliliter |
| MS | mass spectrometry |
| N | Normal |
| Na$_2$SO$_4$ | sodium sulfate |
| NMR | nuclear resonance spectroscopy |
| Pd$_2$dba$_3$ | tris(dibenzylideneacetone)dipalladium(0) |
| Pd(dppf)Cl$_2$•CH$_2$Cl$_2$ | [1,1'-Bis(diphenylphosphino)ferrocene]dichloropalladium(II),dichloromethane |
| PE | petrol ether |
| PPh3 | triphenylphosphine |
| DIBAL | diisobutylaluminium hydride |
| RP | reversed phase |
| Rpm | rounds per minute |
| RT or rt | room temperature |
| STAB | sodium triacetoxy borohydride |
| TBME | tert.butyl methyl ether |
| TBTU | o-Benzotriazol-1-yl-N,N,N',N'-tetramethyluronium tetrafluoroborate |
| TEA | triethylamine |
| tert | tertiary |
| TFA | trifluoroacetic acid |
| THF | tetrahydrofuran |
| tR | retention time [min] |
| TRIS | tris(hydroxymethyl)aminomethane |
| wt % | weight percent |
| sat. | Saturated |
| Ar | aromatic |

Other features and advantages of the present invention will become apparent from the following more detailed Examples which exemplarily illustrate the principles of the invention without restricting its scope.

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high pressure chromatography (HPLC) of the example compounds according to the invention is carried out with columns made by Waters (names: Sunfire C18 OBD, 10 μm, 30×100 mm Part. No. 186003971; X-Bridge C18 OBD, 10 μm, 30×100 mm Part. No. 186003930). The compounds are eluted using different gradients of H₂O/ACN wherein 0.2% HCOOH is added to the water (acid conditions). For chromatography under basic conditions the water is made basic according to the following recipe: 5 ml of ammonium hydrogen carbonate solution (158 g to 1 L H₂O) and 2 ml 32% ammonia $_{(aq)}$ are made up to 1 L with H₂O.

The analytical HPLC (reaction monitoring) of intermediate compounds is carried out with columns made by Waters and Phenomenex. The analytical equipment is also provided with a mass detector in each case.

HPLC Mass Spectroscopy/UV Spectrometry

The retention times/MS-ESI⁺ for characterising the example compounds according to the invention are produced using an HPLC-MS apparatus (high performance liquid chromatography with mass detector) made by Agilent. Compounds that elute at the injection peak are given the retention time $t_{Ret.}$=0.

HPLC Preparative Methods
Prep. HPLC1

| | |
|---|---|
| HPLC: | 333 and 334 Pumps |
| Column: | Waters X-Bridge C18 OBD, 10 µm, 30 × 100 mm, Part.No. 186003930 |
| Solvent: | A: 10 mM NH₄HCO₃ in H₂O; B: Acetonitril (HPLC grade) |
| Detection: | UV/Vis-155 |
| Flow: | 50 ml/min |
| Gradient: | 0.00-1.50 min: 1.5% B |
| | 1.50-7.50 min: varying |
| | 7.50-9.00 min: 100% B |

Prep. HPLC2

| | |
|---|---|
| HPLC: | 333 and 334 Pumps |
| Column: | Waters Sunfire C18 OBD, 10 µm, 30 × 100 mm, Part.No. 186003971 |
| Solvent: | A: H₂O + 0.2% HCOOH; B: Acetonitril (HPLC grade) + 0.2% HCOOH |
| Detection: | UV/Vis-155 |
| Flow: | 50 ml/min |
| Gradient: | 0.00-1.50 min: 1.5% B |
| | 1.50-7.50 min: varying |
| | 7.50-9.00 min: 100% B |

Prep. HPLC3

| | |
|---|---|
| HPLC: | Gilson GX-281 |
| Column: | Sunfire Prep C18, 5 µm |
| Solvent: | A: H₂O (0.1% formic acid); B: Acetonitril (HPLC grade) |
| Detection: | UV/Vis-155 50 ml/min |
| Gradient: | 0.00-10 min: 20% → 98% B |

HPLC Analytical Methods
LCMS BAS1

| | |
|---|---|
| HPLC: | Agilent 1100 Series |
| MS: | Agilent LC/MSD SL |
| Column: | Phenomenex Mercury Gemini C18, 3 µm, 2 × 20 mm, Part.No. 00M-4439-B0-CE |
| Solvent: | A: 5 mM NH₄HCO₃/20 mM NH₃ in H₂O; B: Acetonitril (HPLC grade) |
| Detection: | MS: Positive and negative mode |
| Mass range: | 120-900 m/z |
| Flow: | 1.00 ml/min |
| Column temperature: | 40° C. |
| Gradient: | 0.00-2.50 min: 5% → 95% B |
| | 2.50-2.80 min: 95% B |
| | 2.81-3.10 min: 95% → 5% B |

FECB5

| | |
|---|---|
| HPLC: | Agilent 1100/1200 Series |
| MS: | Agilent LC/MSD SL |
| Column: | Waters X-Bridge C18 OBD, 5 µm, 2.1 × 50 mm |
| Solvent: | A: 5 mM NH₄HCO₃/19 mM NH₃ in H₂O; B: Acetonitril (HPLC grade) |
| Detection: | MS: Positive and negative mode |
| Mass range: | 105-1200 m/z |
| Flow: | 1.20 ml/min |
| Column temperature: | 35° C. |
| Gradient: | 0.00-1.25 min: 5% → 95% B |
| | 1.25-2.00 min: 95% B |
| | 2.00-2.01 min: 95% → 5% B |

VAB

| | |
|---|---|
| HPLC: | Agilent 1100/1200 Series |
| MS: | Agilent LC/MSD SL |
| Column: | Waters X-Bridge BEH C18, 2.5 µm, 2.1 × 30 mm XP |
| Solvent: | A: 5 mM NH₄HCO₃/19 mM NH₃ in H₂O; B: Acetonitril (HPLC grade) |
| Detection: | MS: Positive and negative mode |
| Mass range: | 100-1200 m/z |
| Flow: | 1.40 ml/min |
| Column temperature: | 45° C. |
| Gradient: | 0.00-1.00 min: 5% → 100% B |
| | 1.00-1.37 min: 100% B |
| | 1.37-1.40 min: 100% → 5% B |

BFEC

| | |
|---|---|
| HPLC: | Agilent 1260 Series |
| MS: | Agilent 6130 Quadrupol (API-ES) |
| Column: | Waters X-Bridge BEH C18, 2.5 µm, 2.1 × 30 mm XP |
| Solvent: | A: 5 mM NH₄HCO₃/19 mM NH₃ in H₂O; B: Acetonitril (HPLC grade) |
| Detection: | MS: Positive and negative mode |
| Mass range: | 100-1200 m/z |
| Flow: | 1.40 ml/min |
| Column temperature: | 45° C. |
| Gradient: | 0.00-1.00 min: 15% → 95% B |
| | 1.00-1.30 min: 95% B |
| | 1.30-1.40 min: 95% → 15% B |

LCMS-FA2

| | |
|---|---|
| HPLC: | Water UPLC |
| MS: | Micromass Triple quad |
| Column: | Aquity UPLC BEH C18, 1.7 µm, 2.1 × 100 mm |
| Solvent: | A: 0.1% formic acid in Acetonitrile; B: 0.1% formic acid in water |
| Detection: | ES/APCI MODE |
| Flow: | 0.4 ml/min |
| Column temperature: | 40° C. |

-continued

| Gradient: | 0.0-1.0 min: | 90 B% → 90 B% |
| --- | --- | --- |
| | 1.0-4.5 min: | 90 B% → 25 B% |
| | 4.5-5.5 min: | 25 B% → 25 B% |
| | 5.5-6.0 min: | 25 B% → 5 B% |
| | 6.0-7.0 min: | 5 B% → 5 B% |

LCMS-FA3

| HPLC: | Water UPLC | |
| --- | --- | --- |
| MS: | Micromass Triple quad | |
| Column: | Aquity UPLC HSS T3, 1.7 µm, 2.1 × 100 mm | |
| Solvent: | A: 0.1% formic acid in Acetonitrile; B: 0.1% formic acid in water | |
| Detection: | ES/APCI MODE | |
| Flow: | 0.4 ml/min | |
| Column temperature: | | 40° C. |
| Gradient: | 0.00-1.00 min: | 90 B% → 90 B% |
| | 1.00-4.00 min: | 90 B% → 25 B% |
| | 4.00-5.00 min: | 25 B% → 25 B% |
| | 5.00-5.5 min: | 25 B% → 5 B% |
| | 5.5-7.0 min: | 5 B% → 5 B% |

LCMS-MS Ammonium Acetate-1

| HPLC: | Agilent 1200 RRLC | |
| --- | --- | --- |
| MS: | 6130-Single quad | |
| Column: | Xbridge C-18, 3.5 µm, 4.6 × 75 mm | |
| Solvent: | A: Acetonitrile; B: 5mM Ammoniumacetate in water | |
| Detection: | ES/APCI MODE | |
| Flow: | 0.8 ml/min | |
| Column temperature: | | 40° C. |
| Gradient: | 0.00-1.8 min: | 90 B% → 90 B% |
| | 1.8-3.8 min: | 90 B% → 25 B% |
| | 3.8-5.8 min: | 25 B% → 25 B% |
| | 5.8-6.0 min: | 25 B% → 5 B% |
| | 6.0-7.0 min: | 5 B% → 5 B% |

10-90 AB_2minLCMS

| HPLC: | LC-20AB, SPD-M20A 190-370 nm | |
| --- | --- | --- |
| MS: | LCMS-2010EV MS, SHAMADZU | |
| Column: | Halo-C18, 2.7 µm, 2.1 × 3 mm | |
| Solvent: | A: water containing 0.0375% TFA; B: Acetonitrile containing 0.018% TFA | |
| Detection: | Positive | |
| Mass range: | 100-1000 m/z | |
| Flow: | 1.0 ml/min | |
| Column temperature: | | 50° C. |
| Gradient: | 0.00-1.15 min: | 90 A% → 10 A% |
| | 1.15-1.55 min: | 10 A% → 10 A% |
| | 1.55-1.56 min: | 10 A% → 90 A% |
| | 1.56-2.00 min: | 90 A% → 90 A% |

PREPARATION OF THE COMPOUNDS ACCORDING TO THE INVENTION

The compounds according to the invention are prepared by the methods of synthesis described hereinafter, in which the substituents of the general formula have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Unless otherwise specified, the substituents $R^1$ through $R^3$ and $X_1$ through $X_6$ of the following reaction schemes are as defined in the description and claims.

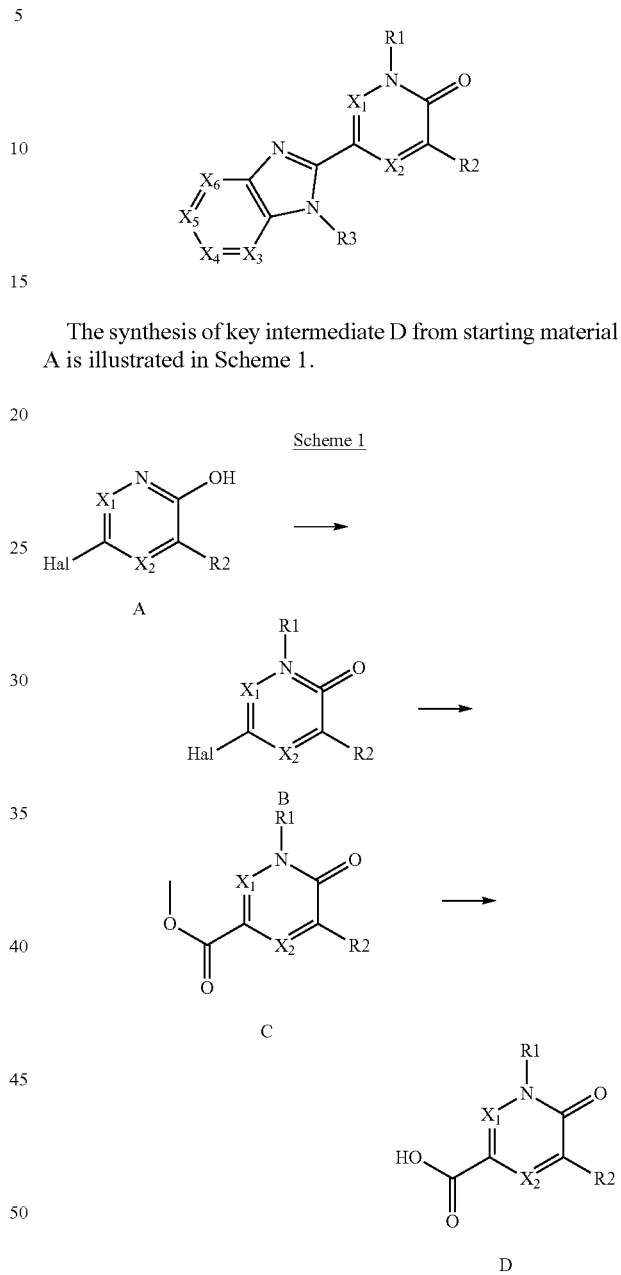

The synthesis of key intermediate D from starting material A is illustrated in Scheme 1.

Starting materials A (e.g. $R^1$=H, $R^2$=Me, $X_1$, $X_2$=CH, Hal=Br; $R^1$=H, $R^2$=Me, $X_1$=CH, $X_2$=N, Hal=Br; $R^1$, $R^2$=H, $X_1$=CH, $X_2$=N, Hal=Br), B (e.g. $R^1$, $R^2$=Me, $X_1$=N, $X_2$=CH, Hal=Cl) or D (e.g. $R^1$=Me, $R^2$=H, $X_1$, $X_2$=CH; $R^1$=Me, $R^2$=NO$_2$, $X_1$, $X_2$=CH; $R^1$=Me, $R^2$=H, $X_1$=N, $X_2$=CH) are commercially available. Starting from A, an alkylation can be used to introduce $R^1$, which leads to B. Compound C can be synthesized applying a carbonylation reaction using carbon monoxide. After cleavage of the ester the central intermediate D can be obtained.

The synthesis of compounds of formula I-IV from key intermediate D and E-1-E-4 is illustrated in Scheme 2 and Scheme 3.

Scheme 2

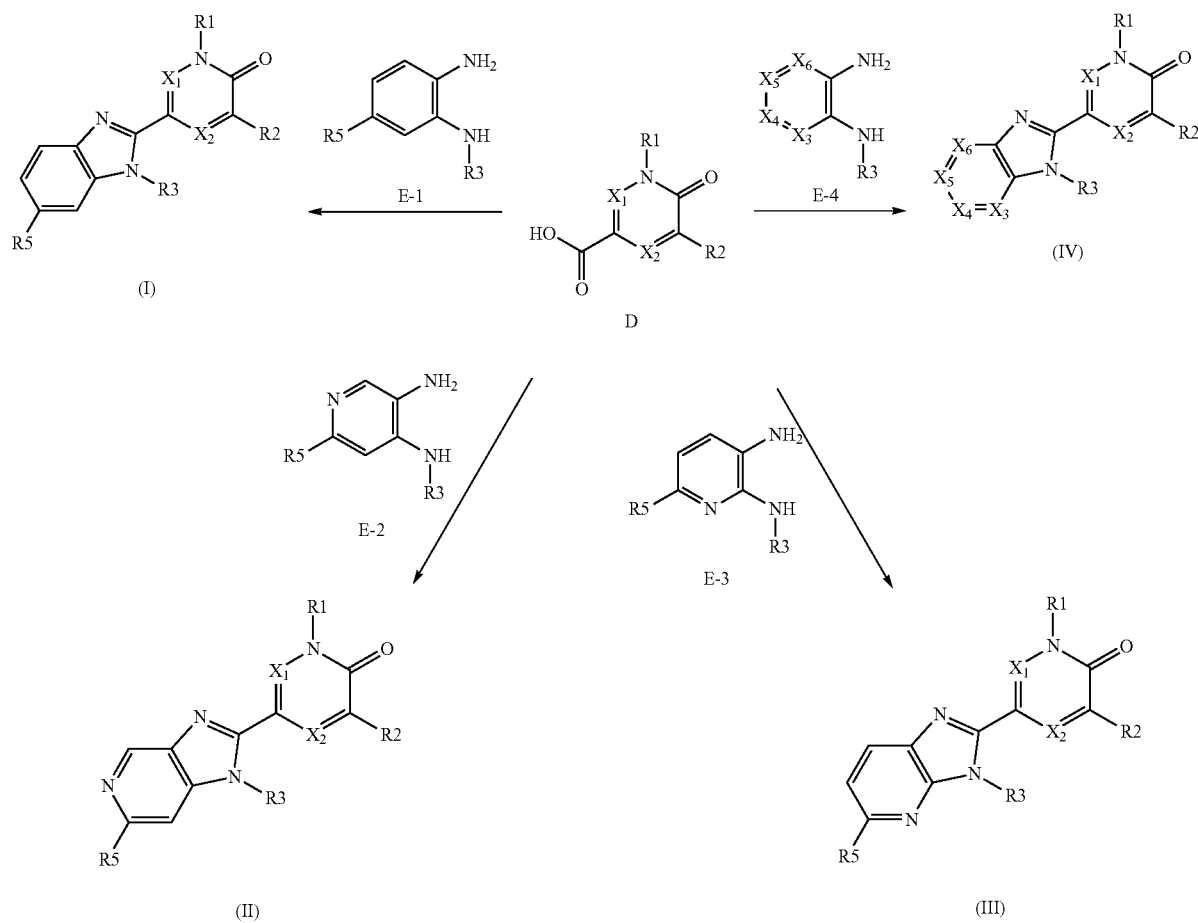

The acid D is activated using the typical reagents (e.g. TBTU or HATU) or by in situ reaction to the acid chloride. The activated acid is than coupled with the corresponding aromatic diamine E-1-E-4 followed by a ring closing reaction using acetic acid or poly phosphoric acid.

Scheme 3

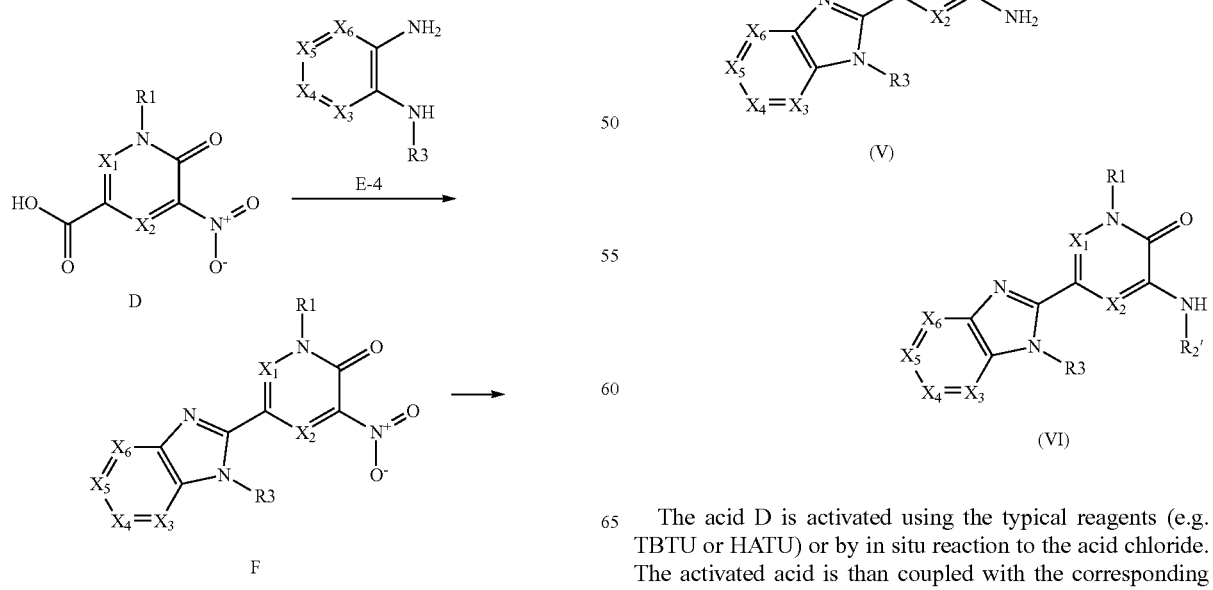

The acid D is activated using the typical reagents (e.g. TBTU or HATU) or by in situ reaction to the acid chloride. The activated acid is than coupled with the corresponding aromatic diamine E-4 followed by a ring closing reaction using acetic acid or poly phosphoric acid. Reduction of the nitro group leads to the final compounds of the type (V). Reductive amination, alkylation or formamide generation/reduction generates compounds of the type (VI).

Preparation of Intermediate D-1

1,5-Dimethyl-6-oxo-1,6-dihydropyridine-3-carboxylic acid

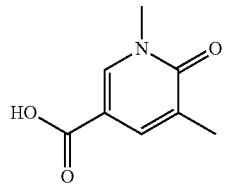

Reaction scheme:

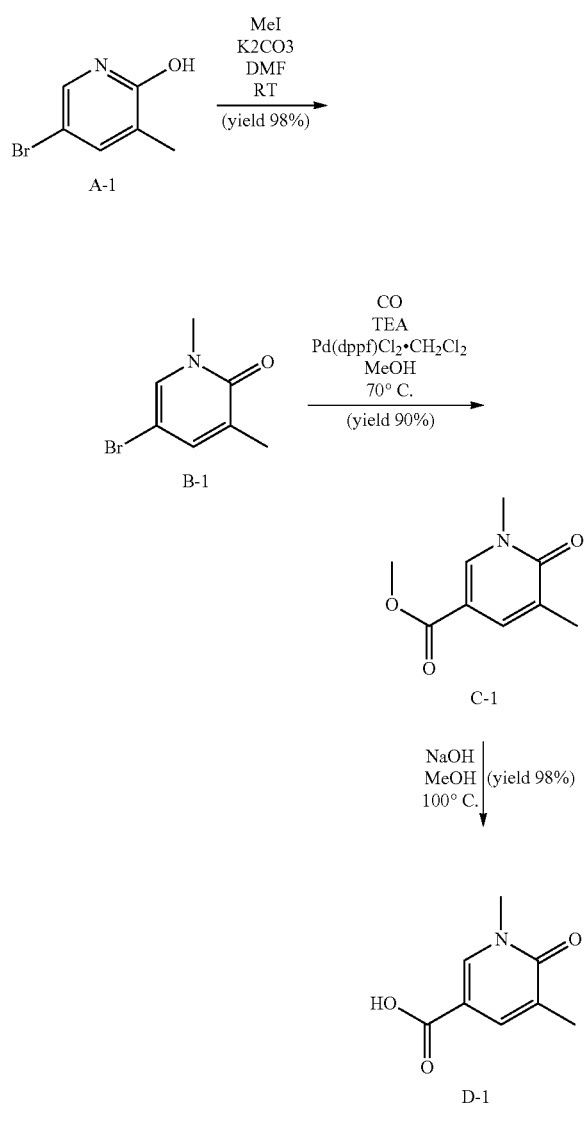

5-Bromo-1,3-dimethyl-1H-pyridin-2-one B-1

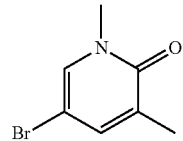

To a suspension of 5-bromo-2-hydroxy-3-methyl pyridine A1 (1.000 g; 5.053 mmol) and potassium carbonate (1.397 g; 10.105 mmol) in DMF (5.000 ml) is carefully added iodomethane (0.346 ml; 5.558 mmol). The reaction mixture is stirred overnight (16 h) at room temperature. The reaction mixture is then quenched with 10% ammonia solution (10 ml) and 30 ml water is added. It is extracted with 3×50 ml EtOAc. The combined organic layer is dried with $Na_2SO_4$, filtered and concentrated under reduced pressure to afford the product.

Yield: 98% (1.0 g; 4.95 mmol)
HPLC-MS: $(M+H)^+$=202/204; $t_{Ret}$=0.65 min; method LCMS BAS1

1,5-Dimethyl-6-oxo-1,6-dihydro-pyridine-3-carboxylic acid methyl ester C-1

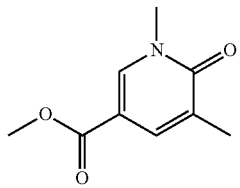

In the carbonylation reactor from Büchi Glas Uster, 5-Bromo-1,3-dimethyl-1H-pyridin-2-one B-1 (3.300 g; 16.006 mmol) is dissolved in MeOH (80.000 ml) and TEA (5.399 ml; 40.015 mmol) is added. Then $Pd(dppf)Cl_2 \cdot CH_2Cl_2$ (389.000 mg; 0.476 mmol) is added and the reactor is closed and filled with carbon monoxide (8 bar). The reactor is heated to 70° C. and stirred overnight 18 h. The reaction mixture is filtered through a small pad of silica and washed with ethyl acetate. The filtrate is concentrated under reduced pressure and the residue is purified on silica chromatography Combiflash (Column: Redisep Rf, 120 g; gradient: cHex/EtOAc=100%/0% to 50%/50%; flow rate=30 ml/min, 28 column volumes; detection wavelength: 254 nm). The product containing fractions are combined and concentrated under reduce pressure.

Yield: 90% (2.6 g; 14.35 mmol)
HPLC-MS: $(M+H)^+$=182; $t_{Ret}$=0.49 min; method LCMS BAS1

1,5-Dimethyl-6-oxo-1,6-dihydro-pyridine-3-carboxylic acid D-1

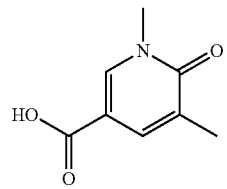

1,5-Dimethyl-6-oxo-1,6-dihydro-pyridine-3-carboxylic acid methyl ester C-1 (2.600 g; 14.350 mmol) is suspended in MeOH. Sodium hydroxide (1 M solution, 45.000 ml; 45.000 mmol) is added and the reaction mixture is heated up to 100° C. (Drysyn, reflux) for 2 h. MeOH is removed under reduced pressure and 1N HCl (46 ml) is added to the solution, precipitation occurs. The precipitate is filtered off and dried under reduced pressure.

Yield: 98% (2.34 g; 14.00 mmol)

HPLC-MS: (M+H)+=168; tRet=0 min; method LCMS BAS1

According to the procedure of D-1 the intermediates D-2-D-4 are synthesized. In the case of D-5, same procedure is used except that the carbonylation is performed before alkylation (carbonylation of 5-bromo-pyrazin-2-ol, followed by N-methylation of 5-hydroxy-pyrazine-2-carboxylic acid methyl ester). D-6 is synthesized following the procedure described for D-1 with the exception of omitting the alkylation step (A-6→C-6 (with R1=H)→D-6). Intermediates D-7 to D-9 are commercially available.

| # | Structure | MS (M + H)+; $t_{Ret.}$ HPLC [min] | HPLC-Method |
|---|---|---|---|
| D-1 | 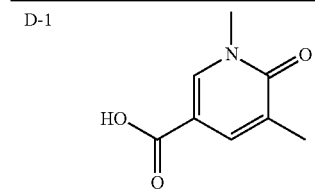 | M + H = 168; $t_{Ret.}$ = 0 min | LCMS BAS1 |
| D-2 | 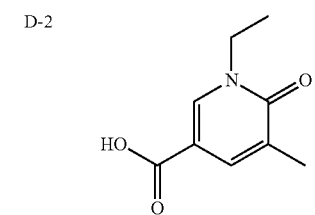 | M + H = 182; $t_{Ret.}$ = 0 min | LCMS BAS1 |
| D-3 | 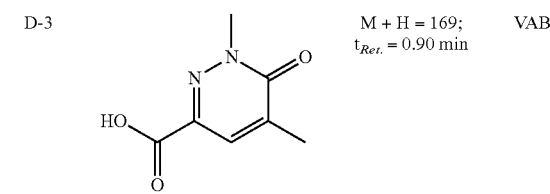 | M + H = 169; $t_{Ret.}$ = 0.90 min | VAB |
| D-4 | 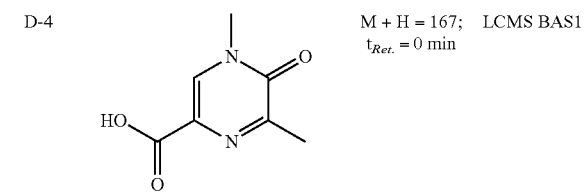 | M + H = 167; $t_{Ret.}$ = 0 min | LCMS BAS1 |
| D-5 | 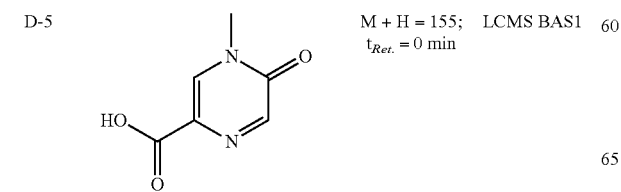 | M + H = 155; $t_{Ret.}$ = 0 min | LCMS BAS1 |
| D-6 | 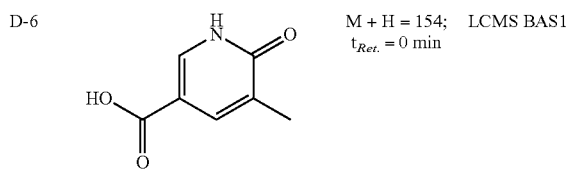 | M + H = 154; $t_{Ret.}$ = 0 min | LCMS BAS1 |
| D-7 | 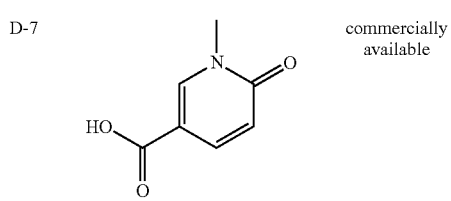 | | commercially available |
| D-8 | 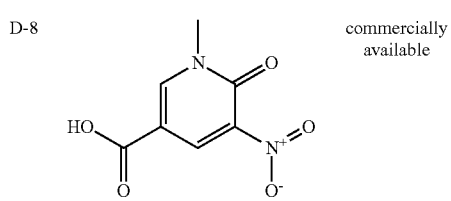 | | commercially available |
| D-9 | 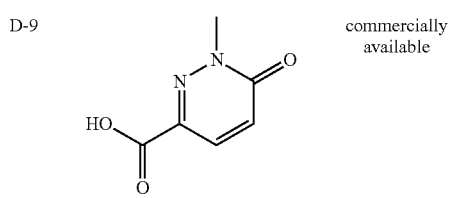 | | commercially available |

General Method for Preparation of Compounds of Formula I

Method 1:

5-[1-benzyl-6-(4-methylpiperazin-1-yl)-1H-1,3-benzodiazol-2-yl]-1,3-dimethyl-1,2-dihydropyridin-2-one I-1

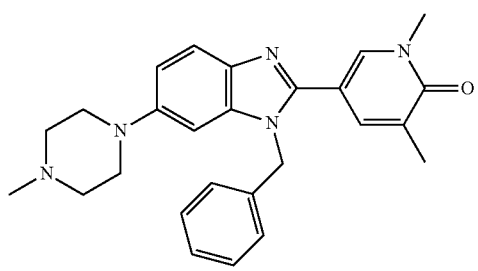

-continued

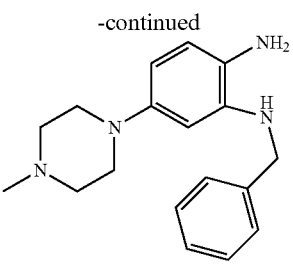

E-1.1

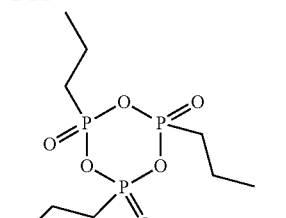

D1

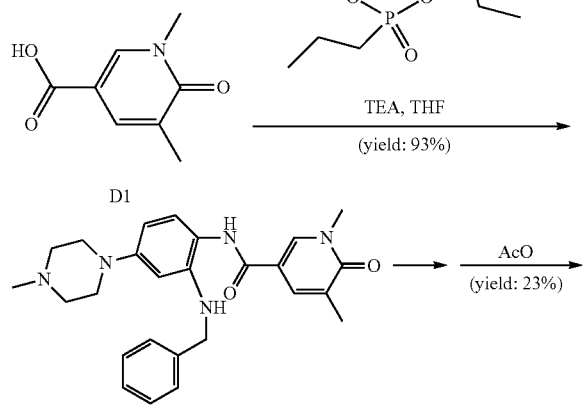

I-1'

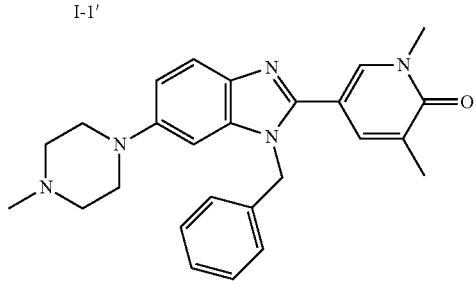

I-

1,5-Dimethyl-6-oxo-1,6-dihydro-pyridine-3-carboxylic acid [2-benzylamino-4-(4-methyl-piperazin-1-yl)-phenyl]-amide I-1'

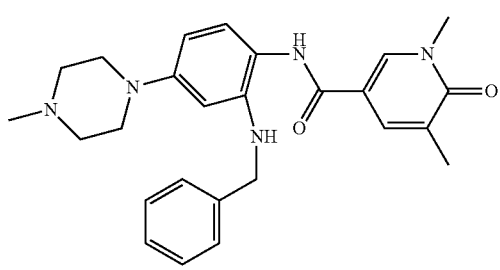 [SMILES: Cc1cc(C(=O)Nc2ccc(N3CCN(C)CC3)cc2NCc2ccccc2)cn(C)c1=O]

To a mixture of 1,5-dimethyl-6-oxo-1,6-dihydro-pyridine-3-carboxylic acid D1 (210.000 mg; 1.256 mmol), N2-Benzyl-4-(4-methyl-piperazin-1-yl)-benzene-1,2-diamine E-1.1 (363.000 mg; 1163.422 µmol) and triethylamine (0.435 ml; 3.141 mmol) in THF (3.000 ml) is added N-propylphosphonic acid anhydride, cyclic trimer (0.880 ml; 1.508 mmol). The mixture is stirred for 5 h at RT. The reaction is quenched with 1M NaOH, diluted with 50 ml water and extracted twice with ethyl acetate (50 ml). The combined organic layer is dried over Na$_2$SO$_4$ and concentrated in vacuum. The residue is used in the next step without further purification Yield: 93% (523 mg; 1.174 mmol).

5-[1-Benzyl-6-(4-methylpiperazin-1-yl)-1H-1,3-benzodiazol-2-yl]-1,3-dimethyl-1,2-dihydropyridin-2-one I-1

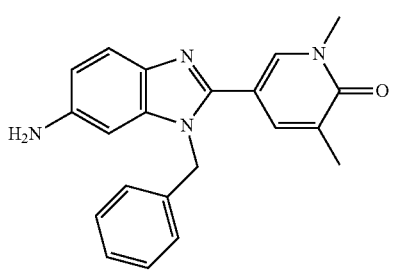

1,5-Dimethyl-6-oxo-1,6-dihydro-pyridine-3-carboxylic acid [2-benzylamino-4-(4-methyl-piperazin-1-yl)-phenyl]-amide I-1' (523.000 mg; 1.174 mmol) is dissolved in acetic acid and stirred at 80° C. overnight. The reaction mixture is concentrated under reduced pressure and the residue is purified on silica chromatography Combiflash (Column: Redisep Rf, 40 g; gradient: DCM/MeOH=100%/0% to 95%/5% over 30 column volumes, then to 90%/10% over 15 column volumes; flow rate=40 ml/min; detection wavelength: 254 nm). Product containing fractions are combined and concentrated under reduce pressure.

Yield: 23% (117 mg; 0.274 mmol)

HPLC-MS: (M+H)+=428; t$_{Ret}$=0.99 min; method LCMS BAS1

Method 2:

5-(6-Amino-1-benzyl-1H-benzoimidazol-2-yl)-1,3-dimethyl-1H-pyridin-2-one I-9

-continued

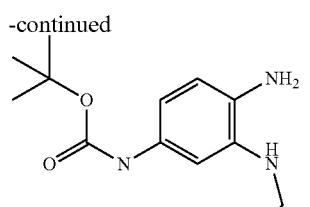

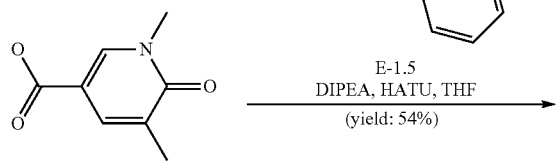

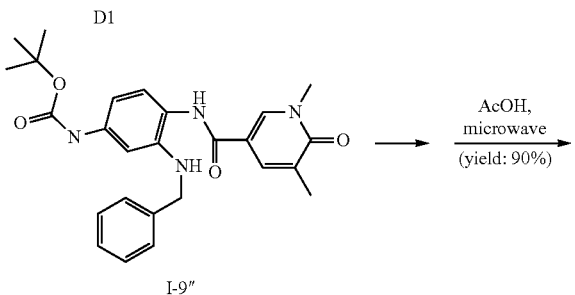

I-9″

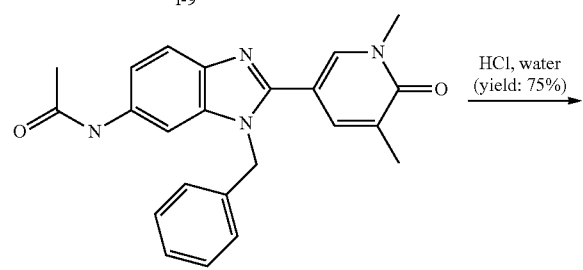

I-9′

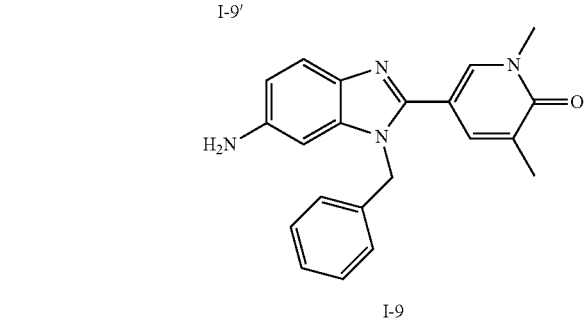

I-9

{3-Benzylamino-4-[(1,5-dimethyl-6-oxo-1,6-dihydro-pyridine-3-carbonyl)-amino]-phenyl}-carbamic acid tert-butyl ester I-9″

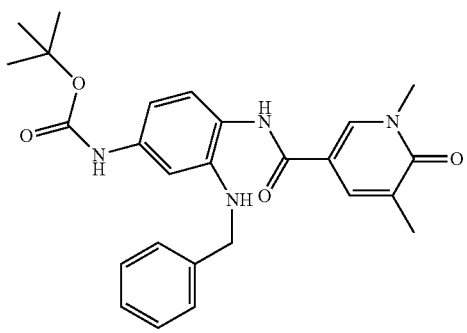 [SMILES: Cc1cc(C(=O)Nc2ccc(NC(=O)OC(C)(C)C)cc2NCc2ccccc2)cn(C)c1=O]

1,5-Dimethyl-6-oxo-1,6-dihydro-pyridine-3-carboxylic acid D1 (5.000 g; 16 mmol) and (4-Amino-3-benzylamino-phenyl)-carbamic acid tert-butyl ester E-1.5 (3.200 g; 19 mmol) are dissolved in THF and and cooled to 0° C. DIPEA (6.186 g; 48 mmol) is then added, the mixture is stirred for 15 min Finally HATU (12.133 g; 32 mmol) is added. The mixture is stirred at room temperature for 1 hr. The reaction is diluted with water and extracted with MeOH/DCM. The combined organic layer is dried over Na$_2$SO$_4$ and concentrated in vacuum. The residue is used in the next step without further purification.

Yield: 54% (4.000 g; 8.648 mmol).

N-[3-Benzyl-2-(1,5-dimethyl-6-oxo-1,6-dihydro-pyridin-3-yl)-3H-benzoimidazol-5-yl]-acetamide I-9′

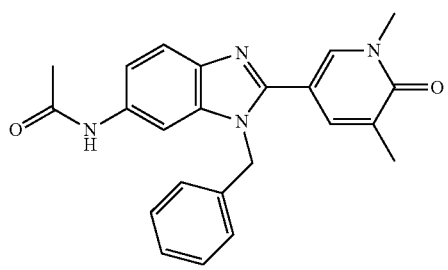 [SMILES: CC(=O)Nc1ccc2nc(-c3cc(C)c(=O)n(C)c3)n(Cc3ccccc3)c2c1]

{3-Benzylamino-4-[(1,5-dimethyl-6-oxo-1,6-dihydro-pyridine-3-carbonyl)-amino]-phenyl}-carbamic acid tert-butyl ester I-9″ (4.000 g; 8.648 mmol) is suspended in acetic acid (5.190 g; 86 mmol) in a microwave vial and heated in the microwave at 150° C. for 1 h. The reaction mixture is then concentrated under reduced pressure. The residue is added to ice water, precipitation occurs. The precipitate is filtered off and dried under vacuum. The residue is used in the next step without further purification. (Yield: 90%, 3.000 g; 7.763 mmol)

5-(6-Amino-1-benzyl-1H-benzoimidazol-2-yl)-1,3-dimethyl-1H-pyridin-2-one I-9

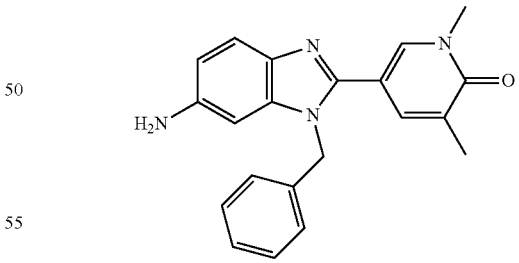

N-[3-Benzyl-2-(1,5-dimethyl-6-oxo-1,6-dihydro-pyridin-3-yl)-3H-benzoimidazol-5-yl]-acetamide I-9″ (3.000 g; 7.763 mmol) is suspended in 8 N HCl (74 mmol). The reaction mixture is stirred for 3 h at 100° C. The reaction is cooled to RT and then quenched slowly with sodium bicarbonate (until reaching a basic pH). The reaction is extracted with MeOH/DCM. The combined organic layer is dried over Na2SO4 and concentrated in vacuum.

Yield: 75% (2.000 g; 5.807 mmol).

Method 3:

5-(1-Benzyl-6-fluoro-1H-benzoimidazol-2-yl)-1,3-dimethyl-1H-pyridin-2-one I-12

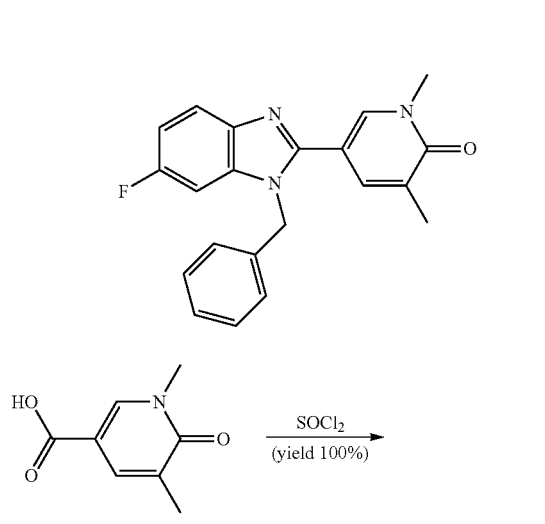

1,5-Dimethyl-6-oxo-1,6-dihydro-pyridine-3-carbonyl chloride D1'

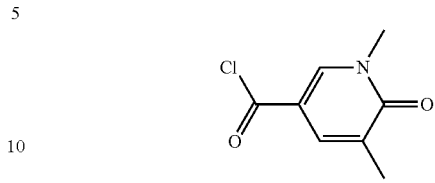

1,5-Dimethyl-6-oxo-1,6-dihydro-pyridine-3-carboxylic acid D1 (500.000 mg; 2.991 mmol) is suspended in thionyl chloride (2.000 ml; 27.536 mmol) and heated for 2 h at 60° C. The reaction mixture is concentrated under reduced pressure. And used in the next reaction without further purification (Yield: 100%).

1,5-Dimethyl-6-methylene-1,6-dihydro-pyridine-3-carboxylic acid (2-benzylamino-4-fluoro-phenyl)-amide I-12'

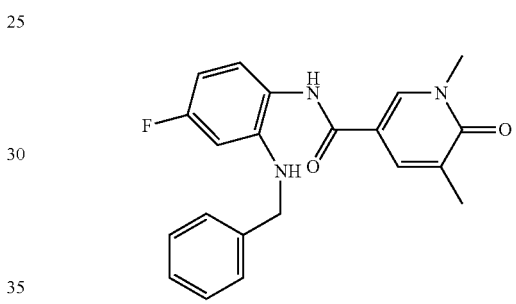

A solution of 1,5-dimethyl-6-oxo-1,6-dihydro-pyridine-3-carbonyl chloride D1' (100.000 mg; 0.598 mmol) in dry DCM (2.000 ml) is added dropwise to a solution of N2-benzyl-4-fluoro-benzene-1,2-diamine hydrochloride E-1.4 (151.180 mg; 0.598 mmol) in DCM (2.000 ml) and triethylamin (0.249 ml; 1.795 mmol). The mixture is stirred for 1 h. Precipitation occurs; the residue is filtered off and washed with DCM (2 ml). The precipitate is then dried under vacuum (Yield: 85%, 186 mg; 0.509 mmol)

5-(1-Benzyl-6-fluoro-1H-benzoimidazol-2-yl)-1,3-dimethyl-1H-pyridin-2-one I-12

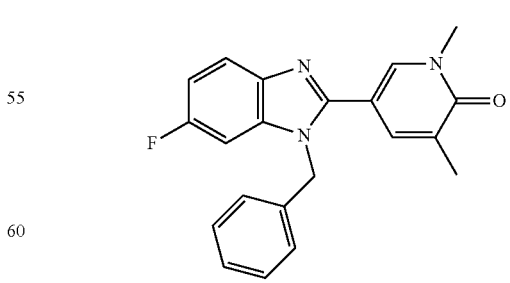

1,5-Dimethyl-6-methylene-1,6-dihydro-pyridine-3-carboxylic acid (2-benzylamino-4-fluoro-phenyl)-amide I-12' (186.000 mg; 0.509 mmol) is dissolved in acetic acid and stirred at 150° C. for 1 h in the microwave. The reaction mixture is then concentrated under reduced pressure and purified on silica chromatography Combiflash (Column: Redisep Rf, 12 g; gradient: DCM/MeOH=100%/0% to 90%/10%; flow rate=30 ml/min; 28 column volumes; detection wavelength: 254 nm). The product containing fractions are combined and concentrated under reduce pressure. The product is then dissolved in acetonitrile:water 1:1 and freeze dried.

Yield: 62% (109 mg; 0.313 mmol)

HPLC-MS: (M+H)+=348; $t_{Ret}$=1.12 min; method LCMS BAS1

According to the procedures of I-1, I-9 or I-12 the following examples are synthesized.

| # | Structure | MS (M + H)+; $t_{Ret.}$ HPLC [min] | HPLC-Method |
|---|---|---|---|
| I-1 | 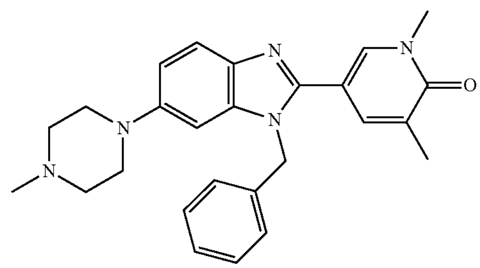 [SMILES: Cc1cc(-c2nc3ccc(N4CCN(C)CC4)cc3n2Cc2ccccc2)cn(C)c1=O] | M + H = 428; $t_{Ret.}$ = 0.99 | LCMS BAS1 |
| I-2 | 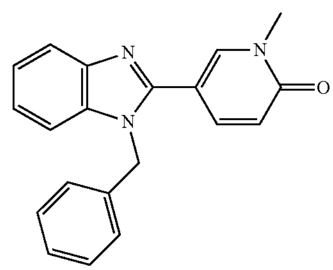 [SMILES: Cn1cc(-c2nc3ccccc3n2Cc2ccccc2)ccc1=O] | M + H = 316; $t_{Ret.}$ = 1.02 | LCMS BAS1 |
| I-3 | 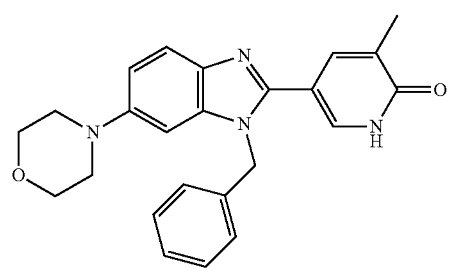 [SMILES: Cc1cc(-c2nc3ccc(N4CCOCC4)cc3n2Cc2ccccc2)c[nH]c1=O] | M + H = 401; $t_{Ret.}$ = 0.96 | LCMS BAS1 |
| I-4 | 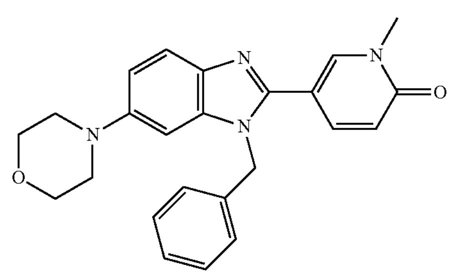 [SMILES: Cn1cc(-c2nc3ccc(N4CCOCC4)cc3n2Cc2ccccc2)ccc1=O] | M + H = 401; $t_{Ret.}$ = 0.96 | LCMS BAS1 |
| I-5 | 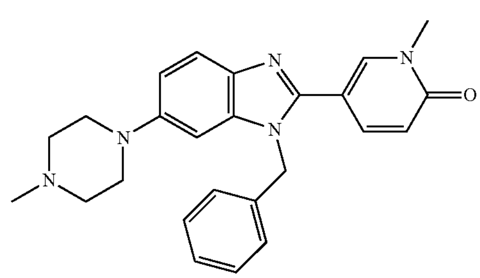 [SMILES: CN1CCN(c2ccc3nc(-c4ccc(=O)n(C)c4)n(Cc4ccccc4)c3c2)CC1] | M + H = 414; $t_{Ret.}$ = 0.95 | LCMS BAS1 |

-continued

| # | Structure | MS (M + H)+; t_Ret. HPLC [min] | HPLC-Method |
|---|---|---|---|
| I-6 | 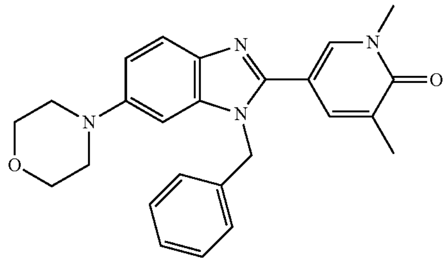 [SMILES: Cc1cc(-c2nc3ccc(N4CCOCC4)cc3n2Cc2ccccc2)cn(C)c1=O] | M + H = 415; t_Ret. = 1.03 | LCMS BAS1 |
| I-7 | 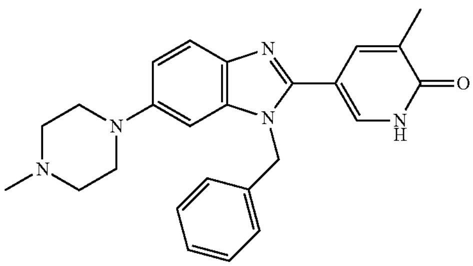 [SMILES: Cc1cc(-c2nc3ccc(N4CCN(C)CC4)cc3n2Cc2ccccc2)c[nH]c1=O] | M + H = 414; t_Ret. = 0.95 | LCMS BAS1 |
| I-8 | 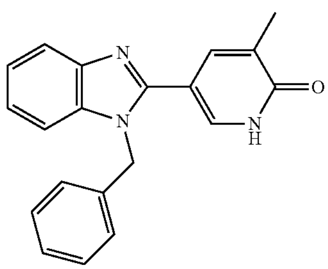 [SMILES: Cc1cc(-c2nc3ccccc3n2Cc2ccccc2)c[nH]c1=O] | M + H = 316; t_Ret. = 1.02 | LCMS BAS1 |
| I-9 | 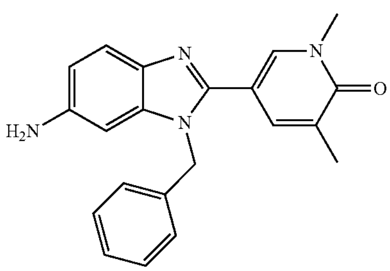 [SMILES: Cc1cc(-c2nc3ccc(N)cc3n2Cc2ccccc2)cn(C)c1=O] | M + H = 345; t_Ret. = 0.87 | LCMS BAS1 |
| I-10 | 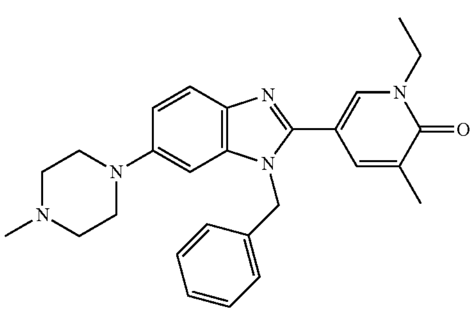 [SMILES: CCn1cc(-c2nc3ccc(N4CCN(C)CC4)cc3n2Cc2ccccc2)cc(C)c1=O] | M + H = 442; t_Ret. = 1.06 | LCMS BAS1 |

-continued

| # | Structure | MS (M + H)+; t_Ret. HPLC [min] | HPLC-Method |
|---|---|---|---|
| I-11 | 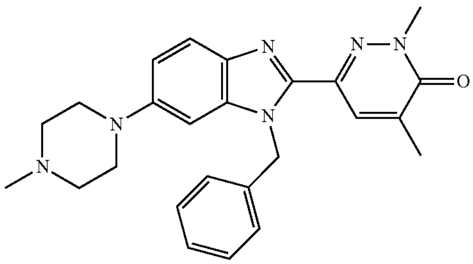 [SMILES: Cc1cc(-c2nc3ccc(N4CCN(C)CC4)cc3n2Cc2ccccc2)nn(C)c1=O] | M + H = 429; t_Ret. = 1.12 | LCMS BAS1 |
| I-12 | 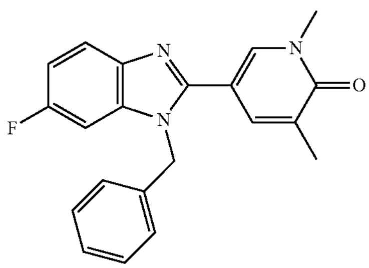 [SMILES: Cc1cc(-c2nc3ccc(F)cc3n2Cc2ccccc2)cn(C)c1=O] | M + H = 348; t_Ret. = 1.12 | LCMS BAS1 |
| I-13 | 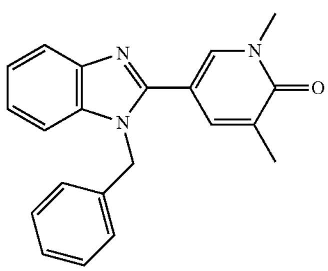 [SMILES: Cc1cc(-c2nc3ccccc3n2Cc2ccccc2)cn(C)c1=O] | M + H = 330; t_Ret. = 1.09 | LCMS BAS1 |
| I-14 | 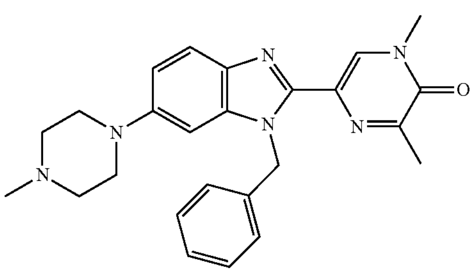 | M + H = 429; t_Ret. = 1.06 | LCMS BAS1 |
| I-15 | 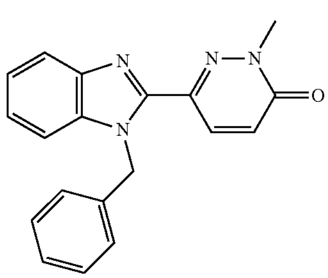 [SMILES: Cn1nc(-c2nc3ccccc3n2Cc2ccccc2)ccc1=O] | M + H = 317; t_Ret. = 1.12 | LCMS BAS1 |

-continued

| # | Structure | MS (M + H)+; t_Ret. HPLC [min] | HPLC-Method |
|---|---|---|---|
| I-16 | 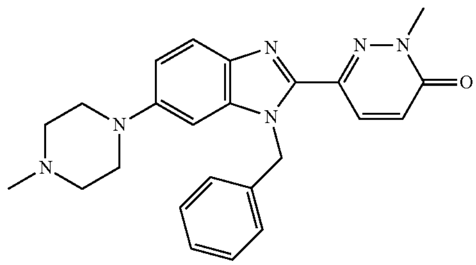 [SMILES: CN1CCN(c2ccc3nc(-c4ccc(=O)n(C)n4)n(Cc4ccccc4)c3c2)CC1] | M + H = 415; t_Ret. = 1.05 | LCMS BAS1 |
| I-17 | 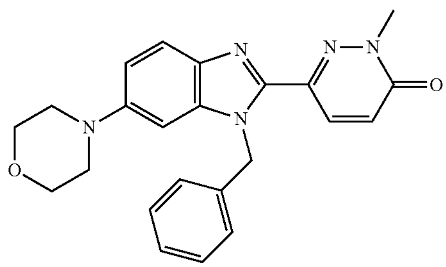 [SMILES: Cn1nc(-c2nc3ccc(N4CCOCC4)cc3n2Cc2ccccc2)ccc1=O] | M + H = 401; t_Ret. = 1.06 | LCMS BAS1 |
| I-18 | 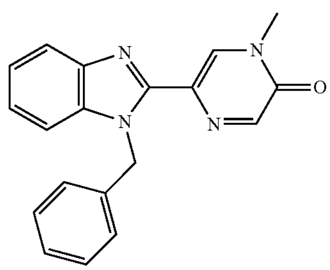 [SMILES: Cn1cc(-c2nc3ccccc3n2Cc2ccccc2)ncc1=O] | M + H = 317; t_Ret. = 1.06 | LCMS BAS1 |
| I-19 | 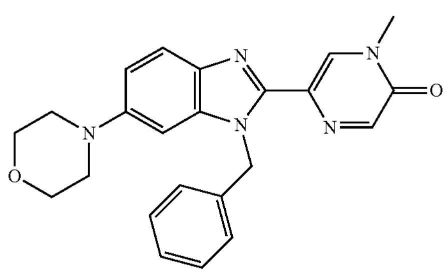 [SMILES: Cn1cc(-c2nc3ccc(N4CCOCC4)cc3n2Cc2ccccc2)ncc1=O] | M + H = 402; t_Ret. = 0.99 | LCMS BAS1 |
| I-20 | 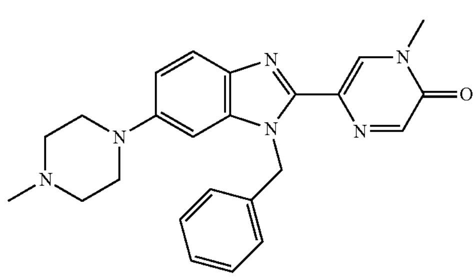 [SMILES: CN1CCN(c2ccc3nc(-c4cn(C)c(=O)cn4)n(Cc4ccccc4)c3c2)CC1] | M + H = 415; t_Ret. = 0.97 | LCMS BAS1 |

-continued

| # | Structure | MS (M + H)+; t_Ret. HPLC [min] | HPLC-Method |
|---|---|---|---|
| I-21 | 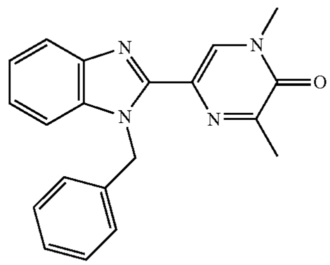 [SMILES: Cc1nc(-c2nc3ccccc3n2Cc2ccccc2)cn(C)c1=O] | M + H = 331; t_Ret. = 1.15 | LCMS BAS1 |
| I-22 | 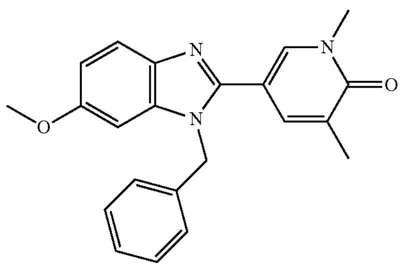 [SMILES: COc1ccc2nc(-c3cc(C)c(=O)n(C)c3)n(Cc3ccccc3)c2c1] | M + H = 360; t_Ret. = 1.08 | LCMS BAS1 |
| I-23 | 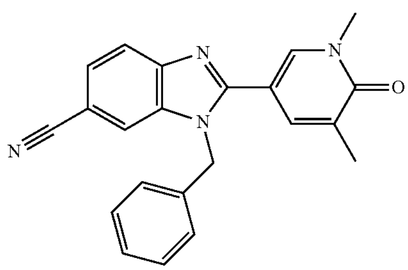 [SMILES: Cc1cc(-c2nc3ccc(C#N)cc3n2Cc2ccccc2)cn(C)c1=O] | M + H = 355; t_Ret. = 1.06 | LCMS BAS1 |
| I-24 | 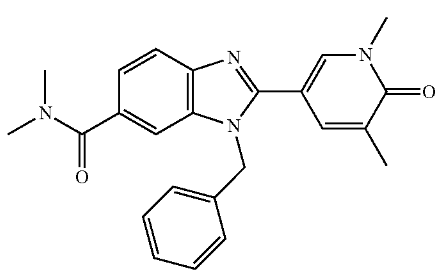 [SMILES: Cc1cc(-c2nc3ccc(C(=O)N(C)C)cc3n2Cc2ccccc2)cn(C)c1=O] | M + H = 401; t_Ret. = 0.93 | LCMS BAS1 |
| I-25 | 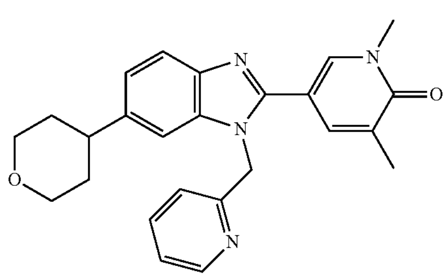 [SMILES: Cc1cc(-c2nc3ccc(C4CCOCC4)cc3n2Cc2ccccn2)cn(C)c1=O] | M + H = 415; t_Ret. = 0.97 | LCMS BAS1 |

-continued

| # | Structure | MS (M + H)+; t_Ret. HPLC [min] | HPLC-Method |
|---|---|---|---|
| I-26 | 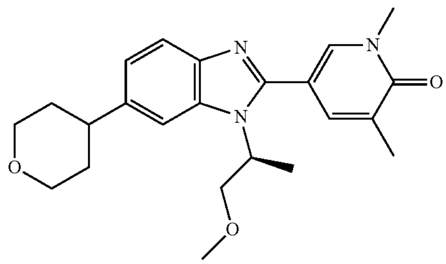 [SMILES: COC[C@H](C)n1c(-c2cc(C)c(=O)n(C)c2)nc2ccc(C3CCOCC3)cc21] | M + H = 396; t_Ret. = 1.01 | LCMS BAS1 |
| I-27 | 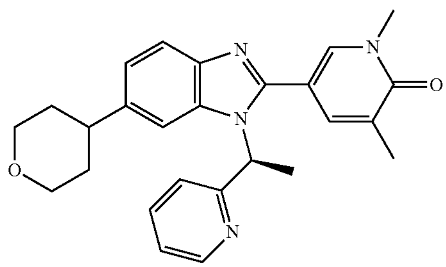 [SMILES: Cc1cc(-c2nc3ccc(C4CCOCC4)cc3n2[C@@H](C)c2ccccn2)cn(C)c1=O] | M + H = 429; t_Ret. = 1.02 | LCMS BAS1 |
| I-28 | 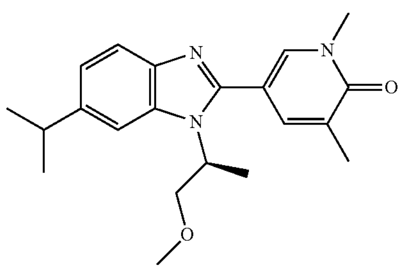 [SMILES: COC[C@H](C)n1c(-c2cc(C)c(=O)n(C)c2)nc2ccc(C(C)C)cc21] | M + H = 354; t_Ret. = 1.19 | LCMS BAS1 |
| I-29 | 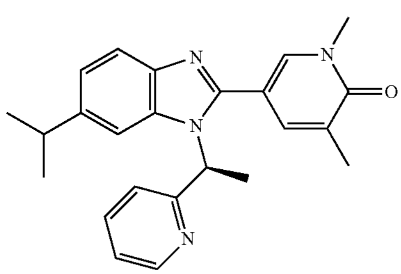 [SMILES: Cc1cc(-c2nc3ccc(C(C)C)cc3n2[C@@H](C)c2ccccn2)cn(C)c1=O] | M + H = 387; t_Ret. = 1.20 | LCMS BAS1 |
| I-30 | 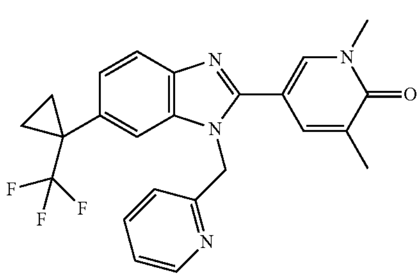 [SMILES: Cc1cc(-c2nc3ccc(C4(C(F)(F)F)CC4)cc3n2Cc2ccccn2)cn(C)c1=O] | M + H = 439; t_Ret. = 1.33 | LCMS BAS1 |

| # | Structure | MS (M + H)+; $t_{Ret.}$ HPLC [min] | HPLC-Method |
|---|---|---|---|
| I-31 | 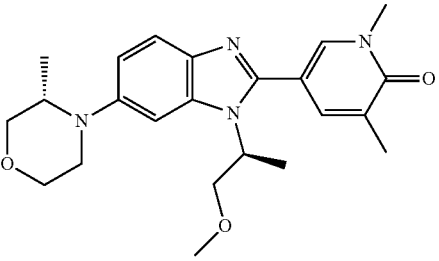 [SMILES: COC[C@H](C)n1c(-c2cc(C)c(=O)n(C)c2)nc2ccc(N3CCOC[C@@H]3C)cc21] | M + H = 411; $t_{Ret.}$ = 1.12 | LCMS BAS1 |
| I-32 | 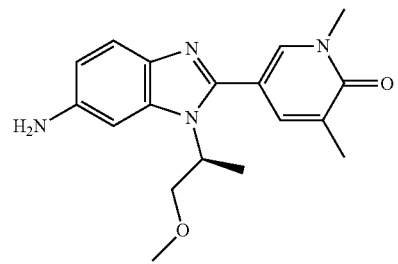 [SMILES: COC[C@H](C)n1c(-c2cc(C)c(=O)n(C)c2)nc2ccc(N)cc21] | M + H = 327; $t_{Ret.}$ = 0.90 | LCMS BAS1 |
| I-33 | 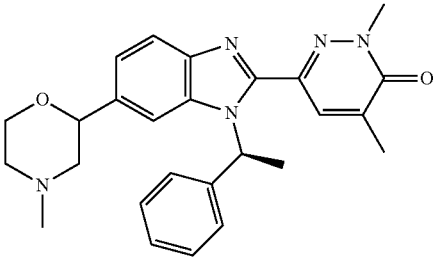 [SMILES: Cc1cc(-c2nc3ccc(C4CN(C)CCO4)cc3n2[C@@H](C)c2ccccc2)nn(C)c1=O] | M + H = 444; $t_{Ret.}$ = 1.14 | LCMS BAS1 |
| I-34 | 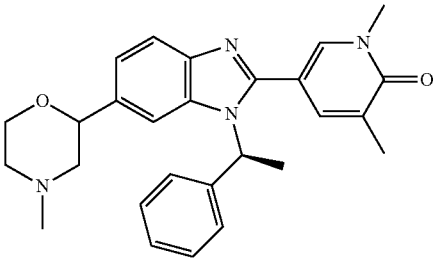 [SMILES: Cc1cc(-c2nc3ccc(C4CN(C)CCO4)cc3n2[C@@H](C)c2ccccc2)cn(C)c1=O] | M + H = 443; $t_{Ret.}$ = 1.04 | LCMS BAS1 |
| I-35 | 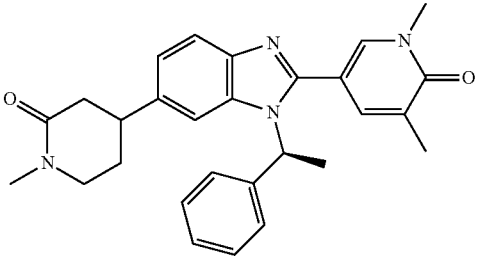 [SMILES: Cc1cc(-c2nc3ccc(C4CCN(C)C(=O)C4)cc3n2[C@@H](C)c2ccccc2)cn(C)c1=O] | M + H = 455; $t_{Ret.}$ = 0.99 | LCMS BAS1 |

-continued

| # | Structure | MS (M + H)+; t_Ret. HPLC [min] | HPLC-Method |
|---|---|---|---|
| I-36 | 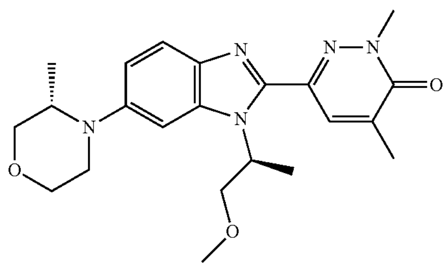 [SMILES: COC[C@H](C)n1c(-c2cc(C)c(=O)n(C)n2)nc2ccc(N3CCOC[C@@H]3C)cc21] | M + H = 412; t_Ret. = 1.05 | LCMS BAS1 |
| I-37 | 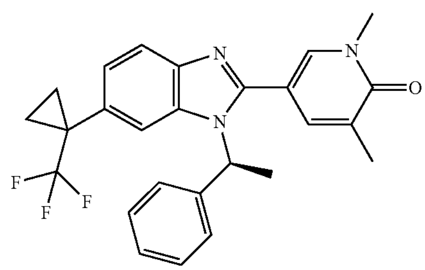 [SMILES: Cc1cc(-c2nc3ccc(C4(C(F)(F)F)CC4)cc3n2[C@@H](C)c2ccccc2)cn(C)c1=O] | M + H = 452; t_Ret. = 1.37 | LCMS BAS1 |
| I-38 | 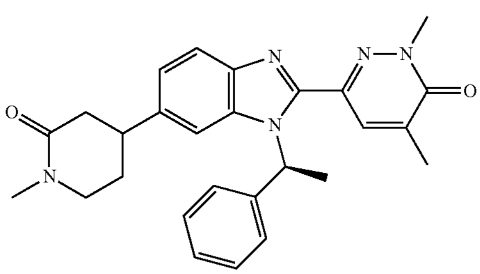 [SMILES: Cc1cc(-c2nc3ccc(C4CCN(C)C(=O)C4)cc3n2[C@@H](C)c2ccccc2)nn(C)c1=O] | M + H = 456; t_Ret. = 1.07 | LCMS BAS1 |
| I-39 | 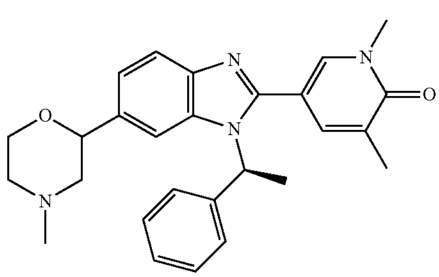 [SMILES: Cc1cc(-c2nc3ccc(C4CN(C)CCO4)cc3n2[C@@H](C)c2ccccc2)cn(C)c1=O] | M + H = 444; t_Ret. = 1.10 | LCMS BAS1 |

General Method For Preparation Of Compounds Of Formula II

Method 1:

5-(1-Benzyl-6-morpholin-4-yl-1H-imidazo[4,5-c]pyridin-2-yl)-1,3-dimethyl-1H-pyridin-2-one II-3

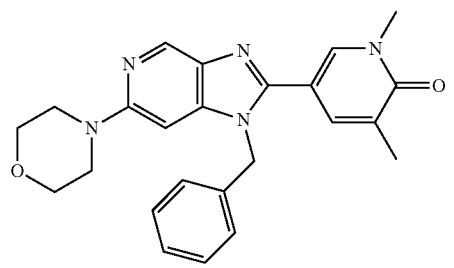

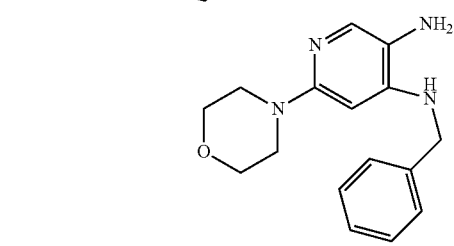

E-2.3

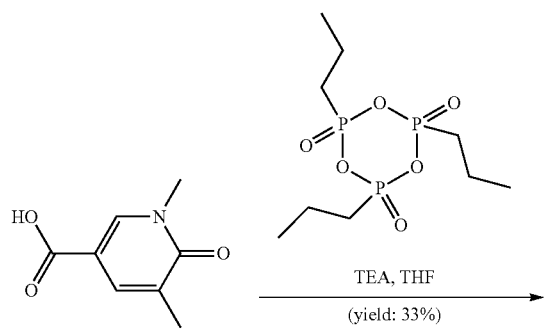

D1

TEA, THF
(yield: 33%)

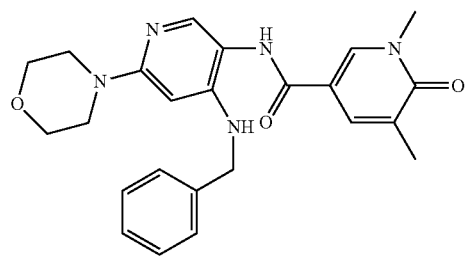 [SMILES: Cc1cc(C(=O)Nc2cnc(N3CCOCC3)cc2NCc2ccccc2)cn(C)c1=O]

II-3'

AcOH
(yield: 92%)

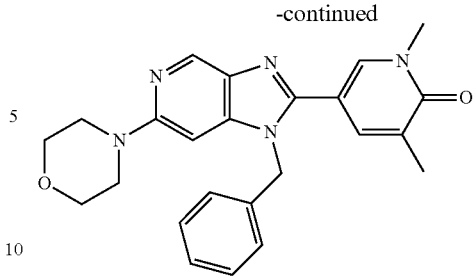

II-3

1,5-Dimethyl-6-oxo-1,6-dihydro-pyridine-3-carboxylic acid (4-benzylamino-6-morpholin-4-yl-pyridin-3-yl)-amide II-3"

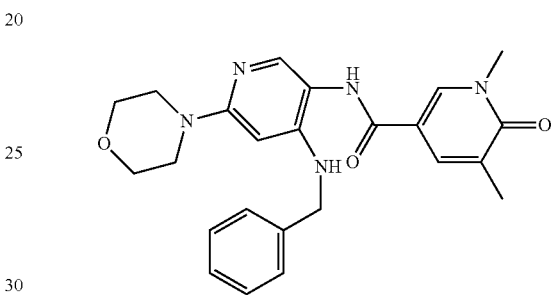

N-Propylphosphonic acid anhydride, cyclic trimer (0.356 ml; 0.610 mmol) is added to a mixture of 1,5-dimethyl-6-oxo-1,6-dihydro-pyridine-3-carboxylic acid D1 (85.000 mg; 0.508 mmol), N4-Benzyl-6-morpholin-4-yl-pyridine-3,4-diamine E-2.3 (133.000 mg; 0.468 mmol) and triethylamine (0.176 ml; 1.271 mmol) in THF (3.000 ml). The reaction mixture is stirred overnight (16 h) at RT. The reaction is quenched with 1M NaOH (2 ml) and diluted with water, then extracted twice with ethyl acetate. The organic layer is dried over $Na_2SO_4$ and concentrated in vacuum. The residue is purified on silica chromatography Combiflash (Column: Redisep Rf, 12 g; gradient: DCM/MeOH=100%/0% to 90%/10%; flow rate=30 ml/min; 28 column volumes; detection wavelength: 254 nm). The product containing fractions are combined and concentrated under reduce pressure.

Yield: 33% (73 mg; 0.168 mmol)

5-(1-Benzyl-6-morpholin-4-yl-1H-imidazo[4,5-c]pyridin-2-yl)-1,3-dimethyl-1H-pyridin-2-one II-3

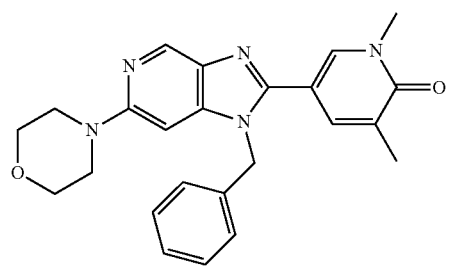 [SMILES: Cc1cc(-c2nc3cnc(N4CCOCC4)cc3n2Cc2ccccc2)cn(C)c1=O]

1,5-Dimethyl-6-oxo-1,6-dihydro-pyridine-3-carboxylic acid (4-benzylamino-6-morpholin-4-yl-pyridin-3-yl)-amide II-3' (73.000 mg; 0.168 mmol) is dissolved in acetic acid (2.1 g) and stirred at 150° C. for 10 h in the microwave. The reaction mixture is concentrated under reduced pressure. The residue is purified on silica chromatography Combiflash (Column: Redisep Rf, 12 g; gradient: DCM/MeOH=100%/0% to 90%/10%; flow rate=30 ml/min; 28 column volumes; detection wavelength: 254 nm). The product containing fractions are combined and concentrated under reduce pressure. The residue is then dissolved in acetonitrile:water 1:1 and freeze dried Yield: 92% (64 mg; 0.154 mmol)

HPLC-MS: (M+H)+=416; $t_{Ret}$=0.95 min; method LCMS BAS1

Method 2:

5-(6-Amino-1-benzyl-1H-imidazo[4,5-c]pyridin-2-yl)-1,3-dimethyl-1H-pyridin-2-one II-16

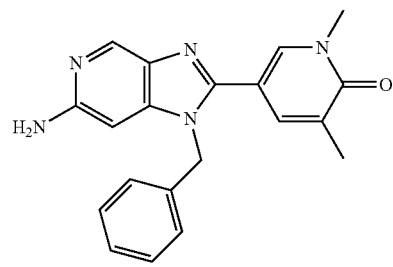

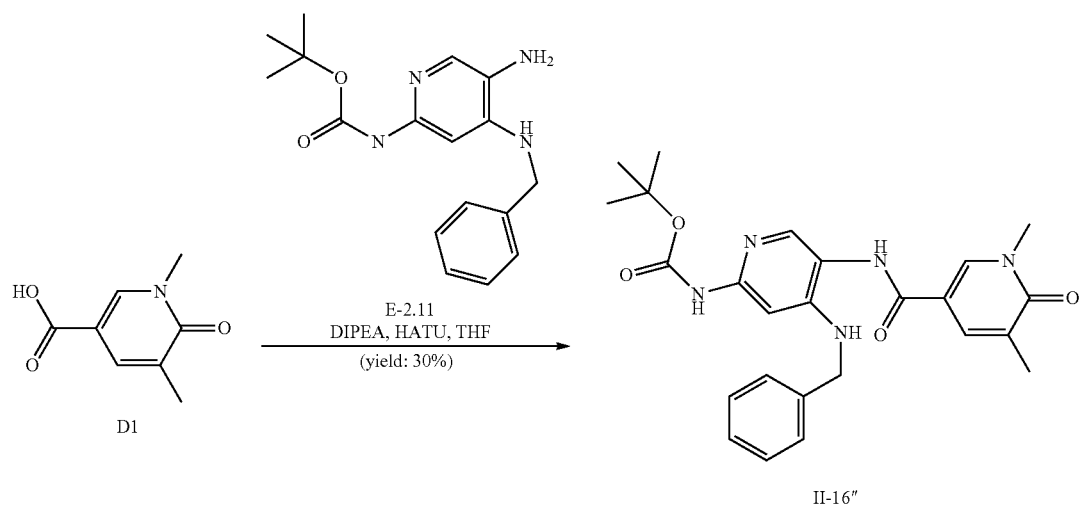

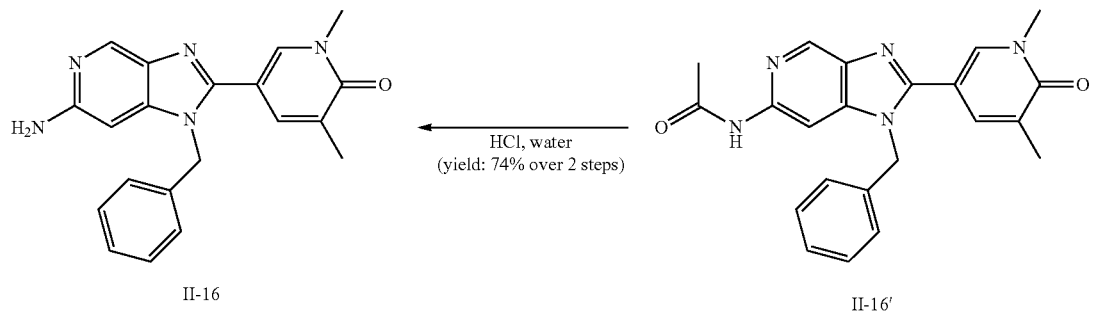

{4-Benzylamino-5-[(1,5-dimethyl-6-oxo-1,6-dihydro-pyridine-3-carbonyl)-amino]-pyridin-2-yl}-carbamic acid tert-butyl ester II-16"

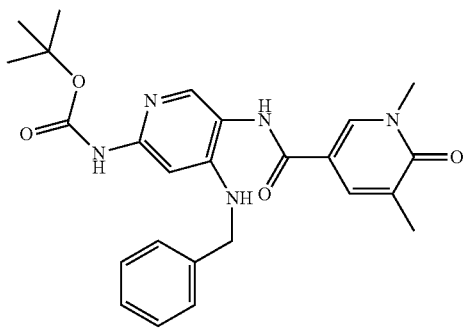 [SMILES: Cc1cc(C(=O)Nc2cnc(NC(=O)OC(C)(C)C)cc2NCc2ccccc2)cn(C)c1=O]

1,5-Dimethyl-6-oxo-1,6-dihydro-pyridine-3-carboxylic acid D1 (3.589 g; 21.47 mmol) and (5-amino-4-benzylamino-pyridin-2-yl)-carbamic acid tert-butyl ester E-2.11 (4.500 g; 14.31 mmol) are dissolved in THF and and cooled to 0° C. DIPEA (5.539 g; 42.94 mmol) and HATU (10.878 g; 28.63 mmol) are added. The mixture is stirred at room temperature for 1 hr. Water is then added to the reaction mixture, precipitation of the product occurs. The precipitate is filtered off and dried under vacuum. The residue is used in the next step without further purification.

Yield: 30% (2.000 g; 4.315 mmol).

N-[1-Benzyl-2-(1,5-dimethyl-6-oxo-1,6-dihydro-pyridin-3-yl)-1H-imidazo[4,5-c]pyridin-6-yl]-acetamide II-16'

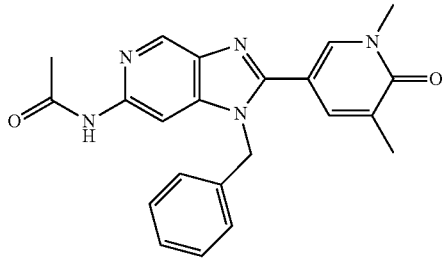 [SMILES: CC(=O)Nc1cc2c(cn1)nc(-c1cc(C)c(=O)n(C)c1)n2Cc1ccccc1]

{4-Benzylamino-5-[(1,5-dimethyl-6-oxo-1,6-dihydro-pyridine-3-carbonyl)-amino]-pyridin-2-yl}-carbamic acid tert-butyl ester II-16" (2.000 g; 4.315 mmol) is suspended in acetic acid (5.190 g; 86 mmol) in a microwave vial and heated in a CEM microwave at 170° C. for 5 h. The reaction mixture is then concentrated under reduced pressure. The residue is used in the next step without further purification.

5-(6-Amino-1-benzyl-1H-imidazo[4,5-c]pyridin-2-yl)-1,3-dimethyl-1H-pyridin-2-one II-16

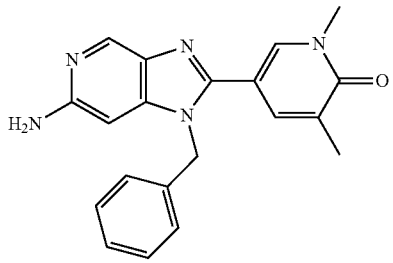 [SMILES: Cc1cc(-c2nc3cnc(N)cc3n2Cc2ccccc2)cn(C)c1=O]

N-[1-Benzyl-2-(1,5-dimethyl-6-oxo-1,6-dihydro-pyridin-3-yl)-1H-imidazo[4,5-c]pyridin-6-yl]-acetamide II-16' (1.67 g; 4.315 mmol) is suspended in 6 N HCl. The reaction mixture is stirred for 1 h at 100° C. The reaction is then cooled to RT and quenched slowly with sodium bicarbonate, precipitation of the product occurs. The product is filtered off and dried under vacuum.

Yield over 2 steps: 74% (1.100 g, 3.185 mmol).

HPLC-MS: (M+H)+=346; $t_{Ret}$=0.81 min; method LCMS BAS1

Method 3:

5-(1-Benzyl-6-imidazol-1-yl-1H-imidazo[4,5-c]pyridin-2-yl)-1,3-dimethyl-1H-pyridin-2-one II-13

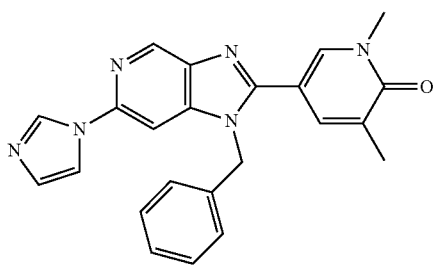

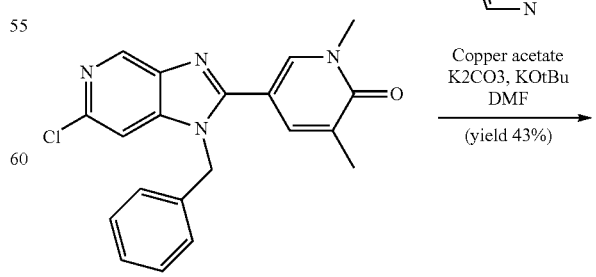

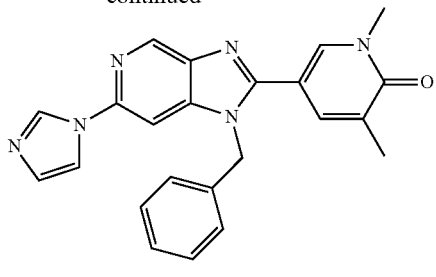

II-13

5-(1-Benzyl-6-chloro-1H-imidazo[4,5-c]pyridin-2-yl)-1,3-dimethyl-1H-pyridin-2-one II-7 (50.000 mg; 0.137 mmol), imidazole (11.196 mg; 0.164 mmol), potassium carbonate (37.884 mg; 0.274 mmol) and copper(II) acetate (33.000 mg; 0.182 mmol) are stirred in N,N-dimethylformamid (0.500 ml) at 120° C. for 48 h. Imidazole (11.196 mg; 0.164 mmol) and potassium tert-butoxide (10.000 mg; 0.089 mmol) are again added and the reaction mixture is stirred at 120° C. for 24 h and then at 150° C. overnight. The catalyst is filtered off and washed with DCM and MeOH. The filtrate is concentrated under reduced pressure and purified on silica chromatography Combiflash (Column: Redisep Rf, 12 g; gradient: DCM/MeOH=100%/0% to 90%/10%; flow rate=30 ml/min; 28 column volumes; detection wavelength: 254 nm). The product containing fractions are combined and concentrated under reduce pressure. The residue is then dissolved in acetonitrile:water 1:1 and freeze-dried Yield: 42% (23 mg; 0.058 mmol)

HPLC-MS: (M+H)+=397; $t_{Ret}$=0.92 min; method LCMS BAS1

Method 4:

Racemic 5-[6-Cyclopropylmethoxy-1-(1-pyridin-2-yl-ethyl)-1H-imidazo[4,5-c]pyridin-2-yl]-1,3-dimethyl-1H-pyridin-2-one II-21

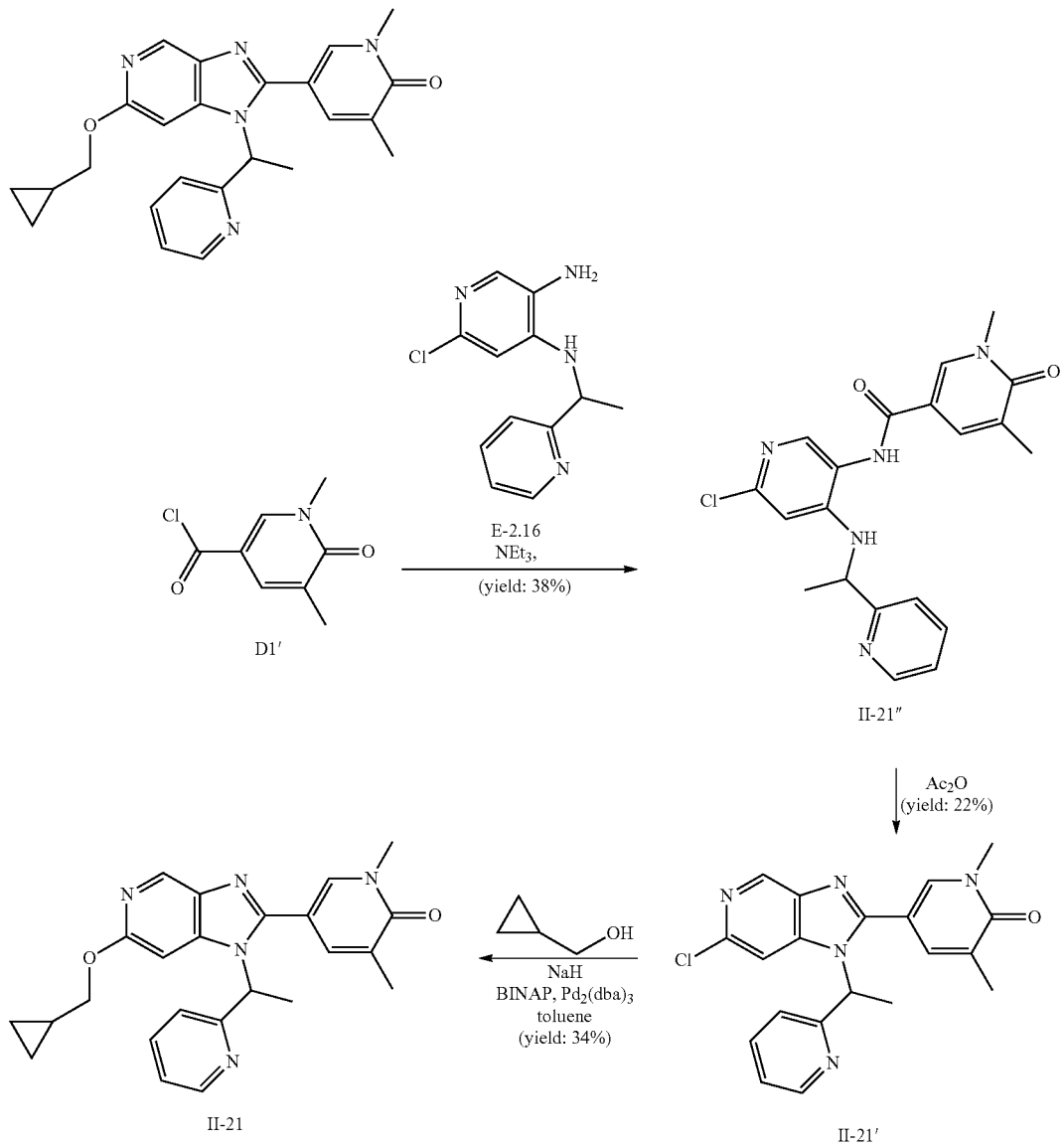

Racemic 1,5-Dimethyl-6-oxo-1,6-dihydro-pyridine-3-carboxylic acid [6-chloro-4-(1-pyridin-2-yl-ethylamino)-pyridin-3-yl]-amide II-21"

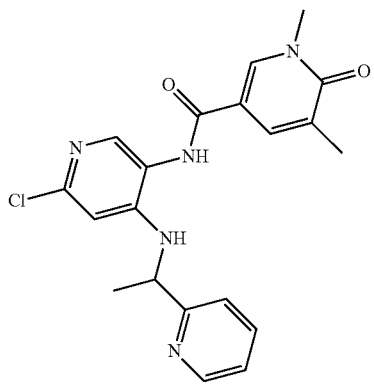 [SMILES: Cc1cc(C(=O)Nc2cnc(Cl)cc2NC(C)c2ccccn2)cn(C)c1=O]

To a solution of racemic 6-chloro-N-4-(1-pyridin-2-yl-ethyl)-pyridine-3,4-diamine E-2.16 (1487 mg; 5.98 mmol) in anhydrous DCM (5 ml) and triethylamine (2.49 ml, 17.94 mmol), 1,5-dimethyl-6-oxo-1,6-dihydro-pyridine-3-carbonyl chloride D1' (1110 mg; 5.98 mmol) dissolved in anhydrous DCM (5 ml) is added dropwise. It is stirred for 1 h. The solvent is removed in vacuo and the residue purified by column chromatography on silica gel. This affords the desired compound.

Yield: 37.9% (902 mg; 2.27 mmol)
HPLC-MS: (M+H)$^+$=398; $t_{Ret.}$=1.72 min; method LCMS BAS1

Racemic 5[6-Chloro-1-(1-pyridin-2-yl-ethyl)-1H-imidazo[4,5-c]pyridin-2-yl]-1,3-dimethyl-1H-pyridin-2-one II-21'

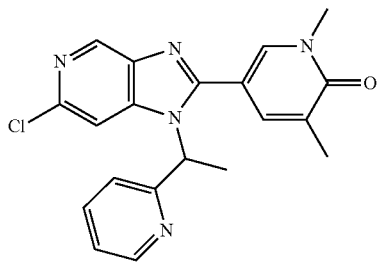 [SMILES: Cc1cc(-c2nc3cnc(Cl)cc3n2C(C)c2ccccn2)cn(C)c1=O]

1,5-Dimethyl-6-oxo-1,6-dihydro-pyridine-3-carboxylic acid [6-chloro-4-(1-pyridin-2-yl-ethylamino)-pyridin-3-yl]-amide II-21" (900 mg; 2.26 mmol) is dissolved in acetic acid (10 ml) and stirred at 150° C. for 1 h in a microwave reactor. The volatiles are removed in vacuo and the residue purified by silica gel chromatography using a DCM/Methanol gradient. The product containing fractions are combined and concentrated under reduced pressure. The product is then lyophilized to afford the desired compound.

Yield: 21.9% (188 mg; 0.49 mmol)
HPLC-MS: (M+H)$^+$=380; $t_{Ret.}$=1.92 min; method LCMS BAS1

Racemic 5-[6-Cyclopropylmethoxy-1-(1-pyridin-2-yl-ethyl)-1H-imidazo[4,5-c]pyridin-2-yl]-1,3-dimethyl-1H-pyridin-2-one II-21

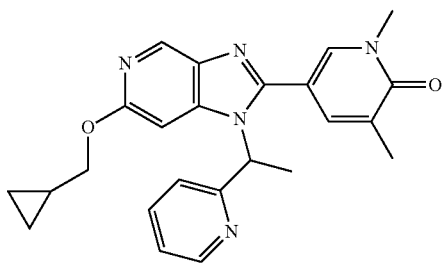 [SMILES: Cc1cc(-c2nc3cnc(OCC4CC4)cc3n2C(C)c2ccccn2)cn(C)c1=O]

Cyclopropyl methanol (7.4 mg; 0.103 mmol) is dissolved in toluene (1 ml) and added to NaH 60% w/w (8.3 mg; 0.348 mmol). The mixture is stirred at 70° C. for 15 min under a nitrogen atmosphere. Then a mixture of (5-[6-Chloro-1-(1-pyridin-2-yl-ethyl)-1H-imidazo[4,5-c]pyridin-2-yl]-1,3-dimethyl-1H-pyridin-2-one II-21' (30 mg; 0.079 mmol), BINAP (9.8 mg; 0.016 mmol), Pd$_2$(dba)$_3$ (7.2 mg; 0.008 mmol) is added in toluene (1 ml) and stirred for 2 hours at 100° C. The reaction mixture is evaporated and dissolved in DMF. The mixture is purified using reversed phase column chromatography (Method: prep. HPLC3). The product containing fractions are lyophilized to afford the desired compound.

Yield: 33.5% (11 mg; 0.03 mmol)
HPLC-MS: (M+H)$^+$=416; $t_{Ret.}$=1.08 min; method LCMS BAS1

According to II-3, II-13, II-16 and II-21 the following examples are synthesized.

| # | Structure | MS (M + H)$^+$; $t_{Ret.}$ HPLC [min] | HPLC-Method |
|---|---|---|---|
| II-1 | 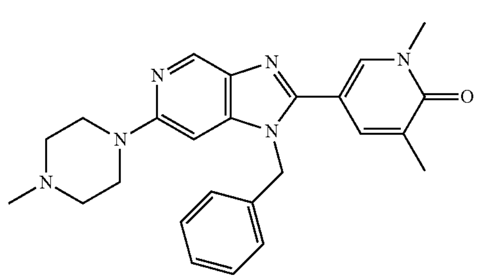 | M + H = 429; $t_{Ret.}$ = 0.95 | LCMS BAS1 |

-continued

| # | Structure | MS (M + H)+; t_Ret. HPLC [min] | HPLC-Method |
|---|---|---|---|
| II-2 | 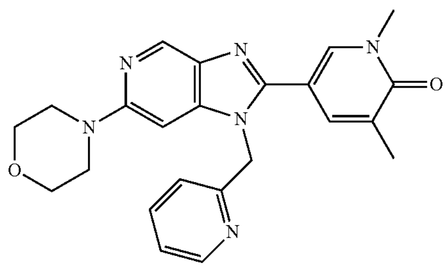 | M + H = 417; t_Ret. = 0.80 | LCMS BAS1 |
| II-3 | 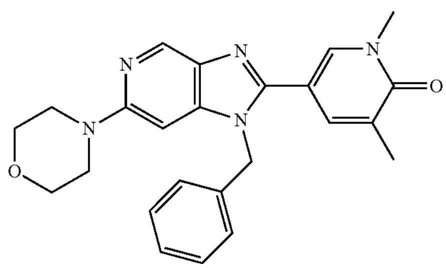 | M + H = 416; t_Ret. = 0.95 | LCMS BAS1 |
| II-4 | 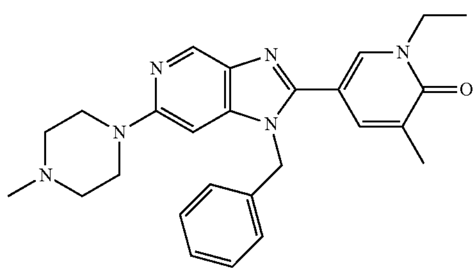 [SMILES: CCn1cc(-c2nc3cnc(N4CCN(C)CC4)cc3n2Cc2ccccc2)cc(C)c1=O] | M + H = 443; t_Ret. = 1.02 | LCMS BAS1 |
| II-5 | 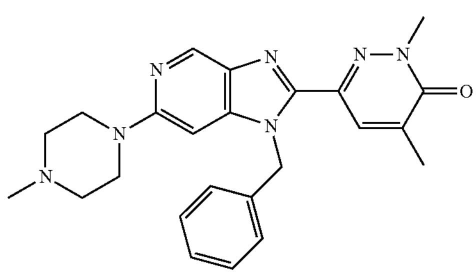 [SMILES: Cc1cc(-c2nc3cnc(N4CCN(C)CC4)cc3n2Cc2ccccc2)nn(C)c1=O] | M + H = 430; t_Ret. = 1.07 | LCMS BAS1 |
| II-6 | 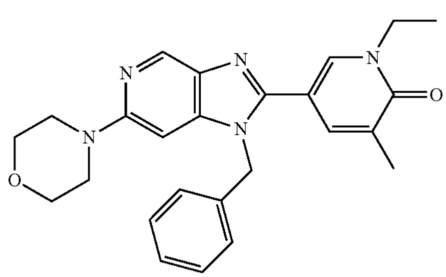 [SMILES: CCn1cc(-c2nc3cnc(N4CCOCC4)cc3n2Cc2ccccc2)cc(C)c1=O] | M + H = 430; t_Ret. = 1.03 | LCMS BAS1 |

-continued

| # | Structure | MS (M + H)+; t_Ret. HPLC [min] | HPLC-Method |
|---|---|---|---|
| II-7 | 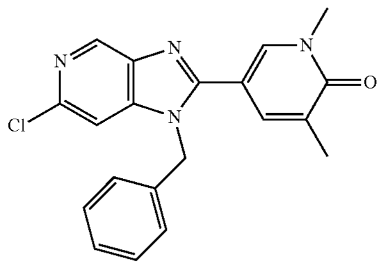 [SMILES: Cc1cc(-c2nc3cnc(Cl)cc3n2Cc2ccccc2)cn(C)c1=O] | M + H = 365; t_Ret. = 1.03 | LCMS BAS1 |
| II-8 | 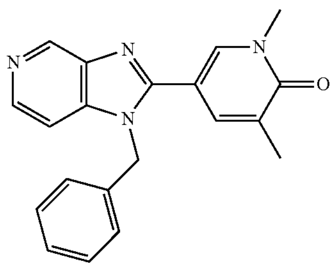 [SMILES: Cc1cc(-c2nc3cnccc3n2Cc2ccccc2)cn(C)c1=O] | M + H = 331; t_Ret. = 0.87 | LCMS BAS1 |
| II-9 | 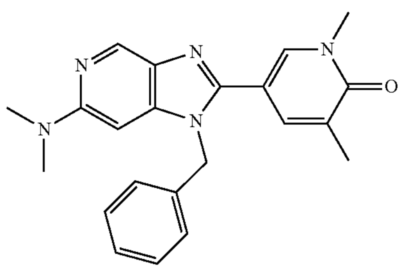 [SMILES: Cc1cc(-c2nc3cnc(N(C)C)cc3n2Cc2ccccc2)cn(C)c1=O] | M + H = 374; t_Ret. = 1.04 | LCMS BAS1 |
| II-10 | 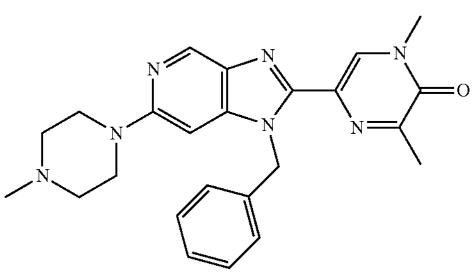 [SMILES: Cc1nc(-c2nc3cnc(N4CCN(C)CC4)cc3n2Cc2ccccc2)cn(C)c1=O] | M + H = 430; t_Ret. = 1.02 | LCMS BAS1 |
| II-11 | 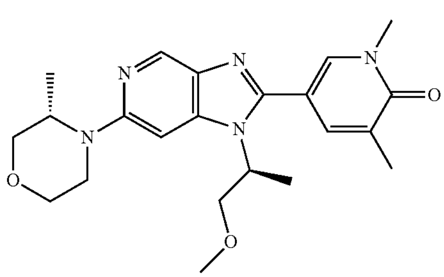 | M + H = 412; t_Ret. = 0.91 | LCMS BAS1 |

-continued
| # | Structure | MS (M + H)+; t_Ret. HPLC [min] | HPLC-Method |
|---|---|---|---|
| II-12 | 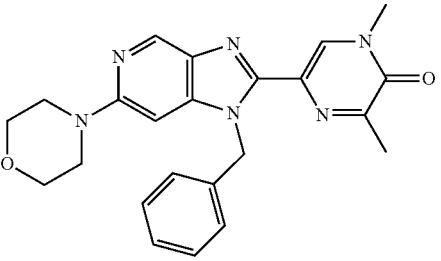 | M + H = 417; t_Ret. = 1.03 | LCMS BAS1 |
| II-13 | 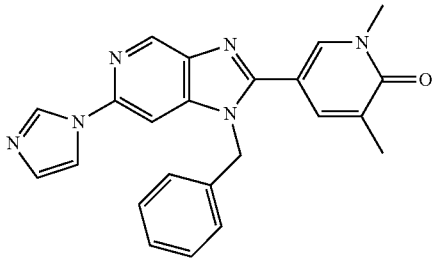 [SMILES: Cc1cc(-c2nc3cnc(-n4ccnc4)cc3n2Cc2ccccc2)cn(C)c1=O] | M + H = 397; t_Ret. = 0.92 | LCMS BAS1 |
| II-14 | 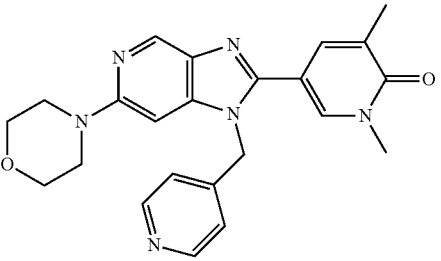 [SMILES: Cc1cc(-c2nc3cnc(N4CCOCC4)cc3n2Cc2ccncc2)cn(C)c1=O] | M + H = 417; t_Ret. = 0.75 | LCMS BAS1 |
| II-15 | Chiral 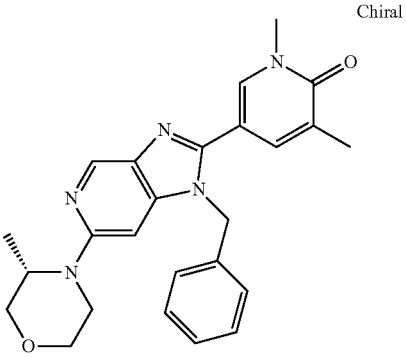 [SMILES: Cc1cc(-c2nc3cnc(N4CCOC[C@@H]4C)cc3n2Cc2ccccc2)cn(C)c1=O] | M + H = 430; t_Ret. = 1.03 | LCMS BAS1 |
| II-16 | 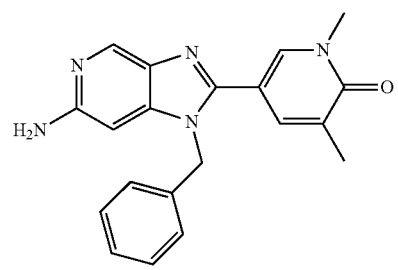 | M + H = 346; t_Ret. = 0.81 | LCMS BAS1 |

| # | Structure | MS (M + H)+; t_Ret. HPLC [min] | HPLC-Method |
|---|---|---|---|
| II-17 | 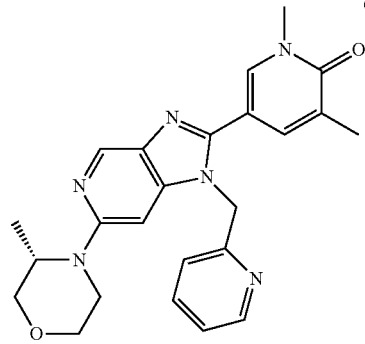 Chiral | M + H = 431; t_Ret. = 0.88 | LCMS BAS1 |
| II-18 | 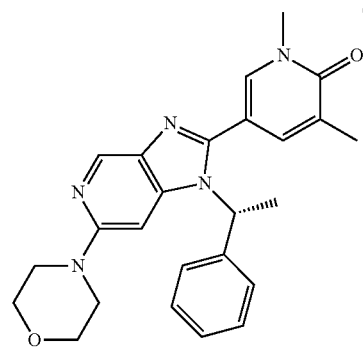 Chiral | M + H = 430; t_Ret. = 1.01 | LCMS BAS1 |
| II-19 | 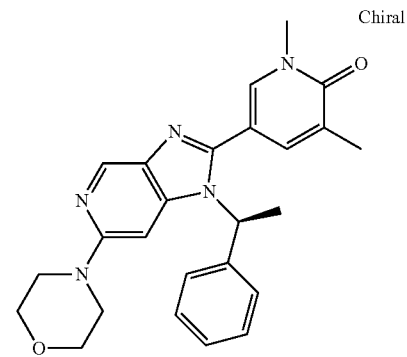 [SMILES: Cc1cc(-c2nc3cnc(N4CCOCC4)cc3n2[C@@H](C)c2ccccc2)cn(C)c1=O] Chiral | M + H = 430; t_Ret. = 1.01 | LCMS BAS1 |
| II-20 | 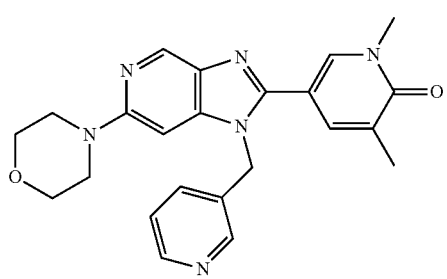 [SMILES: Cc1cc(-c2nc3cnc(N4CCOCC4)cc3n2Cc2cccnc2)cn(C)c1=O] | M + H = 417; t_Ret. = 0.77 | LCMS BAS1 |

-continued

| # | Structure | MS (M + H)+; t_Ret. HPLC [min] | HPLC-Method |
|---|---|---|---|
| II-21 | 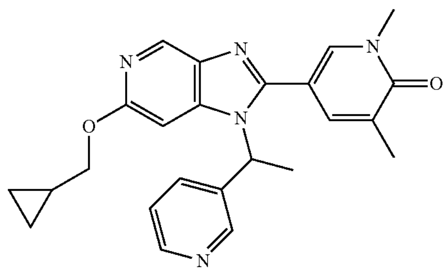 [SMILES: Cc1cc(-c2nc3cnc(OCC4CC4)cc3n2C(C)c2cccnc2)cn(C)c1=O] | M + H = 416; t_Ret. = 1.08 | LCMS BAS1 |
| II-22 | 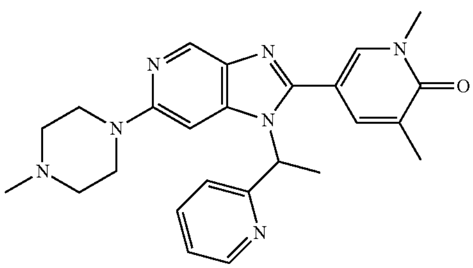 [SMILES: Cc1cc(-c2nc3cnc(N4CCN(C)CC4)cc3n2C(C)c2ccccn2)cn(C)c1=O] | M + H = 444; t_Ret. = 0.87 | LCMS BAS1 |
| II-23 | 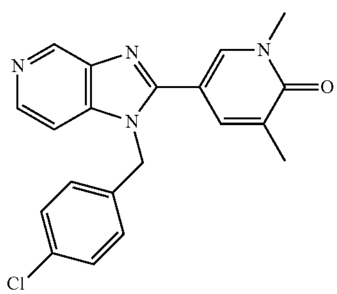 [SMILES: Cc1cc(-c2nc3cnccc3n2Cc2ccc(Cl)cc2)cn(C)c1=O] | M + H = 365; t_Ret. = 0.98 | LCMS BAS1 |
| II-24 | Chiral | M + H = 387; t_Ret. = 1.09 | LCMS BAS1 |
| II-25 | 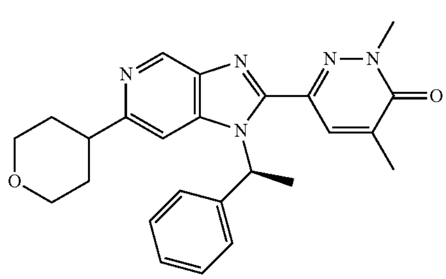 | M + H = 430; t_Ret. = 1.10 | LCMS BAS1 |

-continued

| # | Structure | MS (M + H)+; t_Ret. HPLC [min] | HPLC-Method |
|---|---|---|---|
| II-26 | 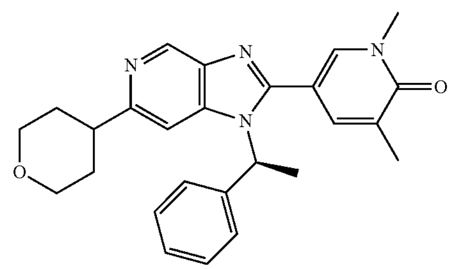 | M + H = 429; t_Ret. = 1.02 | LCMS BAS1 |
| II-27 | 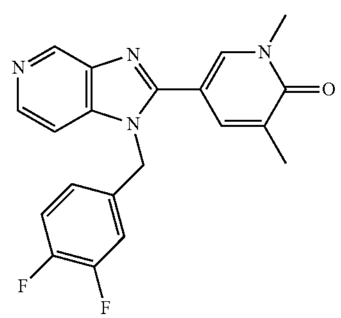 [SMILES: Cc1cc(-c2nc3cnccc3n2Cc2ccc(F)c(F)c2)cn(C)c1=O] | M + H = 367; t_Ret. = 0.93 | LCMS BAS1 |
| II-28 | 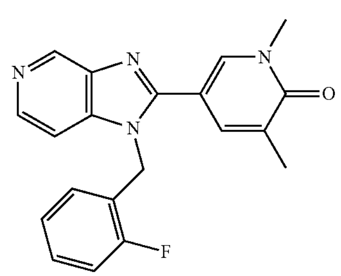 [SMILES: Cc1cc(-c2nc3cnccc3n2Cc2ccccc2F)cn(C)c1=O] | M + H = 349; t_Ret. = 0.89 | LCMS BAS1 |
| II-29 | 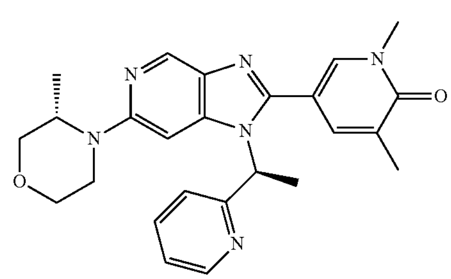 [SMILES: Cc1cc(-c2nc3cnc(N4CCOC[C@@H]4C)cc3n2[C@@H](C)c2ccccn2)cn(C)c1=O] | M + H = 445; t_Ret. = 0.94 | LCMS BAS1 |
| II-30 | 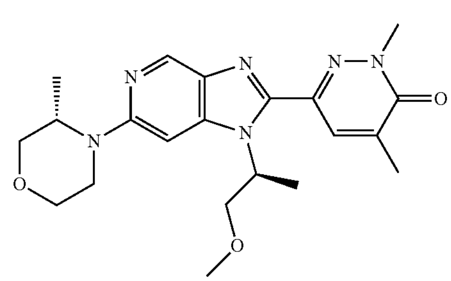 | M + H = 413; t_Ret. = 1.00 | LCMS BAS1 |

| # | Structure | MS (M + H)+; t$_{Ret.}$ HPLC [min] | HPLC-Method |
|---|---|---|---|
| II-31 | 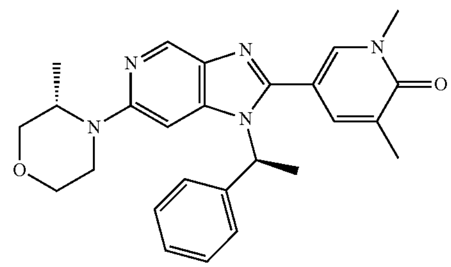 | M + H = 444; t$_{Ret.}$ = 1.08 | LCMS BAS1 |
| II-32 | 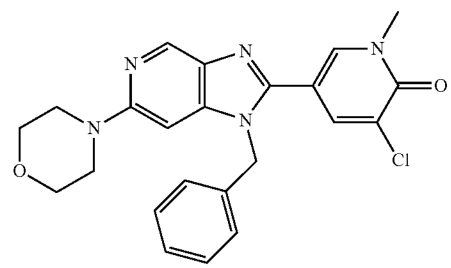 | M + H = 436; t$_{Ret.}$ = 1.02 | LCMS BAS1 |
| II-33 | 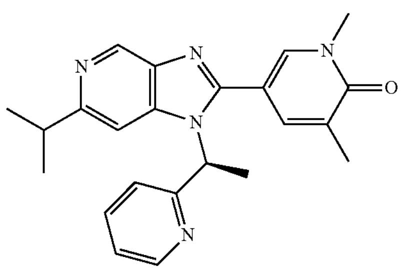 [SMILES: Cc1cc(-c2nc3cnc(C(C)C)cc3n2[C@@H](C)c2ccccn2)cn(C)c1=O] | M + H = 388; t$_{Ret.}$ = 1.02 | LCMS BAS1 |
| II-34 | 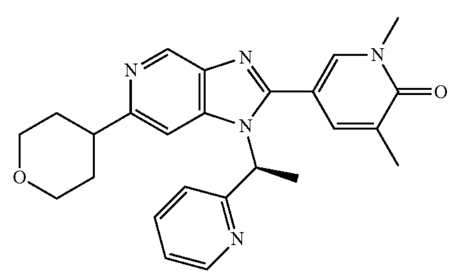 | M + H = 430; t$_{Ret.}$ = 0.89 | LCMS BAS1 |
| II-35 | 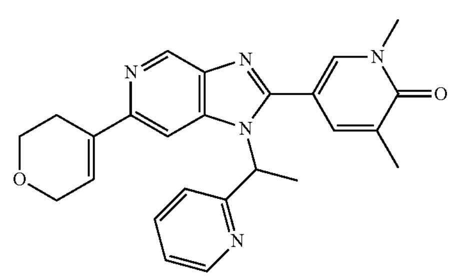 [SMILES: Cc1cc(-c2nc3cnc(C4=CCOCC4)cc3n2C(C)c2ccccn2)cn(C)c1=O] | M + H = 428; t$_{Ret.}$ = 0.92 | LCMS BAS1 |

-continued

| # | Structure | MS (M + H)+; t_Ret. HPLC [min] | HPLC-Method |
|---|---|---|---|
| II-36 | 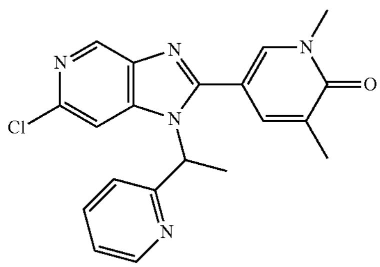 [SMILES: Cc1cc(-c2nc3cnc(Cl)cc3n2C(C)c2ccccn2)cn(C)c1=O] | M + H = 380; t_Ret. = 0.94 | LCMS BAS1 |
| II-37 | 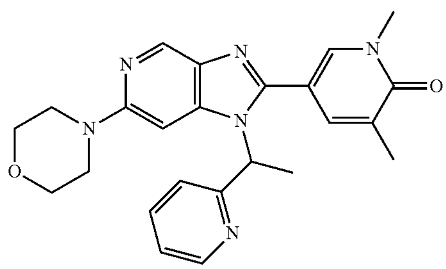 [SMILES: Cc1cc(-c2nc3cnc(N4CCOCC4)cc3n2C(C)c2ccccn2)cn(C)c1=O] | M + H = 431; t_Ret. = 0.88 | LCMS BAS1 |
| II-38 | 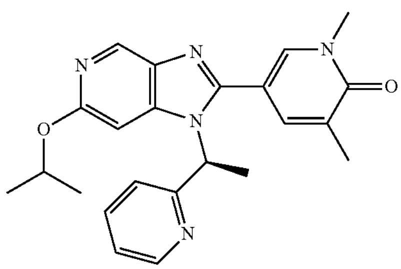 [SMILES: Cc1cc(-c2nc3cnc(OC(C)C)cc3n2[C@@H](C)c2ccccn2)cn(C)c1=O] | M + H = 404; t_Ret. = 1.06 | LCMS BAS1 |
| II-39 | 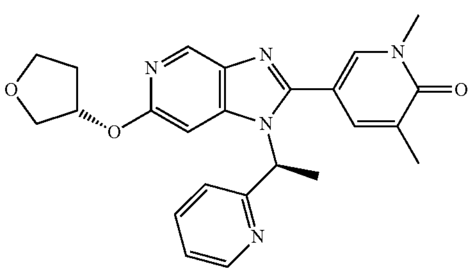 | M + H = 432; t_Ret. = 1.07 | LCMS BAS1 |
| II-40 | 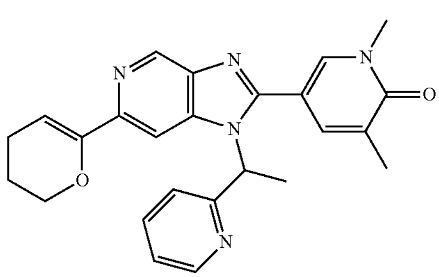 [SMILES: Cc1cc(-c2nc3cnc(C4=CCCCO4)cc3n2C(C)c2ccccn2)cn(C)c1=O] | M + H = 428; t_Ret. = 1.06 | LCMS BAS1 |

-continued

| # | Structure | MS (M + H)+; t_Ret. HPLC [min] | HPLC-Method |
|---|---|---|---|
| II-41 | 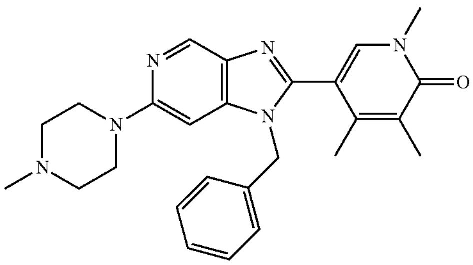 [SMILES: Cc1c(-c2nc3cnc(N4CCN(C)CC4)cc3n2Cc2ccccc2)cn(C)c(=O)c1C] | M + H = 443; t_Ret. = 0.98 | LCMS BAS1 |
| II-42 | 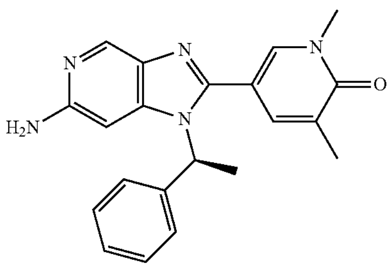 [SMILES: Cc1cc(-c2nc3cnc(N)cc3n2[C@@H](C)c2ccccc2)cn(C)c1=O] | M + H = 360; t_Ret. = 0.86 | LCMS BAS1 |
| II-43 | 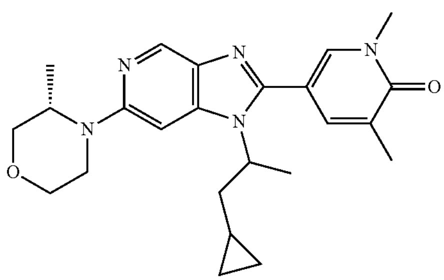 [SMILES: Cc1cc(-c2nc3cnc(N4CCOC[C@@H]4C)cc3n2C(C)CC2CC2)cn(C)c1=O] | M + H = 422; t_Ret. = 1.06 | LCMS BAS1 |
| II-44 | 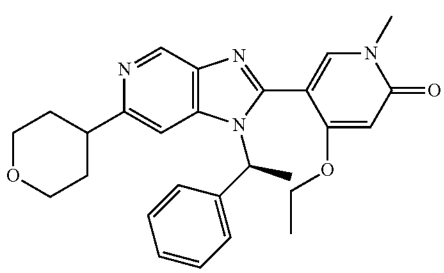 [SMILES: CCOc1cc(=O)n(C)cc1-c1nc2cnc(C3CCOCC3)cc2n1[C@@H](C)c1ccccc1] | M + H = 459; t_Ret. = 1.02 | LCMS BAS1 |
| II-45 | 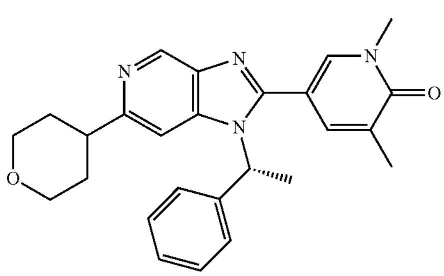 [SMILES: Cc1cc(-c2nc3cnc(C4CCOCC4)cc3n2[C@H](C)c2ccccc2)cn(C)c1=O] | M + H = 429; t_Ret. = 1.02 | LCMS BAS1 |

General Method for Preparation of Compounds of Formula III

5-[3-Benzyl-5-(4-methyl-piperazin-1-yl)-3H-imidazo[4,5-b]pyridin-2-yl]-1-methyl-1H-pyridin-2-one III-1

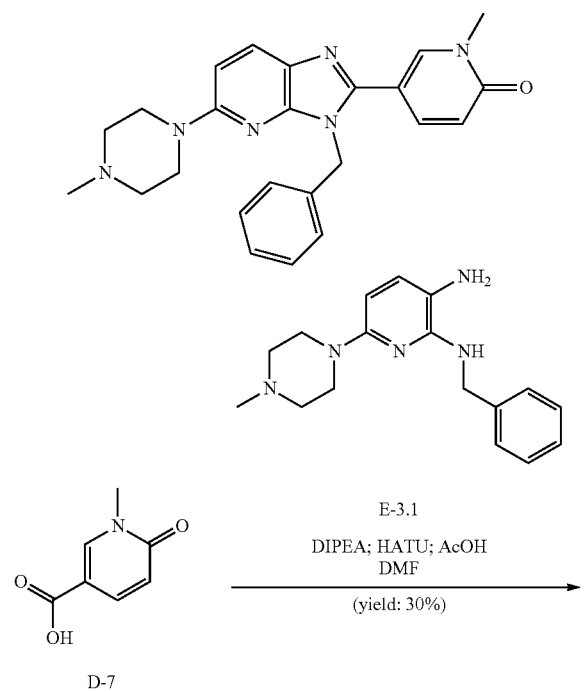

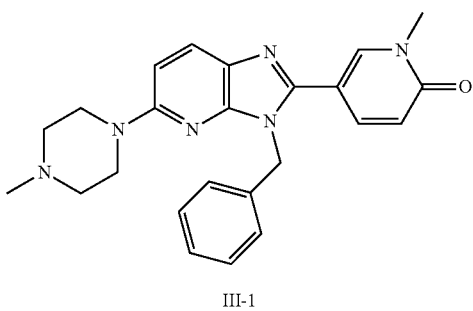

III-1

DIPEA (51 mg; 0.392 mmol) is added to a suspension of 1-methyl-6-oxo-1,6-dihydro-pyridine-3-carboxylic acid D-7 (20 mg; 0.131 mmol) and HATU (70 mg; 0.183 mg) in DMF. The mixture is stirred at RT for 5 min. N2-Benzyl-6-(4-methyl-piperazin-1-yl)-pyridine-2,3-diamine E-3.1 is then added and the reaction mixture stirred at RT for 1 h. The reaction mixture is extracted with DCM and NaHCO$_3$ solution. The organic layer is dried over Na$_2$SO$_4$ and concentrated in vacuum. To the formed amide is added 1 ml glacial acetic acid, the reaction is stirred at 120° C. for 2 days. The crude reaction mixture is purified by using reversed phase chromatography (Method: prep. HPLC1).

Yield: 30% (16 mg; 0.039 mmol)

HPLC-MS: (M+H)$^+$=415; t$_{Ret.}$=1.01 min; method LCMS BAS1

According to III-1, the following examples are synthesized.

| # | Structure | MS (M + H)$^+$; t$_{Ret.}$ HPLC [min] | HPLC-Method |
|---|-----------|---------------------------------------|-------------|
| III-1 | 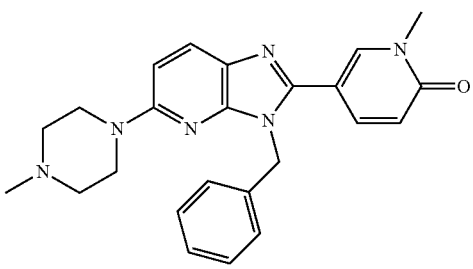 [SMILES: CN1CCN(c2ccc3nc(-c4ccc(=O)n(C)c4)n(Cc4ccccc4)c3n2)CC1] | M + H = 415; t$_{Ret.}$ = 1.01 | LCMS BAS1 |
| III-2 | 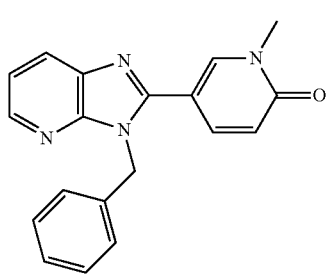 [SMILES: Cn1cc(-c2nc3cccnc3n2Cc2ccccc2)ccc1=O] | M + H = 317; t$_{Ret.}$ = 0.91 | LCMS BAS1 |

-continued
| # | Structure | MS (M + H)+; t_Ret. HPLC [min] | HPLC-Method |
|---|---|---|---|
| III-3 | 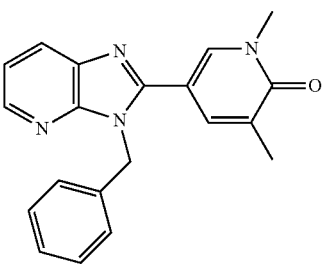 [SMILES: Cc1cc(-c2nc3cccnc3n2Cc2ccccc2)cn(C)c1=O] | M + H = 331; t_Ret. = 0.99 | LCMS BAS1 |
| III-4 | 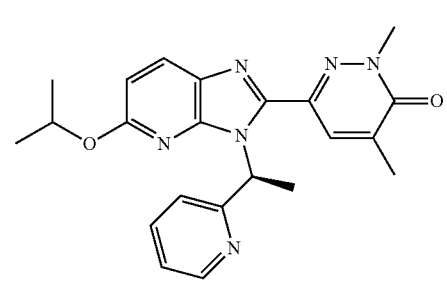 [SMILES: Cc1cc(-c2nc3ccc(OC(C)C)nc3n2[C@@H](C)c2ccccn2)nn(C)c1=O] | M + H = 405; t_Ret. = 1.27 | LCMS BAS1 |
| III-5 | 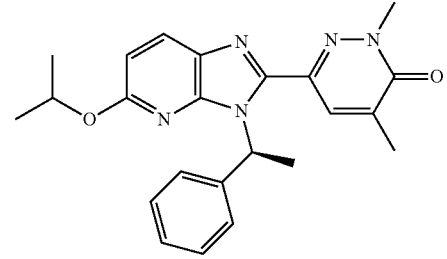 [SMILES: Cc1cc(-c2nc3ccc(OC(C)C)nc3n2[C@@H](C)c2ccccc2)nn(C)c1=O] | M + H = 404; t_Ret. = 1.46 | LCMS BAS1 |
| III-6 | 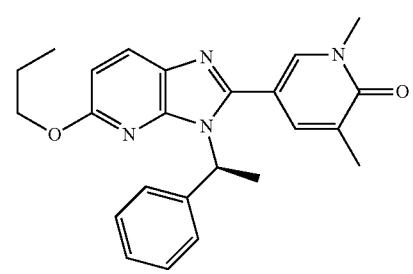 [SMILES: CCCOc1ccc2nc(-c3cc(C)c(=O)n(C)c3)n([C@@H](C)c3ccccc3)c2n1] | M + H = 403; t_Ret. = 1.37 | LCMS BAS1 |
| III-7 | 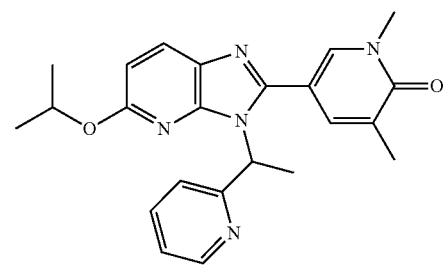 [SMILES: Cc1cc(-c2nc3ccc(OC(C)C)nc3n2C(C)c2ccccn2)cn(C)c1=O] | M + H = 404; t_Ret. = 1.19 | LCMS BAS1 |

-continued

| # | Structure | MS (M + H)⁺; $t_{Ret.}$ HPLC [min] | HPLC-Method |
|---|---|---|---|
| III-8 | 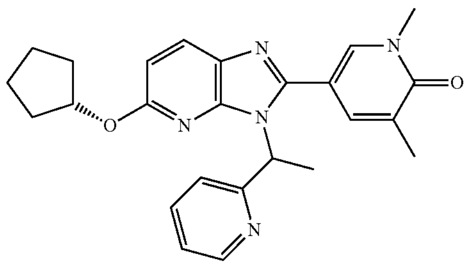 | M + H = 432; $t_{Ret.}$ = 1.00 | LCMS BAS1 |
| III-9 | 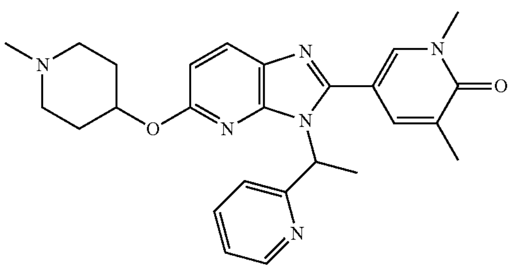 [SMILES: Cc1cc(-c2nc3ccc(OC4CCN(C)CC4)nc3n2C(C)c2ccccn2)cn(C)c1=O] | M + H = 459; $t_{Ret.}$ = 1.03 | LCMS BAS1 |

Preparation of Compounds of Formula IV

According to I-1, I-9, I-12, II-3, II-13 and III-1 the following examples are synthesized.

| # | Structure | MS (M + H)⁺; $t_{Ret.}$ HPLC [min] | HPLC-Method |
|---|---|---|---|
| IV-1 | 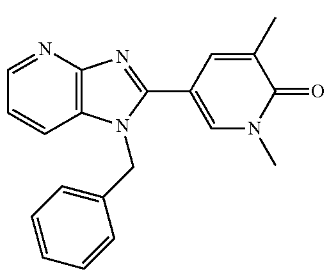 [SMILES: Cc1cc(-c2nc3ncccc3n2Cc2ccccc2)cn(C)c1=O] | M + H = 331; $t_{Ret.}$ = 0.92 | LCMS BAS1 |
| IV-2 | 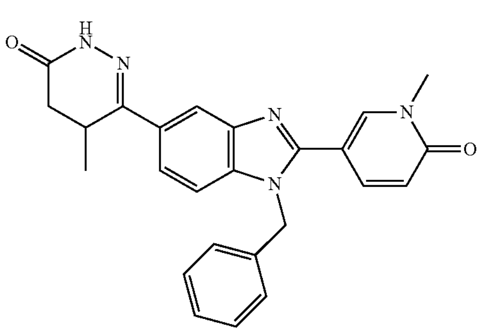 [SMILES: CC1CC(=O)NN=C1c1ccc2c(c1)nc(-c1ccc(=O)n(C)c1)n2Cc1ccccc1] | M + H = 426; tRet. = 0.91 | LCMS BAS1 |

-continued

| # | Structure | MS (M + H)+; t_Ret. HPLC [min] | HPLC-Method |
|---|---|---|---|
| IV-3 | 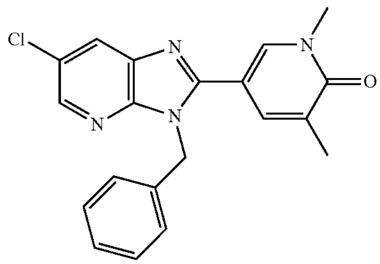 [SMILES: Cc1cc(-c2nc3cc(Cl)cnc3n2Cc2ccccc2)cn(C)c1=O] | M + H = 365; t_Ret. = 1.19 | LCMS BAS1 |
| IV-4 | 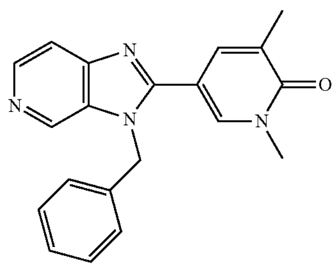 [SMILES: Cc1cc(-c2nc3ccncc3n2Cc2ccccc2)cn(C)c1=O] | M + H = 331; tRet. = 0.86 | LCMS BAS1 |
| IV-5 | 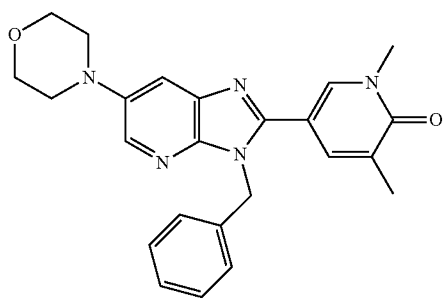 [SMILES: Cc1cc(-c2nc3cc(N4CCOCC4)cnc3n2Cc2ccccc2)cn(C)c1=O] | M + H = 416; tRet. = 1.03 | LCMS BAS1 |
| IV-6 | 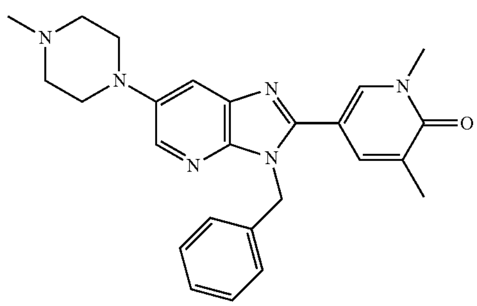 [SMILES: Cc1cc(-c2nc3cc(N4CCN(C)CC4)cnc3n2Cc2ccccc2)cn(C)c1=O] | M + H = 429; tRet. = 1.01 | LCMS BAS1 |
| IV-7 | 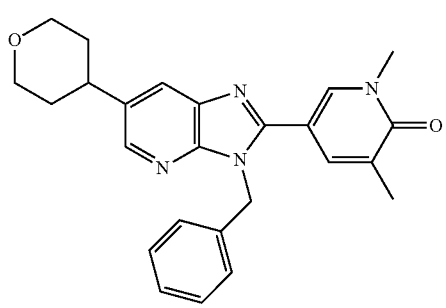 [SMILES: Cc1cc(-c2nc3cc(C4CCOCC4)cnc3n2Cc2ccccc2)cn(C)c1=O] | M + H = 415; tRet. = 1.07 | LCMS BAS1 |

| # | Structure | MS (M + H)+; t_Ret. HPLC [min] | HPLC-Method |
|---|---|---|---|
| IV-8 | 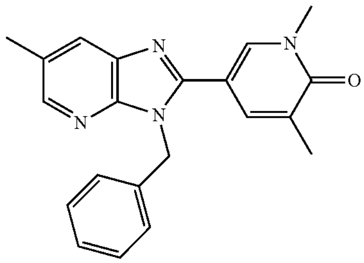 [SMILES: Cc1cnc2c(c1)nc(-c1cc(C)c(=O)n(C)c1)n2Cc1ccccc1] | M + H = 345; tRet. = 1.06 | LCMS BAS1 |
| IV-9 | 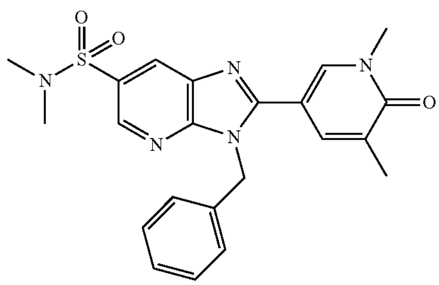 [SMILES: Cc1cc(-c2nc3cc(S(=O)(=O)N(C)C)cnc3n2Cc2ccccc2)cn(C)c1=O] | M + H = 438; tRet. = 0.96 | LCMS BAS1 |
| IV-10 | 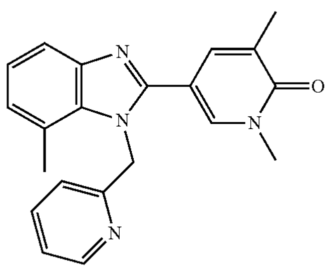 [SMILES: Cc1cc(-c2nc3cccc(C)c3n2Cc2ccccn2)cn(C)c1=O] | M + H = 345; tRet. = 0.97 | LCMS BAS1 |
| IV-11 | 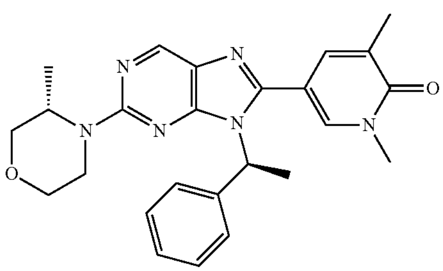 [SMILES: Cc1cc(-c2nc3cnc(N4CCOC[C@@H]4C)nc3n2[C@@H](C)c2ccccc2)cn(C)c1=O] | M + H = 445; tRet. = 1.17 | LCMS BAS1 |
| IV-12 | 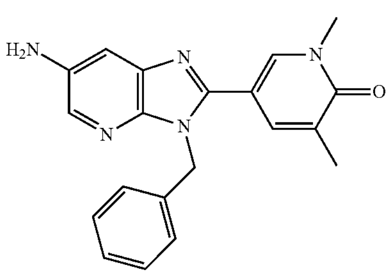 [SMILES: Cc1cc(-c2nc3cc(N)cnc3n2Cc2ccccc2)cn(C)c1=O] | M + H = 346; tRet. = 0.85 | LCMS BAS1 |

-continued
| # | Structure | MS (M + H)+; t_Ret. HPLC [min] | HPLC-Method |
|---|---|---|---|
| IV-13 | 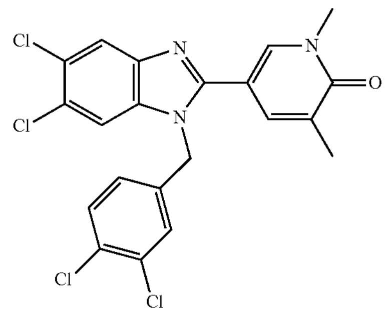 [SMILES: Cc1cc(-c2nc3cc(Cl)c(Cl)cc3n2Cc2ccc(Cl)c(Cl)c2)cn(C)c1=O] | M + H = 466; tRet. = 1.45 | LCMS BAS1 |
| IV-14 | 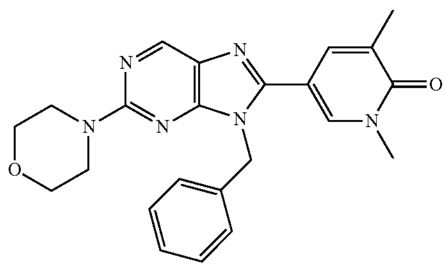 [SMILES: Cc1cc(-c2nc3cnc(N4CCOCC4)nc3n2Cc2ccccc2)cn(C)c1=O] | M + H = 417; tRet. = 1.07 | LCMS BAS1 |
| IV-15 | 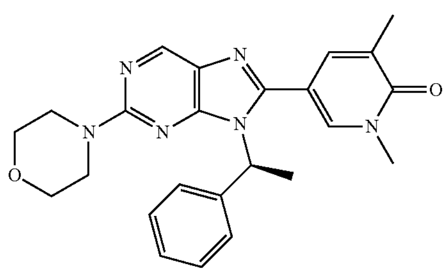 [SMILES: Cc1cc(-c2nc3cnc(N4CCOCC4)nc3n2[C@@H](C)c2ccccc2)cn(C)c1=O] | M + H = 431; tRet. = 1.11 | LCMS BAS1 |
General Method for Preparation of Compounds of Formula V and VI
6-[2-(5-amino-1-methyl-6-oxo-1,6-dihydropyridin-3-yl)-1-benzyl-1H-1,3-benzodiazol-5-yl]-5-methyl-2,3,4,5-tetrahydropyridazin-3-one V-1
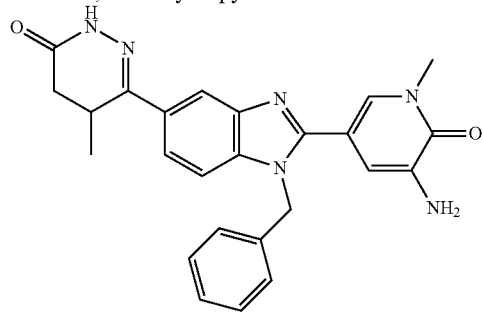
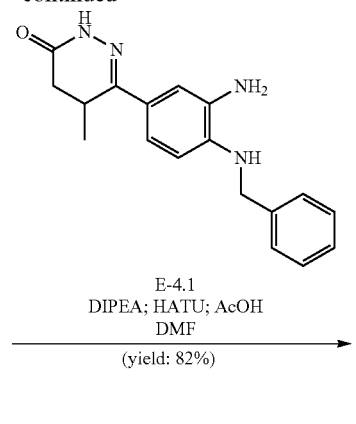
E-4.1
DIPEA; HATU; AcOH
DMF
(yield: 82%)

-continued

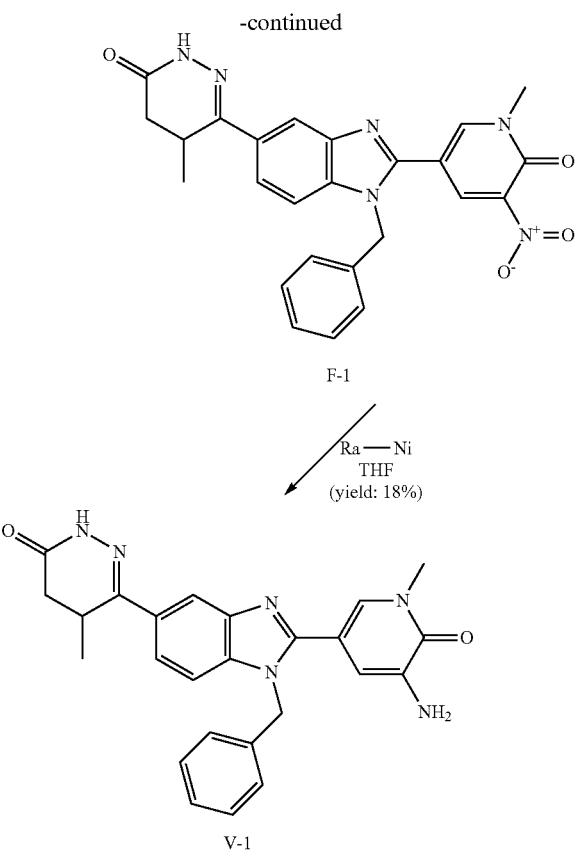

F-1

6-[1-Benzyl-2-(1-methyl-5-nitro-6-oxo-1,6-dihydro-pyridin-3-yl)-1H-benzoimidazol-5-yl]-5-methyl-4,5-dihydro-2H-pyridazin-3-one F-1

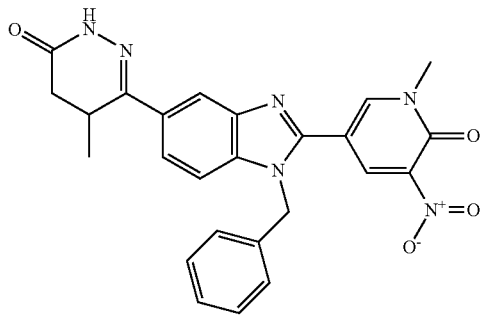 [SMILES: CC1CC(=O)NN=C1c1ccc2c(c1)nc(-c1cc([N+](=O)[O-])c(=O)n(C)c1)n2Cc1ccccc1]

1-Methyl-5-nitro-6-oxo-1,6-dihydro-pyridine-3-carboxylic acid D-8 (50 mg; 0.25 mmol) is dissolved in 1 ml DMF. DIPEA (0.12 ml; 0.76 mmol) and HATU (106 mg; 0.28 mmol) are added. After 5 minutes at room temperature intermediate E-4.1 (100 mg; 0.28 mmol) is added and the reaction mixture is stirred for 1 hour. To the formed amide is added 1 ml glacial acetic acid. The reaction is heated up to 100° C. for 16 hours. The crude reaction mixture is purified by using reversed phase chromatography (Method: prep. HPLC1).

Yield: 82% (97 mg; 0.21 mmol)

HPLC-MS: $(M+H)^+=471$; $t_{Ret}=0.76$ min; method VAB

6-[2-(5-Amino-1-methyl-6-oxo-1,6-dihydro-pyridin-3-yl)-1-benzyl-1H-benzoimidazol-5-yl]-5-methyl-4,5-dihydro-2H-pyridazin-3-one V-1

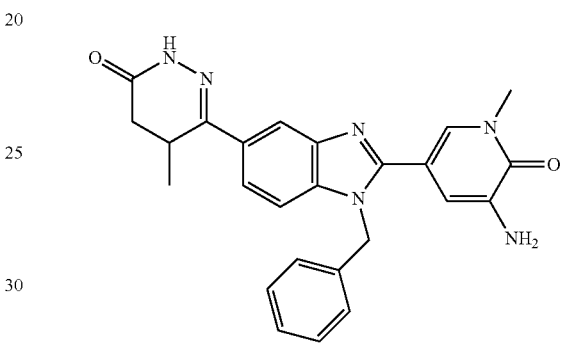

In a hydrogenation apparatus is placed 6-[1-benzyl-2-(1-methyl-5-nitro-6-oxo-1,6-dihydro-pyridin-3-yl)-1H-benzoimidazol-5-yl]-5-methyl-4,5-dihydro-2H-pyridazin-3-one F-1 (97 mg; 0.21 mmol) dissolved in 50 ml THF. A scoop of Raney-Nickel is added and the reactor filled up with $H_2$ to 5 bar. The reaction mixture is stirred at room temperature for 1 hour. The Raney-Nickel is filtered off and the filtrate concentrated under reduced pressure. The residue is purified by using reversed phase chromatography (Method: prep. HPLC1).

Yield: 18% (16 mg; 0.04 mmol)

HPLC-MS: $(M+H)^+=441$; $t_{Ret}=0.92$ min; method LCMS BAS1

According V-1 the following examples are synthesized.

| # | Structure | MS (M + H)$^+$; $t_{Ret.}$ HPLC [min] | HPLC-Method |
|---|-----------|--------------------------------------|-------------|
| V-1 | 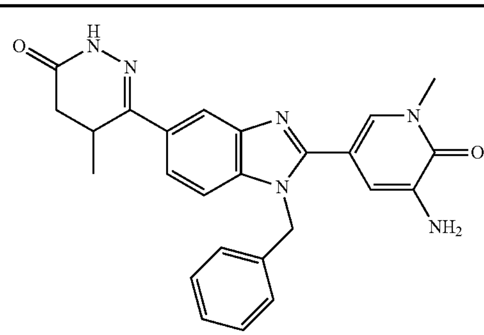 | M + H = 441; $t_{Ret.}$ = 0.92 | LCMS BAS1 |

-continued
| # | Structure | MS (M + H)+; t_Ret. HPLC [min] | HPLC-Method |
|---|---|---|---|
| V-2 | 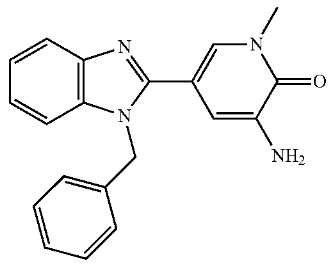 [SMILES: Cn1cc(-c2nc3ccccc3n2Cc2ccccc2)cc(N)c1=O] | M + H = 331; tRet. = 1.02 | LCMS BAS1 |
| V-3 | 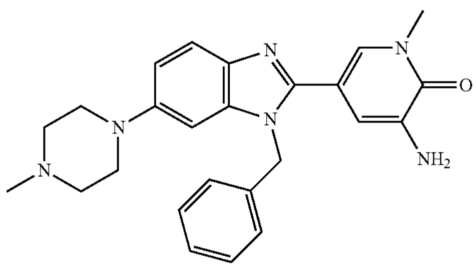 [SMILES: CN1CCN(c2ccc3nc(-c4cc(N)c(=O)n(C)c4)n(Cc4ccccc4)c3c2)CC1] | M + H = 429; tRet. = 0.92 | LCMS BAS1 |
| V-4 | 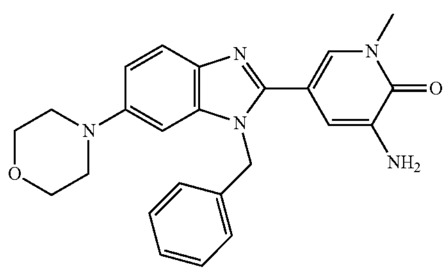 | M + H = 416; tRet. = 0.93 | LCMS BAS1 |
5-(1-benzyl-1H-1,3-benzodiazol-2-yl)-1-methyl-3-(methylamino)-1,2-dihydropyridin-2-one VI-1
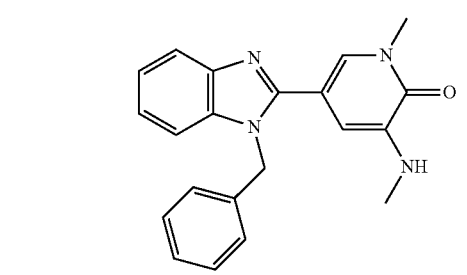
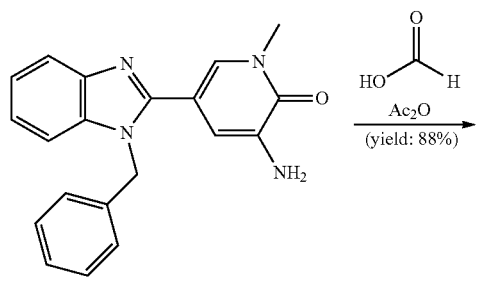
V-2
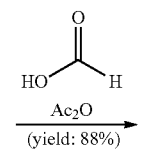
HO—CHO
Ac₂O
(yield: 88%)
-continued
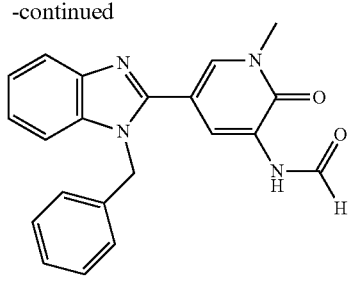
G-1
BH₃•THF complex
dry THF
(yield: 43%)
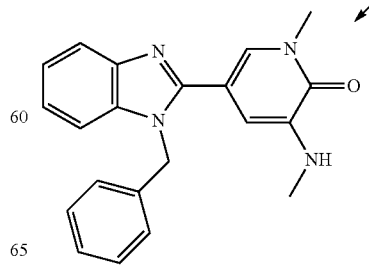
VI-1

N-[5-(1-Benzyl-1H-benzoimidazol-2-yl)-1-methyl-2-oxo-1,2-dihydro-pyridin-3-yl]-formamide G1

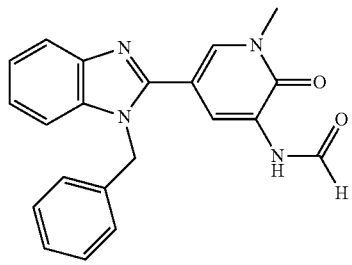 [SMILES: Cn1cc(-c2nc3ccccc3n2Cc2ccccc2)cc(NC=O)c1=O]

Acetic anhydride (0.050 ml; 0.518 mmol) is added to formic acid (1.000 ml; 25.974 mmol), the mixture is stirred at 50° C. for 1 h. The reaction is then cooled to RT and 3-amino-5-(1-benzyl-1H-benzoimidazol-2-yl)-1-methyl-1H-pyridin-2-one V-2 (97.000 mg; 0.294 mmol) is added in one portion. The reaction is stirred at RT for 16 h. The reaction mixture is concentrated under reduced pressure. The residue is dissolved in water/dcm (20 ml) and extracted 3 times with DCM (10 ml). The combined organic layers are dried with $Na_2SO_4$, filtered and concentrated under reduced pressure. The residue is used in the next step without further purification (yield: 88%; 93 mg; 0.259 mmol).

5-(1-benzyl-1H-1,3-benzodiazol-2-yl)-1-methyl-3-(methylamino)-1,2-dihydropyridin-2-one VI-1

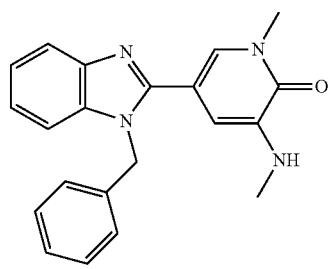 [SMILES: CNc1cc(-c2nc3ccccc3n2Cc2ccccc2)cn(C)c1=O]

N-[5-(1-Benzyl-1H-benzoimidazol-2-yl)-1-methyl-2-oxo-1,2-dihydro-pyridin-3-yl]-formamide G1 (93.000 mg; 0.259 mmol) is suspended in THF (extra dry, 2.000 ml), borane-tetrahydrofuran complex (0.259 ml; 0.259 mmol) is added at 0° C. under argon. After 1 h stirring at RT, a second portion of borane-tetrahydrofuran complex (0.259 ml; 0.259 mmol) is added to the reaction mixture at 0° C. After an extra 1 h stirring at RT, a final third portion of borane-tetrahydrofuran complex (0.259 ml; 0.259 mmol) is added to the reaction mixture at 0° C. The mixture is stirred for 30 min at RT. The reaction mixture is quenched with water and extracted with 3×10 ml DCM. The combined organic layer is dried with $Na_2SO_4$, filtered and concentrated under reduced pressure. The residue is purified on silica chromatography Combiflash (Column: Redisep Rf, 12 g; gradient: cyclohexane/EtOAc=100%/0% to 0%/100%; flow rate=30 ml/min; 28 column volumes; detection wavelength: 254 nm). Product containing fractions are combined and concentrated under reduce pressure.
Yield: 43% (38 mg; 0.110 mmol)

HPLC-MS: (M+H)+=345; $t_{Ret}$=1.20 min; method LCMS BAS1

| # | Structure | MS (M + H)+; $t_{Ret}$ HPLC [min] | HPLC-Method |
|---|---|---|---|
| VI-1 | 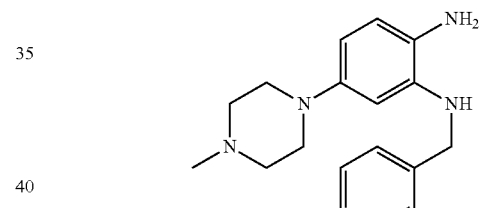 | M + H = 345; $t_{Ret.}$ = 1.20 | LCMS BAS1 |

Preparation of Intermediate of Formula E-1

Method 1:

1-N-benzyl-5-(4-methylpiperazin-1-yl)benzene-1,2-diamine E-1.1

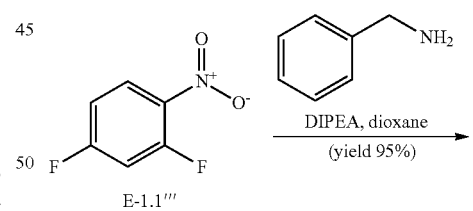

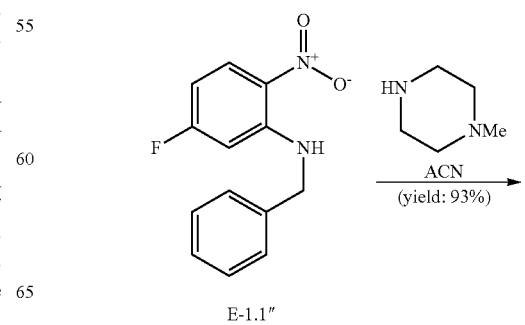

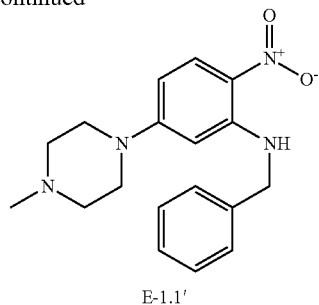

E-1.1'

↓ RaNi
THF
(yield: 74%)

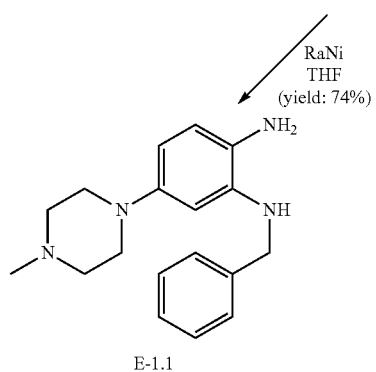

E-1.1

Benzyl-(5-fluoro-2-nitro-phenyl)-amine E-1.1"

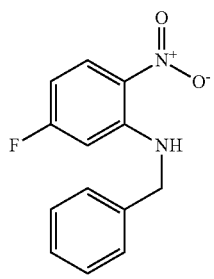

2,4-Difluoronitrobenzene E-1.1''' (3.448 ml; 31.429 mmol) is dissolved in dioxane (35.000 ml). DIPEA (6.601 ml; 40.857 mmol) and benzylamine (3.429 ml; 31.429 mmol) are added. The reaction mixture is stirred at 50° C. overnight. The reaction mixture is concentrated under reduced pressure. The residue crystallises after some minutes. It is triturated with diethyl ether to give the pure crystalline compound.

Yield: 95% (7.36 g; 28.890 mmol)

HPLC-MS: (M+H)+=247; $t_{Ret}$=1.37 min; method LCMS BAS1

N-benzyl-5-(4-methylpiperazin-1-yl)-2-nitroaniline E-1.1'

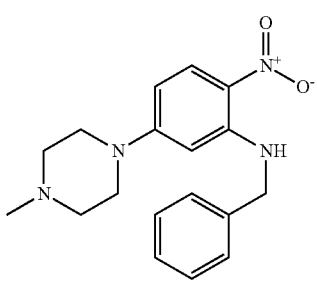 [SMILES: CN1CCN(c2ccc([N+](=O)[O-])c(NCc3ccccc3)c2)CC1]

Benzyl-(5-fluoro-2-nitro-phenyl)-amine E-1.1" (2.000 g; 6.579 mmol) is dissolved in acetonitril (10.000 ml). N-Methylpiperazine (1.460 ml; 13.158 mmol) is then added. The reaction mixture is stirred for 40 min at 160° C. in a Biotage XP Sixty microwave. The reaction mixture is poured into water and extracted with 3×50 ml DCM. The combined organic layer is dried over MgSO$_4$ and concentrated under reduced pressure. The residue is used in the next step without further purification.

Yield 93% (2.000 g; 6.128 mmol)

HPLC-MS: (M+H)+=327; $t_{Ret}$=1.22 min; method LCMS BAS1

1-N-benzyl-5-(4-methylpiperazin-1-yl)benzene-1,2-diamine E-1.1

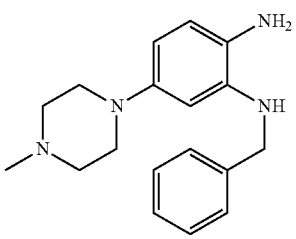

N-Benzyl-5-(4-methylpiperazin-1-yl)-2-nitroaniline E-1.1' (5.000 g; 15.319 mmol) is dissolved in THF (50.000 ml) and filled into a Büchi autoclave. RaNi (500.000 mg) is added and hydrogenated at 6 bar overnight (pressure after 16 h=0.5 bar). The autoclave is filled again with 6 bar H2 and stirred for 5 hours at rt. The reaction mixture is filtered through a plug of celite and HCl in dioxane (4 M, 4.000 ml; 16.000 mmol) is added. The filtrate is concentrated under reduced pressure to give a residue, which is dissolved in the smallest possible amount of MeOH and sonicated for few minutes. Precipitation of the product occurs and the product is filtered off. The product is washed with a very small amount of MeOH and 50 ml of isopropyl ether and then dried under reduced pressure.

Yield 74% (3.770 g; 11.326 mmol)

HPLC-MS: (M+H)+=297; $t_{Ret}$=0.95 min; method LCMS BAS1

Method 2:

(4-Amino-3-benzylamino-phenyl)-carbamic acid tert-butyl ester E-1.5

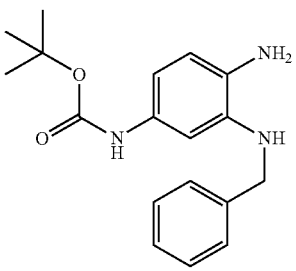

-continued

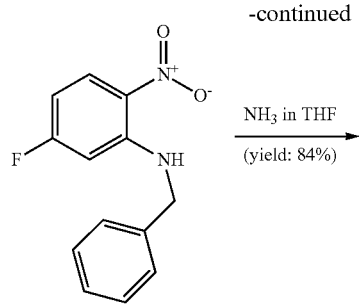

E-1.1″

NH₃ in THF
(yield: 84%)

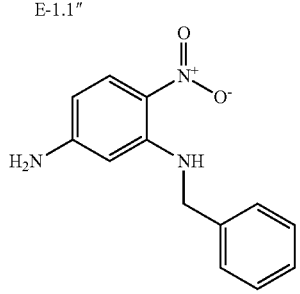

E-1.5″

Boc₂O, NEt₃
DCM
(yield: 59%)

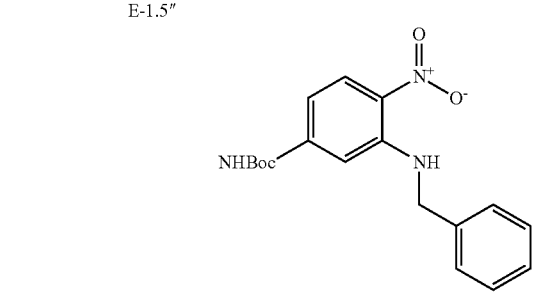

E-1.5′

Fe
EtOH
Ammonium
Chloride/Water (yield: 88%)

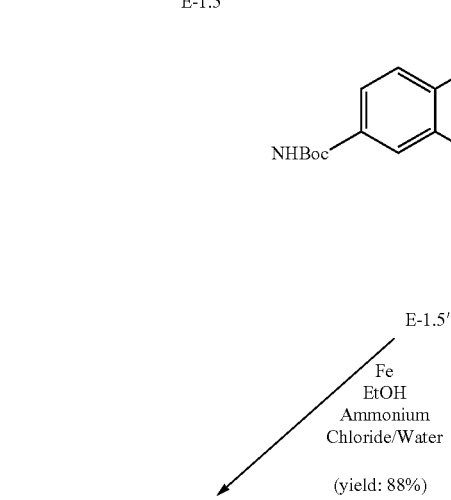

E-1.5

N3-benzyl-4-nitro-benzene-1,3-diamine E-1.5″

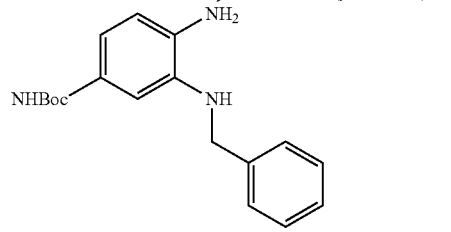

Ammonia (49 mmol) is purged in THF for 1 h at −70° C., benzyl-(5-fluoro-2-nitro-phenyl)-amine E-1.1″ (6.000 g; 24 mmol) is added to the reaction mixture. The reaction mixture is stirred in a steel bomb vessel at 90° C. for 16 h. The reaction is then cooled to 0° C., diluted with water and extracted with ethyl acetate. The combined organic layers are dried with Na₂SO₄, filtered and concentrated under reduced pressure. The residue is used in the next step without further purification (yield: 84%; 5.000 g; 20.554 mmol).

(3-Benzylamino-4-nitro-phenyl)-carbamic acid tert-butyl ester E-1.5′

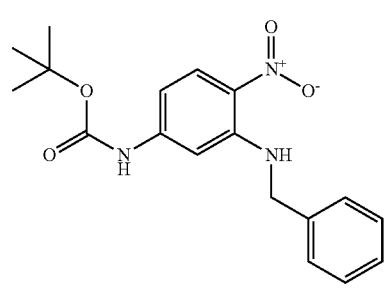 [SMILES: CC(C)(C)OC(=O)Nc1ccc([N+](=O)[O-])c(NCc2ccccc2)c1]

N3-benzyl-4-nitro-benzene-1,3-diamine E-1.5″ (6.000 g; 25 mmol) is dissolved in DCM and cooled to 0° C. Triethylamine (12.479 g; 123 mmol) is added and the mixture is stirred for 10 min Boc anhydride (13.458 g; 62 mmol) is then added and the reaction mixture is stirred at RT overnight. Cooled water is added and the mixture is extracted with ethyl acetate. The combined organic layers are dried with Na₂SO₄, filtered and concentrated under reduced pressure. The residue is used in the next step without further purification (yield: 59%, 5.000 g; 15 mmol)

HPLC-MS: (M+H)+=344; $t_{Ret}$=2.35 min; method LCMS FA-3

(4-Amino-3-benzylamino-phenyl)-carbamic acid tert-butyl ester E-1.5

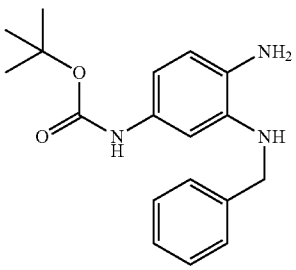 [SMILES: CC(C)(C)OC(=O)Nc1ccc(N)c(NCc2ccccc2)c1]

To a solution of (3-benzylamino-4-nitro-phenyl)-carbamic acid tert-butyl ester E-1.5′ (5.000 g; 15 mmol) in ethanol (50.000 g) is added a solution of ammonium chloride (3.932 g, 73 mmol) in water (10 ml). The reaction mixture is then stirred at 70° C. for 20 min Iron powder (4.077 g; 73 mmol) is then added portionwise and the reaction is stirred for 4 h at reflux. The reaction mixture is filtered and washed with hot ethanol. The filtrate is concentrated under reduced pressure. Water is added and the mixture is extracted with 10% MeOH in DCM. The combined organic layer is dried over Na₂SO₄

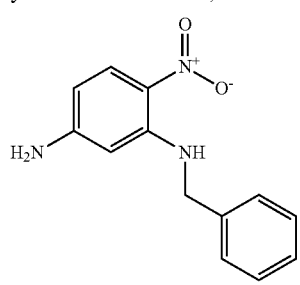

and concentrated under reduced pressure. The product is used in the next step without further purification.
Yield: 88% (4.000 g; 12.763 mmol)
HPLC-MS: (M+H)+=314; $t_{Ret}$=1.46 min; method LCMS-FA3

Method 3:

5-(oxan-4-yl)-1-N-(pyridin-2-ylmethyl)benzene-1,2-diamine E-1.9

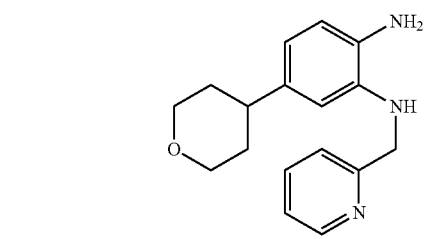

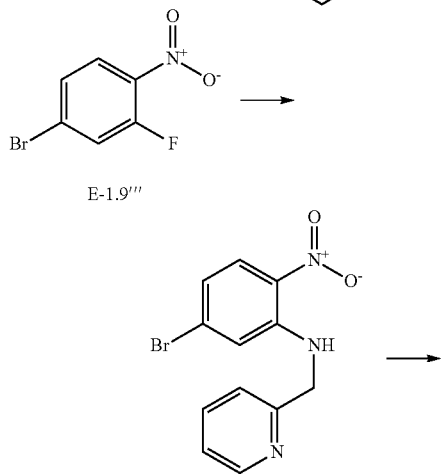

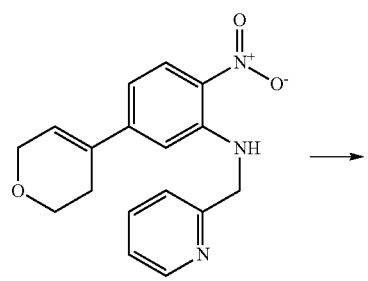

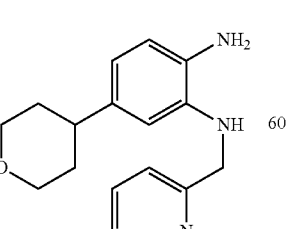

5-bromo-2-nitro-N-(pyridin-2-ylmethyl)aniline E-1.9"

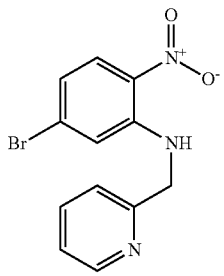 [SMILES: O=[N+]([O-])c1ccc(Br)cc1NCc1ccccn1]

The compound is prepared in a similar way as E-1-1".
HPLC-MS: (M+H)+=308/310; $t_{Ret}$=0.97 min; method VAB 5-(3,6-dihydro-2H-pyran-4-yl)-2-nitro-N-(pyridin-2-ylmethyl)aniline E-1.9'

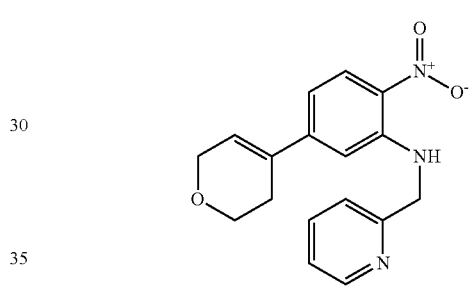

5-bromo-2-nitro-N-(pyridin-2-ylmethyl)aniline E-1.9" (145 mg; 0.47 mmol), 4-(4,4,5,5-Tetramethyl-[1,3,2]dioxaborolan-2-yl)-3,6-dihydro-2H-pyran (145 mg; 0.69 mmol), cesium carbonate (300 mg; 0.90 mmol) and [1,1'-Bis[diphenylphosphino]-ferrocene]dichloropalladium (30 mg; 0.04 mmol) are suspended in 2.5 ml dimethoxyethane and 0.8 ml water and heated for 1 h at 100° C. The solvent of the reaction mixture is removed under reduced pressure and the crude product is purified using reversed phase chromatography (Method: prep. HPLC1).
Yield: 56% (82 mg; 0.26 mmol)
HPLC-MS: (M+H)+=312; $t_{Ret}$=0.89 min; method VAB 5-(oxan-4-yl)-1-N-(pyridin-2-ylmethyl)benzene-1,2-diamine E-1.9

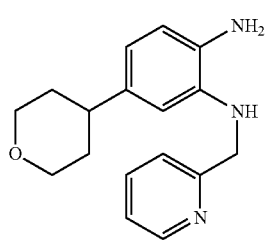 [SMILES: Nc1ccc(C2CCOCC2)cc1NCc1ccccn1]

5-(3,6-dihydro-2H-pyran-4-yl)-2-nitro-N-(pyridin-2-ylmethyl)aniline E-1.9' (82 mg; 0.26 mmol) is dissolved in THF (25 ml) and filled into a Büchi autoclave. RaNi is added and the reaction is hydrogenated with 5 bar hydrogen pressure overnight. The reaction mixture is filtered on a plug of celite. The filtrate is then concentrated under reduced pressure. The product is used in the next step without further purification.

Yield: 92% (68 mg; 0.24 mmol)
HPLC-MS: (M+H)$^+$=284; $t_{Ret}$=0.73 min; method VAB Method 4:

5-(4-methylmorpholin-2-yl)-1-N-[(1S)-1-phenyl-ethyl]benzene-1,2-diamine E-1.17

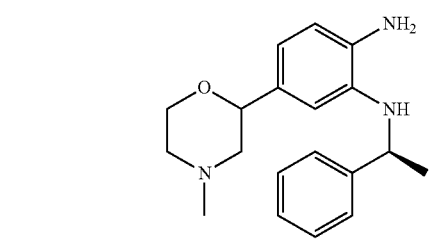

E-1.17'''

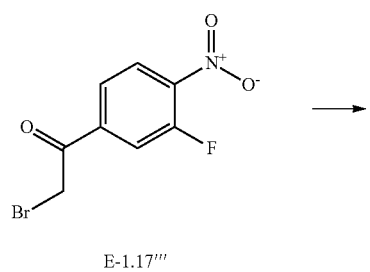

E-1.17''

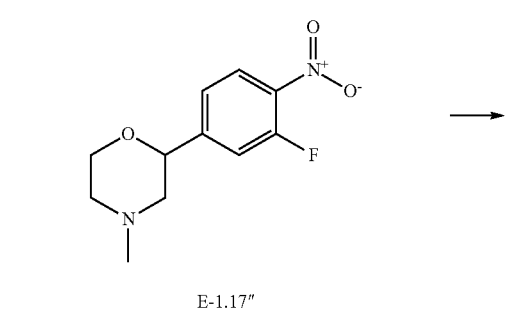

E-1.17'

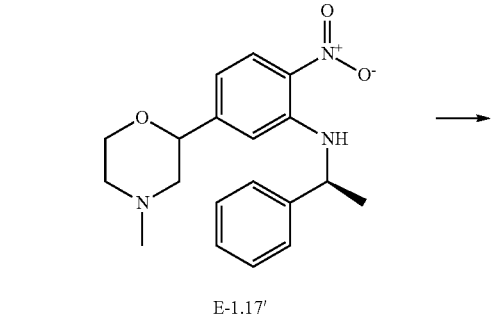

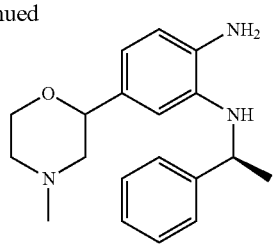

E-1.17

2-(3-fluoro-4-nitrophenyl)-4-methylmorpholine E-1.17''

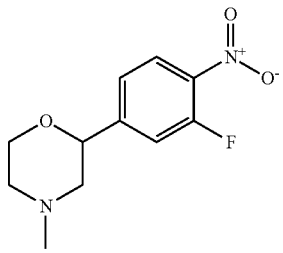 [SMILES: CN1CCOC(c2ccc([N+](=O)[O-])c(F)c2)C1]

2-bromo-1-(3-fluoro-4-nitrophenyl)ethan-1-one E-1.17''' (2.00 g; 7.63 mmol) is dissolved in dichloromethane (20 ml). DIPEA (1.4 ml; 8.00 mmol) and N-methyl ethanolamine (0.60 ml; 7.63 mmol) are added. The reaction mixture is stirred at 25° C. overnight. The reaction mixture is diluted with dichloromethane and water is added. The organic layer is separated and is dried with sodium sulfate and the solvent is removed under reduced pressure. The crude intermediate is dissolved in TFA (20 ml) and triethyl silane (8 mL) is added at 25° C. and then the reaction mixture is refluxed for 16 h. The reaction mixture is diluted with dichloromethane and the mixture is basified with saturated sodium hydrogencarbonate solution. The organic layer is separated and is dried with sodium sulfate and the solvent is removed under reduced pressure. The crude product is purified using normal phase chromatography (dichloromethane/methanol: 99:1).

Yield: 76% (1.4 g; 5.83 mmol)
E-1.17' and E-1.17 are synthesized analogues to E-1.5 and E-1.9.

5-(4-methylmorpholin-2-yl)-1-N-[(1S)-1-phenyl-ethyl]benzene-1,2-diamine E-1.17

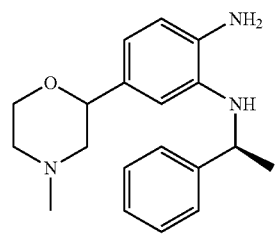 [SMILES: C[C@H](Nc1cc(C2CN(C)CCO2)ccc1N)c1ccccc1]

Yield: 95% (91 mg; 0.29 mmol)
HPLC-MS: (M+H)$^+$=312; $t_{Ret}$=0.85 min; method VAB According to the procedures of E-1.1, E-1.5, E-1.9, E-1.17 and similar procedures described in ACS Med. Chem. Lett. 2013, 4, 514-516 the following intermediates are synthesized.

| # | Structure | MS (M + H)⁺; $t_{Ret.}$ HPLC [min] | HPLC-Method |
|---|---|---|---|
| E-1.1 | | M + H = 297; $t_{Ret.}$ = 0.95 | LCMS BAS1 |
| E-1.2 | | commercially available | |
| E-1.3 | | M + H = 284; $t_{Ret.}$ = 0.76 | VAB |
| E-1.4 | | M + H = 217; $t_{Ret.}$ = 1.16 | LCMS BAS1 |
| E-1.5 | | M + H = 314; $t_{Ret.}$ = 1.46 | LCMS-FA3 |
| E-1.6 | 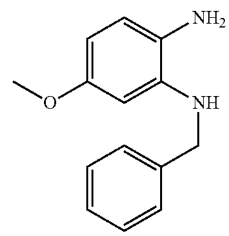 [SMILES: COc1ccc(N)c(NCc2ccccc2)c1] | M + H = 229/138; $t_{Ret.}$ = 1.15 | LCMS-FA3 |
| E-1.7 | 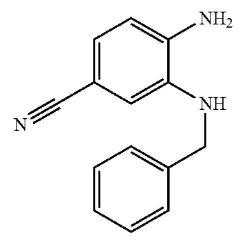 [SMILES: N#Cc1ccc(N)c(NCc2ccccc2)c1] | M + H = 224; $t_{Ret.}$ = 1.69 | LCMS-FA3 |
| E-1.8 | 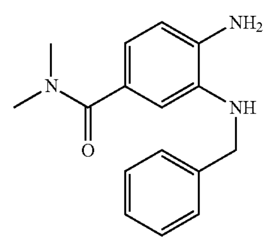 [SMILES: CN(C)C(=O)c1ccc(N)c(NCc2ccccc2)c1] | M + H = 270; | LCMS-FA3 |
| E-1.9 | 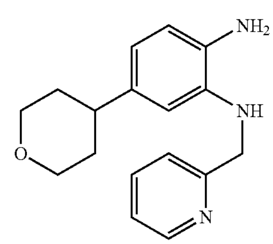 [SMILES: Nc1ccc(C2CCOCC2)cc1NCc1ccccn1] | M + H = 284; $t_{Ret.}$ = 0.73 | VAB |
| E-1.10 | 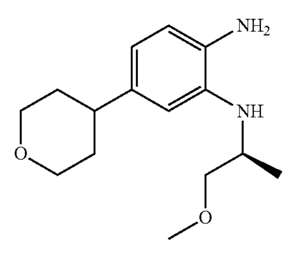 [SMILES: COC[C@H](C)Nc1cc(C2CCOCC2)ccc1N] | M + H = 264; $t_{Ret.}$ = 0.77 | VAB |
| E-1.11 | 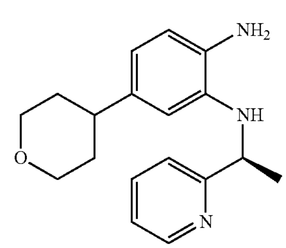 [SMILES: C[C@H](Nc1cc(C2CCOCC2)ccc1N)c1ccccn1] | M + H = 298; $t_{Ret.}$ = 0.76 | VAB |

| # | Structure | MS (M + H)+; $t_{Ret.}$ HPLC [min] | HPLC-Method |
|---|---|---|---|
| E-1.12 | 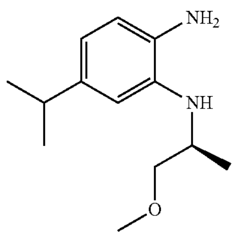 [SMILES: COC[C@H](C)Nc1cc(C(C)C)ccc1N] | M + H = 223; $t_{Ret.}$ = 0.92 | VAB |
| E-1.13 | 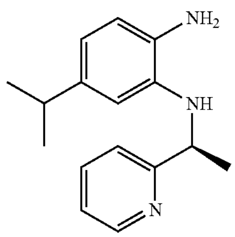 [SMILES: CC(C)c1ccc(N)c(N[C@@H](C)c2ccccn2)c1] | M + H = 256; $t_{Ret.}$ = 0.89 | VAB |
| E-1.14 | 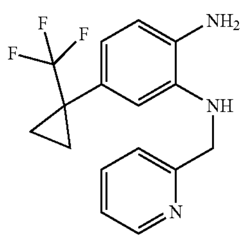 [SMILES: Nc1ccc(C2(C(F)(F)F)CC2)cc1NCc1ccccn1] | M + H = 308; $t_{Ret.}$ = 0.92 | VAB |
| E-1.15 | 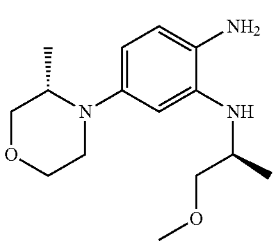 [SMILES: COC[C@H](C)Nc1cc(N2CCOC[C@@H]2C)ccc1N] | M + H = 280; $t_{Ret.}$ = 0.70 | VAB |
| E-1.16 | 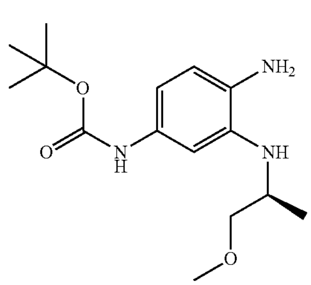 [SMILES: COC[C@H](C)Nc1cc(NC(=O)OC(C)(C)C)ccc1N] | M + H = 296 | LCMS-FA3 |
| E-1.17 | 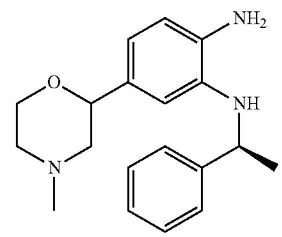 [SMILES: C[C@H](Nc1cc(C2CN(C)CCO2)ccc1N)c1ccccc1] | M + H = 312; $t_{Ret.}$ = 0.85 | VAB |
| E-1.18 | 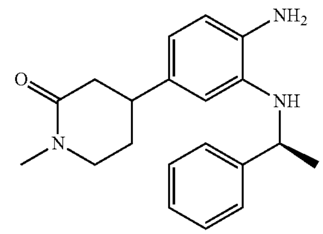 [SMILES: C[C@H](Nc1cc(C2CCN(C)C(=O)C2)ccc1N)c1ccccc1] | M + H = 324; $t_{Ret.}$ = 0.82 | VAB |
| E-1.19 | 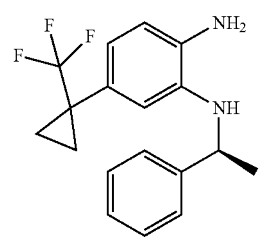 [SMILES: C[C@H](Nc1cc(C2(C(F)(F)F)CC2)ccc1N)c1ccccc1] | M + H = 321; $t_{Ret.}$ = 1.07 | VAB |

Preparation Of Intermediate Of Formula E-2

Method 1:

N-4-Benzyl-6-(4-methyl-piperazin-1-yl)-pyridine-3,4-diamine E-2.1

119
-continued

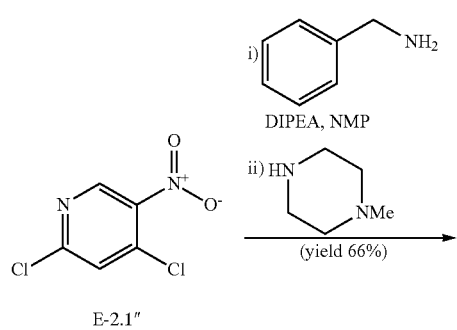

E-2.1″

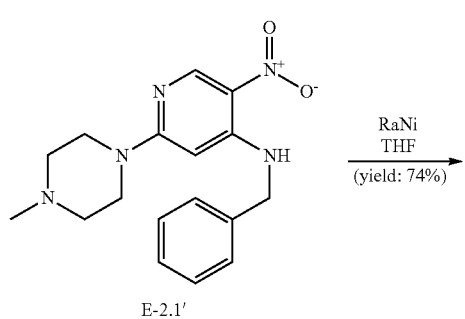

E-2.1′

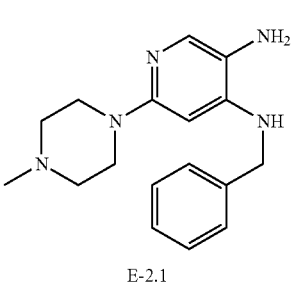

E-2.1

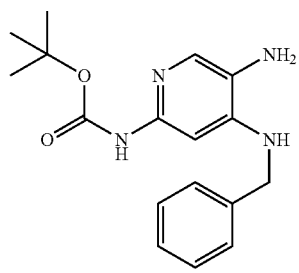 [SMILES: CC(C)(C)OC(=O)Nc1cc(NCc2ccccc2)c(N)cn1]

Benzyl-[2-(4-methyl-piperazin-1-yl)-5-nitro-pyridin-4-yl]-amine E-2.1'

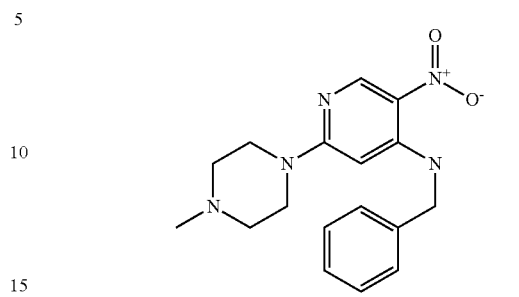

To a solution of 2,4-dichloro-5-nitro-pyridine E-2.1″ (5.000 g; 25.908 mmol) in NMP are added DIPEA (8.372 ml, 51.817 mmol) and benzylamine (3.054 ml, 28.499 mmol). The mixture is stirred for 1 h at RT. 1-Methylpiperazine (3.172 ml; 28.499 mmol) is then added and the mixture is stirred at 50° C. overnight. The residue is loaded onto isolute, split into 5 portions and purified using the basic preparatory reversed phase chromatography (method: prep. HPLC1). Product containing fractions are combined and freeze-dried (yield: 66%, 5.619 g; 17.163 mmol)

N-4-Benzyl-6-(4-methyl-piperazin-1-yl)-pyridine-3,4-diamine E-2.1

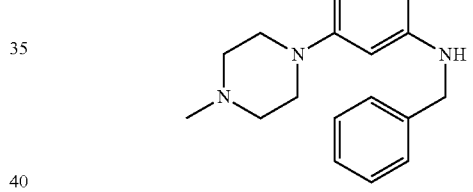

Benzyl-[2-(4-methyl-piperazin-1-yl)-5-nitro-pyridin-4-yl]-amine E-2.1' (400 mg; 1.222 mmol) is dissolved in THF (50.000 ml) and filled into a Büchi autoclave. RaNi is added and the reaction is hydrogenated with 5 bar hydrogen pressure overnight. The reaction mixture is filtered on a plug of celite. The filtrate is then concentrated under reduced pressure. The product is used in the next step without further purification.
Yield: 74% (270 mg; 0.908 mmol)
HPLC-MS: $(M+H)^+=298$; $t_{Ret}=0.68$ min; method VAB Method 2:

(5-Amino-4-benzylamino-pyridin-2-yl)-carbamic acid tert-butyl ester E-2-11

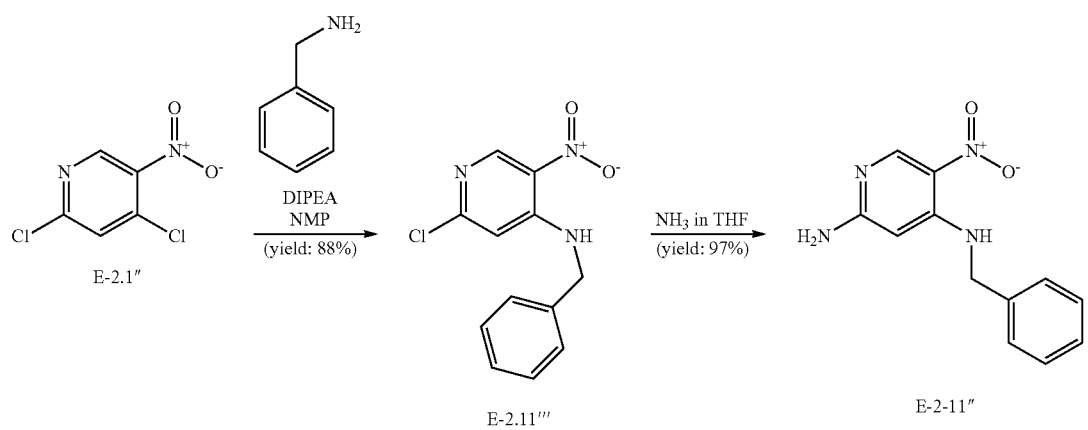

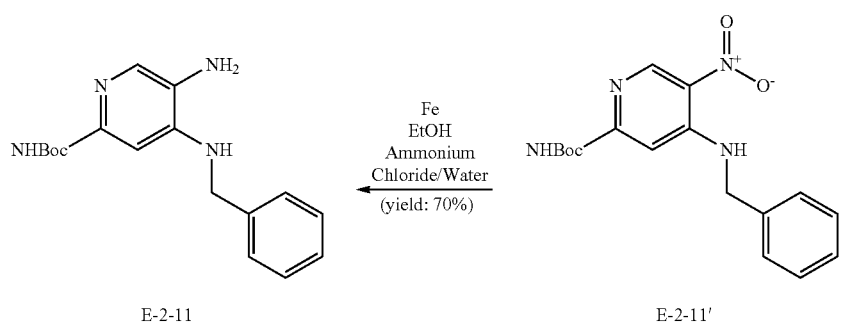

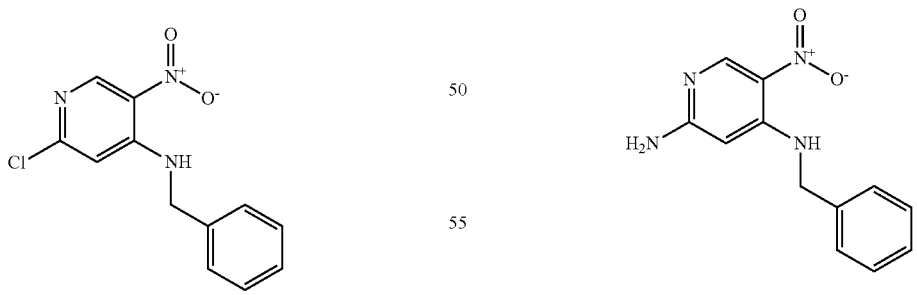

Benzyl-(2-chloro-5-nitro-pyridin-4-yl)-amine E-2.11'''

To a stirred solution of 2,4-dichloro-5-nitropyridine E-2.1" (10.000 g; 51.817 mmol) and benzylamine (5.552 g; 51.817 mmol) in NMP is added DIPEA (20.053 g; 155.451 mmol) at 0° C. The mixture is stirred at RT for 1 h. Water is added, precipitation of the product occurs. Product is filtered off and dried under vacuum.

The product is used in the next step without further purification (yield: 88%, 12.000 g; 45.510 mmol)

N*4*-Benzyl-5-nitro-pyridine-2,4-E-2-11"

A solution of benzyl-(2-chloro-5-nitro-pyridin-4-yl)-amine E-2.11' (10.000 g; 38.02 mmol) in THF is placed in a steel bomb vessel. Liquid ammonia is added at −78° C. and the mixture is stirred at 90° C. for 16 h. The reaction is concentrated under reduced pressure. Water is added, precipitation of the product occurs. Product is filtered off and dried under vacuum. The residue is used in the next step without further purification (yield: 97%, 9.000 g; 36.85 mmol)

123

(4-Benzylamino-5-nitro-pyridin-2-yl)-carbamic acid tert-butyl ester E-2.11'

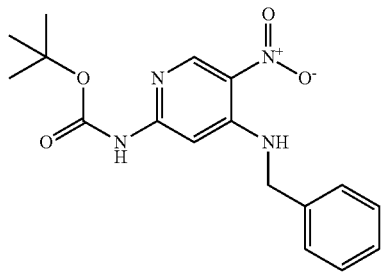

LiHMDS (1M in THF, 55.271 mmol) is added at −78° C. to a solution of N*4*-benzyl-5-nitro-pyridine-2,4-E-2-11" (9.000 g; 36.85 mmol) in THF, the mixture is stirred for 15 min at −78° C. Boc anhydride (8.836 g; 40.53 mmol) is then added and the mixture is stirred for 1 h at −78° C. The reaction mixture is quenched with aq NH4Cl solution, precipitation of the product occurs. Product is filtered off and dried under vacuum. The residue is used in the next step without further purification (yield: 55%, 7.000 g; 20.327 mmol).

(5-Amino-4-benzylamino-pyridin-2-yl)-carbamic acid tert-butyl ester E-2-11

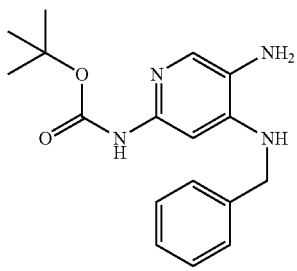

To a solution of (4-Benzylamino-5-nitro-pyridin-2-yl)-carbamic acid tert-butyl ester E-2.11' (7.000 g; 20.327 mmol) in ethanol is added a solution of ammonium chloride (5.427 g, 102 mmol) in water and iron powder (5.671 g; 102 mmol). The reaction is stirred at 80° C. for 2 h. The reaction mixture is filtered through celite. The filtrate is concentrated under reduced pressure. The residue is purified by flash column chromatography on basic alumina using 1-2% MeOH/DCM as eluent. The isolated product is obtained as brown colour solid. It is taken for the next step without further purification.

Yield: 70% (4.500 g; 14.314 mmol)
TLC (10% MeOH/90% DCM): Rf=0.09

Method 3:

6-(Propan-2-yl)-4-N-(pyridin-2-ylmethyl)pyridine-3,4-diamine E-2.17

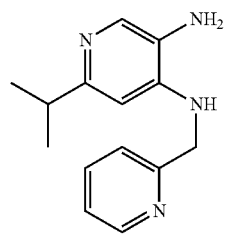

124

-continued

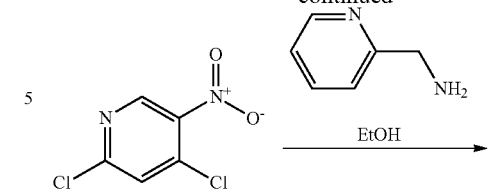

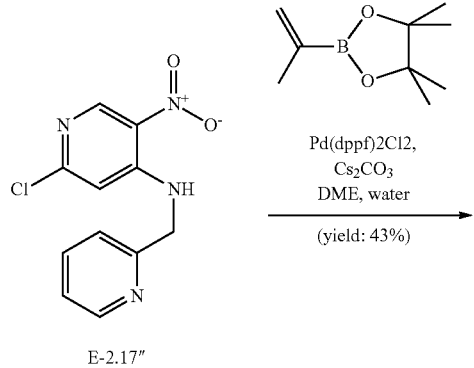

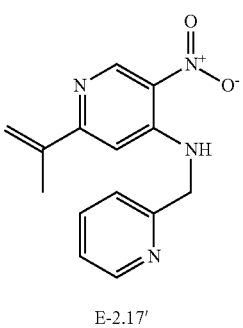

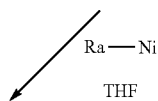

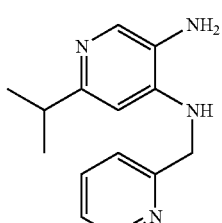

E-2.17

2-Chloro-5-nitro-N-(pyridin-2-ylmethyl)pyridin-4-amine E-2.17"

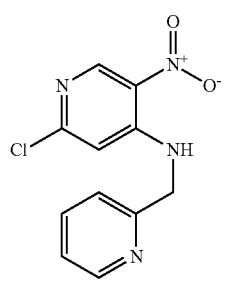

E.2-17" is synthesized according to procedure described for the synthesis of E-2.11''' from E-2.1".

5-Nitro-2-(prop-1-en-2-yl)-N-(pyridin-2-ylmethyl)pyridin-4-amine E-2.17'

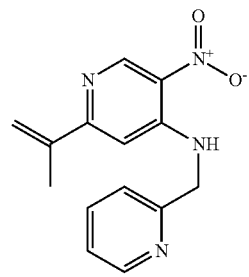 [SMILES: C=C(C)c1cc(NCc2ccccn2)c([N+](=O)[O-])cn1]

2-Chloro-5-nitro-N-(pyridin-2-ylmethyl)pyridin-4-amine E-2.17" (125 mg; 0.47 mmol), 4,4,5,5-tetramethyl-2-(prop-1-en-2-yl)-1,3,2-dioxaborolane (200 µl; 1.06 mmol), cesium carbonate (300 mg; 0.90 mmol) and [1,1'-Bis[diphenylphosphino]-ferrocene]dichloropalladium (30 mg; 0.04 mmol) are suspended in 7.5 ml dimethoxyethane and 2.5 ml water and heated for 1 h at 100° C. The solvent of the reaction mixture is removed under reduced pressure and the crude product is purified using reversed phase chromatography (Method: prep. HPLC1).

Yield: 43% (55 mg; 0.20 mmol)
HPLC-MS: $(M+H)^+=271$; $t_{Ret}=1.09$ min; method LCMS BAS1

6-(Propan-2-yl)-4-N-(pyridin-2-ylmethyl)pyridine-3,4-diamine E-2.17

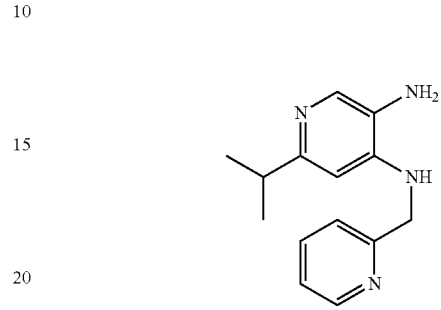

E.2-17 is synthesized according to the procedure described for the synthesis of E-2.1 from E.2-1'.

According to the procedures of E-2.1, E.2-11 and E.2-17, the following intermediates are synthesized.

| # | Structure | MS (M + H)+; $t_{Ret.}$ HPLC [min] | HPLC-Method |
|---|---|---|---|
| E-2.1 | 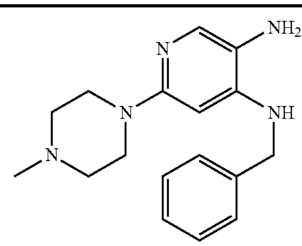 | M + H = 298; $t_{Ret.}$ = 0.68 | VAB |
| E-2.2 | 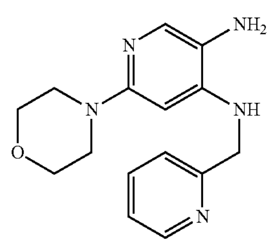 [SMILES: Nc1cnc(N2CCOCC2)cc1NCc1ccccn1] | M + H = 286; $t_{Ret.}$ = 0.58 | VAB |
| E-2.3 | 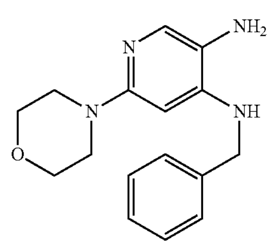 [SMILES: Nc1cnc(N2CCOCC2)cc1NCc1ccccc1] | M + H = 285; $t_{Ret.}$ = 0.68 | 10-90 AB_2minLCMS |

-continued

| # | Structure | MS (M + H)+; t_Ret. HPLC [min] | HPLC-Method |
|---|---|---|---|
| E-2.4 | 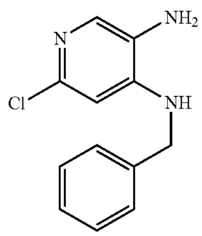 [SMILES: Nc1cnc(Cl)cc1NCc1ccccc1] | M + H = 234; t_Ret. = 1.61 | VAB |
| E-2.5 | 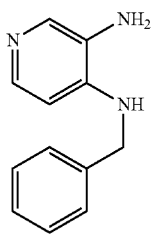 [SMILES: Nc1cnccc1NCc1ccccc1] | M + H = 200; t_Ret. = 0.79 | LCMS BAS1 |
| E-2.6 | 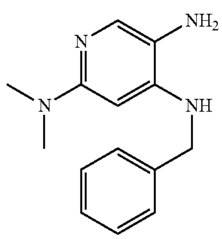 [SMILES: CN(C)c1cc(NCc2ccccc2)c(N)cn1] | M + H = 243; t_Ret. = 0.94 | LCMS BAS1 |
| E-2.7 | 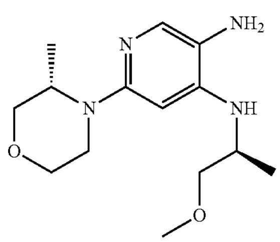 [SMILES: COC[C@H](C)Nc1cc(N2CCOC[C@@H]2C)ncc1N] | M + H = 281; t_Ret. = 0.67 | VAB |
| E-2.8 | 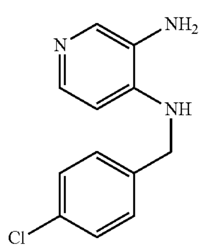 [SMILES: Nc1cnccc1NCc1ccc(Cl)cc1] | M + H = 234; t_Ret. = 1.51 | LCMS-FA3 |
| E-2.9 | 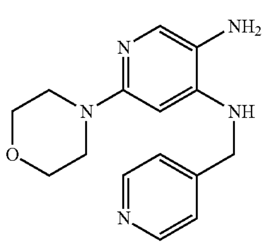 | M + H = 286/243/150; t_Ret. = 1.28 | LCMS-FA3 |

-continued

| # | Structure | MS (M + H)+; t_Ret. HPLC [min] | HPLC-Method |
|---|---|---|---|
| E-2.10 | 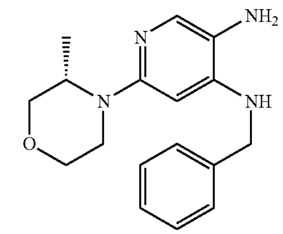 [SMILES: C[C@H]1COCCN1c1cc(NCc2ccccc2)c(N)cn1] | M + H = 299; t_Ret. = 1.55 | FECB5 |
| E-2.11 | 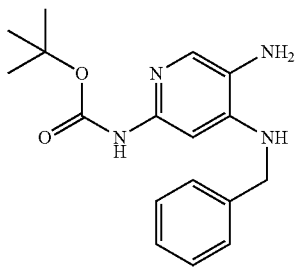 [SMILES: CC(C)(C)OC(=O)Nc1cc(NCc2ccccc2)c(N)cn1] | Observed by TLC Rf = 0.09 (10% MeOH/90% DCM) | |
| E-2.12 | 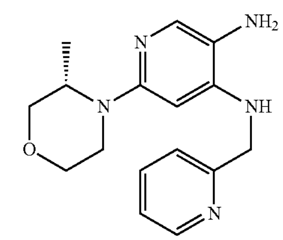 [SMILES: C[C@H]1COCCN1c1cc(NCc2ccccn2)c(N)cn1] | M + H = 300; t_Ret. = 0.65 | VAB |
| E-2.13 | 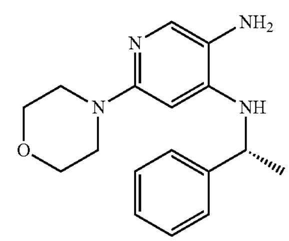 | M + H = 299; t_Ret. = 1.55 | FECB5 |
| E-2.14 | 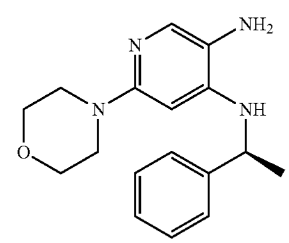 | M + H = 299; t_Ret. = 0.79 | VAB |
| E-2.15 | 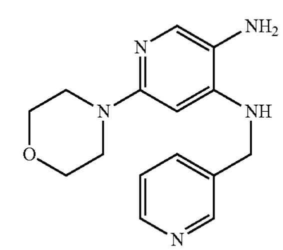 [SMILES: Nc1cnc(N2CCOCC2)cc1NCc1cccnc1] | M + H = 286; t_Ret. = 4.17 | LCMS-MS ammonium acetate -1 |

-continued

| # | Structure | MS (M + H)+; $t_{Ret.}$ HPLC [min] | HPLC-Method |
|---|---|---|---|
| E-2.16 | 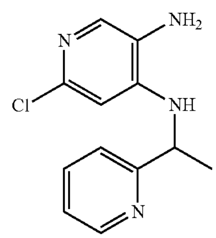 [SMILES: CC(Nc1cc(Cl)ncc1N)c1ccccn1] | M + H = 249/251 $t_{Ret.}$ = 1.74 | LCMS BAS1 |
| E-2.17 | 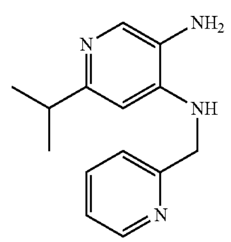 [SMILES: CC(C)c1cc(NCc2ccccn2)c(N)cn1] | M + H = 243; $t_{Ret.}$ = 0.70 | VAB |
| E-2.18 | 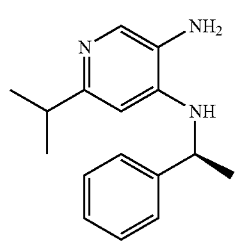 [SMILES: CC(C)c1cc(N[C@@H](C)c2ccccc2)c(N)cn1] | M + H = 256; $t_{Ret.}$ = 1.59 | FECB5 |
| E-2.19 | 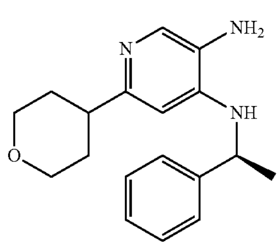 | M + H = 298; $t_{Ret.}$ = 0.80 | VAB |
| E-2.20 | 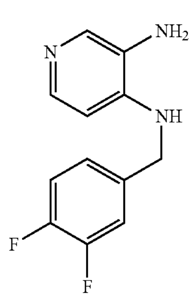 [SMILES: Nc1cnccc1NCc1ccc(F)c(F)c1] | M + H = 236 | LCMS-MS ammonium acetate-1 |
| E-2.21 | 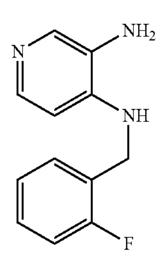 [SMILES: Nc1cnccc1NCc1ccccc1F] | M + H = 218 | LCMS-MS ammonium acetate-1 |

-continued

| # | Structure | MS (M + H)+; t_Ret. HPLC [min] | HPLC-Method |
|---|---|---|---|
| E-2.22 | 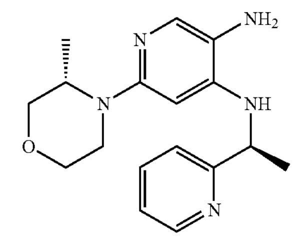 [SMILES: C[C@H](Nc1cc(N2CCOC[C@@H]2C)ncc1N)c1ccccn1] | M + H = 314; t_Ret. = 1.40 | FECB5 |
| E-2.23 | 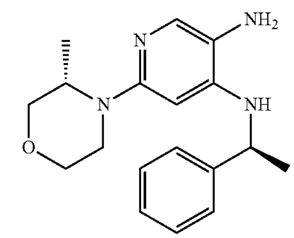 [SMILES: C[C@H](Nc1cc(N2CCOC[C@@H]2C)ncc1N)c1ccccc1] | M + H = 313; t_Ret. = 1.60 | FECB5 |
| E-2.24 | 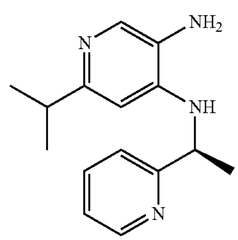 [SMILES: CC(C)c1cc(N[C@@H](C)c2ccccn2)c(N)cn1] | M + H = 257; t_Ret. = 0.72 | VAB |
| E-2.25 | 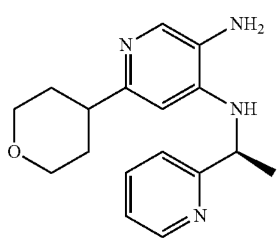 [SMILES: C[C@H](Nc1cc(C2CCOCC2)ncc1N)c1ccccn1] | M + H = 299; t_Ret. = 0.65 | VAB |
| E-2.26 | 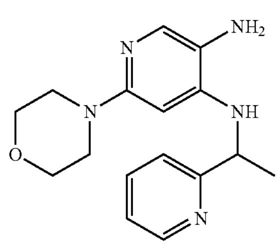 [SMILES: CC(Nc1cc(N2CCOCC2)ncc1N)c1ccccn1] | M + H = 300; t_Ret. = 1.31 | FECB5 |
| E-2.27 | 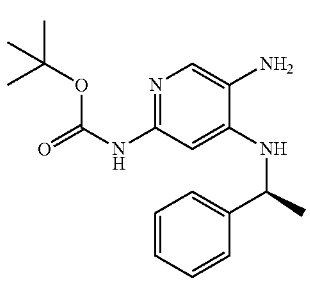 [SMILES: C[C@H](Nc1cc(NC(=O)OC(C)(C)C)ncc1N)c1ccccc1] | M + H = 329 | LCMS-MS ammonium acetate-1 |

135

-continued

| # | Structure | MS (M + H)+; $t_{Ret.}$ HPLC [min] | HPLC-Method |
|---|---|---|---|
| E-2.28 | 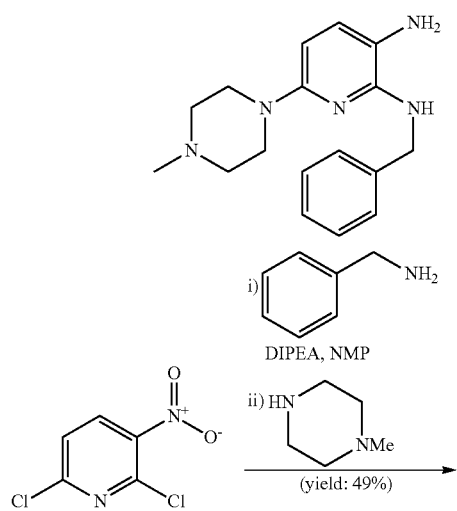 | M + H = 291; $t_{Ret.}$ = 0.83 | FECB5 |
| E-2.29 | 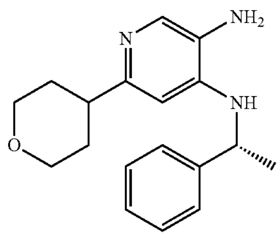 [SMILES: C[C@@H](Nc1cc(C2CCOCC2)ncc1N)c1ccccc1] | M + H = 298; $t_{Ret.}$ = 0.81 | FECB5 |

Preparation Of Intermediate Of Formula E-3

1-N-benzyl-5-(4-methylpiperazin-1-yl)benzene-1,2-diamine E-3.1

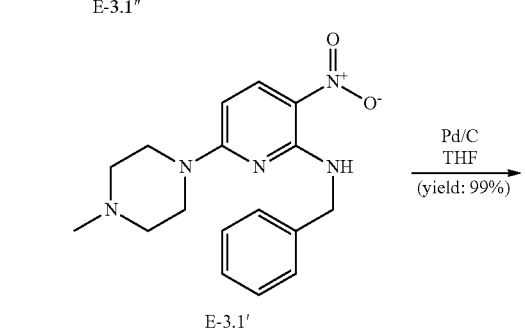

136

-continued

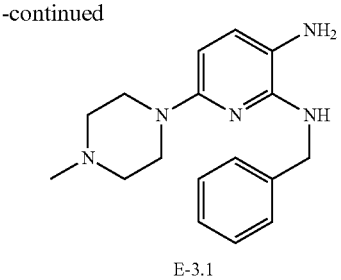

E-3.1

Benzyl-[6-(4-methyl-piperazin-1-yl)-3-nitro-pyridin-2-yl]-amine E-3.1'

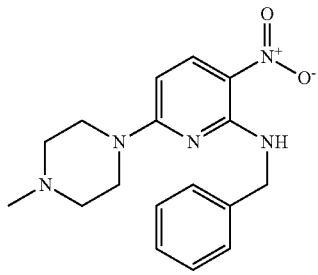 [SMILES: CN1CCN(c2ccc([N+](=O)[O-])c(NCc3ccccc3)n2)CC1]

2,6-Dichloro-3-nitropyridine E-3.1" (1.5 g; 7.151 mmol) is suspended in NMP and cooled to 0° C. DIPEA (2.31 ml, 14.3 mmol) and benzylamine (800 μl; 7.47 mmol) are added, the reaction mixture is stirred at RT. To this suspension 1-methylpiperazine (875 μl; 7.87 mmol) is added and the resulting mixture is stirred for 16 h at 50° C. The crude intermediate is purified using reversed phase chromatography (prep. HPLC1). The product containing fractions are combined and freeze-dried (Yield: 49%; 1.144 g; 3.494 mmol)

1-N-Benzyl-5-(4-methylpiperazin-1-yl)benzene-1,2-diamine E-3.1

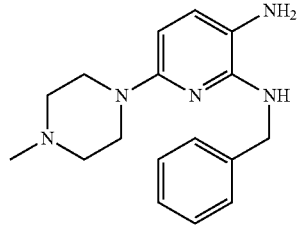 [SMILES: CN1CCN(c2ccc(N)c(NCc3ccccc3)n2)CC1]

Benzyl-[6-(4-methyl-piperazin-1-yl)-3-nitro-pyridin-2-yl]-amine E-3.1' (600 mg; 1.833 mmol) is dissolved in THF and palladium on carbon is added. The reaction mixture is stirred for 2.5 h at 25° C. and 4 bar hydrogen pressure. The catalyst is filtered off under celite, the filtrate is concentrated and dried under reduced pressure.

Yield: 90% (600 mg; 1.816 mmol)
HPLC-MS: (M+H)$^+$=298; $t_{Ret.}$=0.759 min; method VAB 6-[(1-methylpiperidin-4-yl)oxy]-2-N-[1-(pyridin-2-yl)ethyl]pyridine-2,3-diamine E-3.8

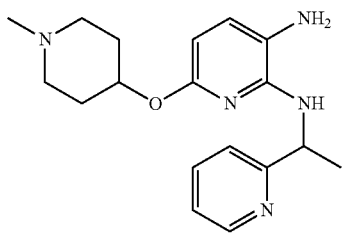 [SMILES: CC(Nc1nc(OC2CCN(C)CC2)ccc1N)c1ccccn1]

The compound can be synthesized similar to E-3.1, but for the introduction of the alcohol different conditions can be used:

6-[(1-methylpiperidin-4-yl)oxy]-3-nitro-N-[1-(pyridin-2-yl)ethyl]pyridin-2-amine E-3.8'

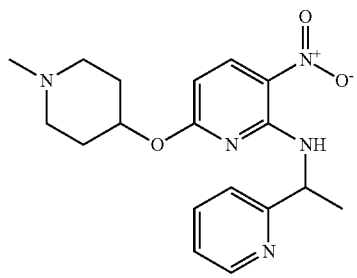 [SMILES: CC(Nc1nc(OC2CCN(C)CC2)ccc1[N+](=O)[O-])c1ccccn1]

6-chloro-3-nitro-N-[1-(pyridin-2-yl)ethyl]pyridin-2-amine E-3.8" (2 g; 7.17 mmol) is suspended in 20 ml THF and a potassium bis(trimethylsilyl)amide solution in THF (29 ml; 29 mmol) is slowly added at 25° C. After 15 min 4-hydroxy-N-methylpiperidine (3.37 g; 28.71 mmol) is added and the reaction mixture is stirred for 16 h at 25° C. The reaction mixture is diluted with ethyl acetated and water. The organic phase is separated and dried using MgSO4. The crude intermediate is purified using reversed phase chromatography (prep. HPLC1). The product containing fractions are combined and freeze-dried Yield: 22%; (570 mg; 1.60 mmol)
HPLC-MS: (M+H)$^+$=358; $t_{Ret.}$=0.61 min; method BFEC According to the procedures of E-3.1 and E-3.8 the following intermediates are synthesized.

| # | Structure | MS (M + H)$^+$; $t_{Ret.}$ HPLC [min] | HPLC-Method |
|---|---|---|---|
| E-3.1 | 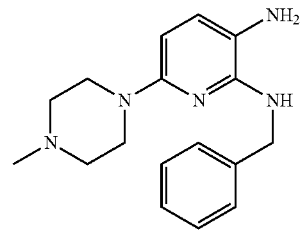 [SMILES: CN1CCN(c2ccc(N)c(NCc3ccccc3)n2)CC1] | M + H = 298; $t_{Ret.}$ = 0.759 | VAB |
| E-3.2 | 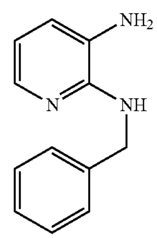 | commercially available | |
| E-3.3 | 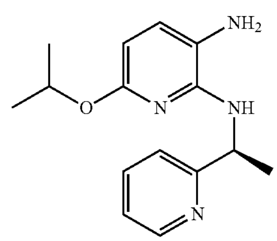 [SMILES: CC(C)Oc1ccc(N)c(N[C@@H](C)c2ccccn2)n1] | M + H = 273 | VAB |
| E-3.4 | 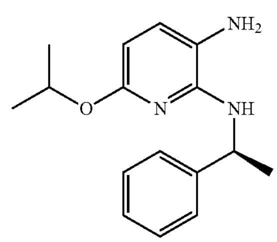 [SMILES: CC(C)Oc1ccc(N)c(N[C@@H](C)c2ccccc2)n1] | M + H = 272 | VAB |
| E-3.5 | 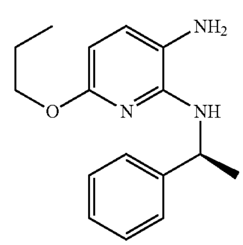 [SMILES: CCCOc1ccc(N)c(N[C@@H](C)c2ccccc2)n1] | M + H = 272 | VAB |

139
-continued

| # | Structure | MS (M + H)+; t_Ret. HPLC [min] | HPLC-Method |
|---|---|---|---|
| E-3.6 | (structure: 6-isopropoxy-pyridine with NH2 and NH-CH(CH3)-pyridin-2-yl) | M + H = 273 | VAB |
| E-3.7 | (structure: 6-((R)-cyclopentyloxy)-pyridine with NH2 and NH-CH(CH3)-pyridin-2-yl) | M + H = 299 | VAB |

140
-continued

| # | Structure | MS (M + H)+; t_Ret. HPLC [min] | HPLC-Method |
|---|---|---|---|
| E-3.8 | (structure: 6-((1-methylpiperidin-4-yl)oxy)-pyridine with NH2 and NH-CH(CH3)-pyridin-2-yl) | M + H = 358; t_Ret. = 0.61 | BFEC |

Preparation Of Intermediate Of Formula E-4

1-N-benzyl-5-(4-methylpiperazin-1-yl)benzene-1,2-diamine E-4.1

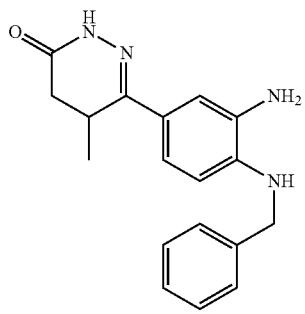

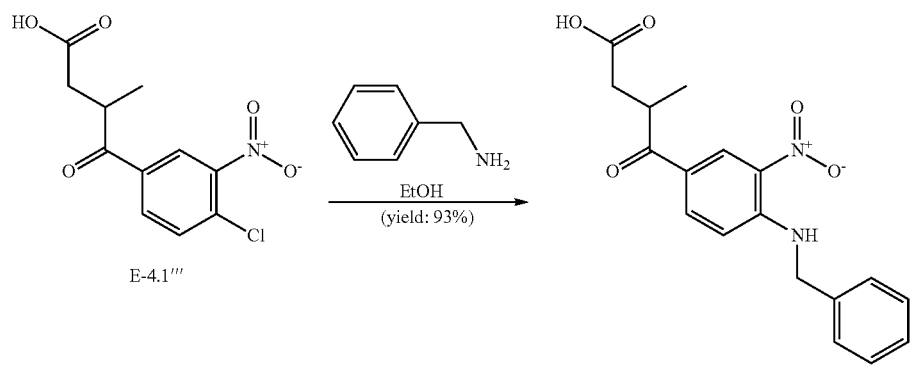

E-4.1‴ → E-4.1″

EtOH (yield: 93%)

$H_2N-NH_2$
EtOH; AcOH
(yield: 71%)

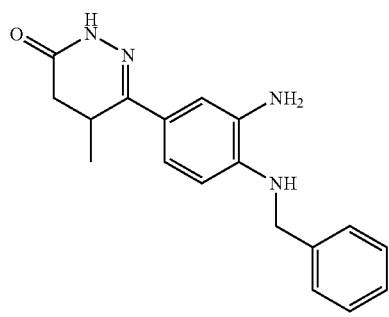

E-4.1

Ra—Ni
THF
(yield: 92%)
-continued

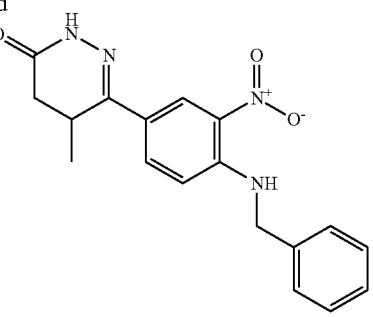

E-4.1'

4-(4-Benzylamino-3-nitro-phenyl)-3-methyl-4-oxo-butyric acid E-4.1''

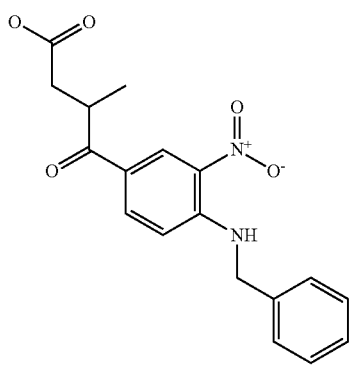 [SMILES: CC(CC(=O)O)C(=O)c1ccc(NCc2ccccc2)c([N+](=O)[O-])c1]

4-(4-Chloro-3-nitro-phenyl)-3-methyl-4-oxo-butyric acid E-4.1''' (800 mg; 2.95 mmol) is placed in 8 ml ethanol and heated up to 50° C. to get solved. Benzylamine (1.61 ml; 14.73 mmol) is added and the reaction mixture stirred for 3 hours at 100° C. The crude product is purified by using reversed phase chromatography (Method: prep. HPLC1).

Yield: 93% (939 mg; 2.74 mmol)

HPLC-MS: (M+H)+=343; tRet=0.68 min; method VAB 6-(4-Benzylamino-3-nitro-phenyl)-5-methyl-4,5-dihydro-2H-pyridazin-3-one E-4.1'

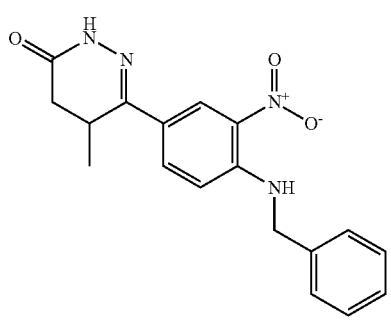 [SMILES: CC1CC(=O)NN=C1c1ccc(NCc2ccccc2)c([N+](=O)[O-])c1]

4-(4-Benzylamino-3-nitro-phenyl)-3-methyl-4-oxo-butyric acid E-4.1'' (939 mg; 2.74 mmol) is placed in 7 ml ethanol and treated with hydrazine hydrate (0.16 ml; 3.29 mmol) and acetic acid (78.58 µl; 1.37 mmol). The reaction mixture is heated up to 100° C. for 2 hours. Another portion of hydrazine hydrate (0.08 ml; 1.65 mmol) and 40 µl acetic acid are added and stirred for 2 hours at 100° C. After letting the reaction cooling to RT, the product precipitates. It is filtered off and washed with methanol and dried under reduced pressure.

Yield: 71% (662 mg; 1.96 mmol)

HPLC-MS: (M+H)+=339; $t_{Ret}$=0.87 min; method VAB 6-(3-Amino-4-benzylamino-phenyl)-5-methyl-4,5-dihydro-2H-pyridazin-3-one E-4.1

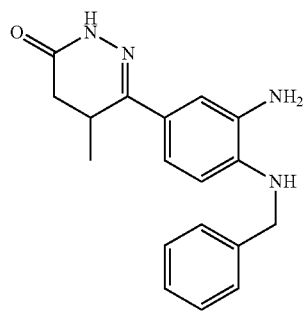 [SMILES: CC1CC(=O)NN=C1c1ccc(NCc2ccccc2)c(N)c1]

6-(4-Benzylamino-3-nitro-phenyl)-5-methyl-4,5-dihydro-2H-pyridazin-3-one E-4.1' (662 mg; 1.96 mmol) is solved in 200 ml THF, a scoop of Raney Nickel is then added. The mixture is placed in the hydrogenation apparatus and stirred at RT for 1.5 hours under 4 bar hydrogen pressure. The Raney Nickel is filtered off and the reaction solution evaporated to dryness.

Yield: 92% (650 mg; 1.79 mmol)

HPLC-MS: (M+H)+=309; tRet=0.77 min; method VAB

According to the procedures of E-1.1, E-2.1, E-3.1 E-4.1 and literature procedure [Julemont et al., J. Med. Chem., 47 (27), 6749-6759, 2004—synthesis of E-4.4, synthesis of E-4.5-E-4.7: starting from E-4.2 and applying Buchwald-Hartwig reaction or Suzuki reaction] the following intermediates are synthesized.

| # | Structure | MS (M + H)+; t_Ret. HPLC [min] | HPLC-Method |
|---|---|---|---|
| E-4.1 | 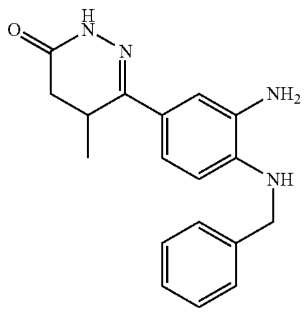 [SMILES: CC1CC(=O)NN=C1c1ccc(NCc2ccccc2)c(N)c1] | M + H = 309; t_Ret. = 1.63 | FECB5 |
| E-4.2 | 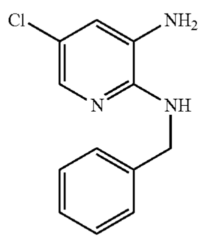 [SMILES: Nc1cc(Cl)cnc1NCc1ccccc1] | M + H = 234; t_Ret. = 1.44 | LCMS FA-2 |
| E-4.3 | 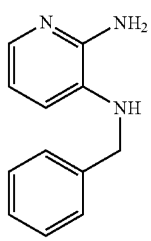 [SMILES: Nc1ncccc1NCc1ccccc1] | commercially available | |
| E-4.4 | 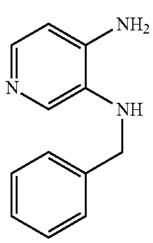 [SMILES: Nc1ccncc1NCc1ccccc1] | M + H = 200; tRet. = 1.59 | LCMS FA-2 |
| E-4.5 | 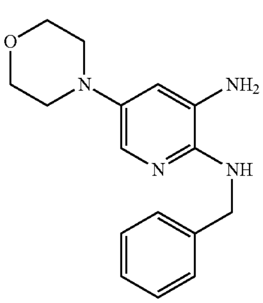 [SMILES: Nc1cc(N2CCOCC2)cnc1NCc1ccccc1] | M + H = 285 | LCMS FA-2 |
| E-4.6 | | M + H = 298 | LCMS FA-2 |
| E-4.7 | | M + H = 284 | LCMS FA-2 |
| E-4.8 | | M + H = 214 | LCMS FA-2 |
| E-4.9 | | M + H = 307 | LCMS FA-2 |
| E-4.10 | | M + H = 214; tRet. = 0.76 | VAB |

-continued

| # | Structure | MS (M + H)+; $t_{Ret.}$ HPLC [min] | HPLC-Method |
|---|---|---|---|
| E-4.11 | 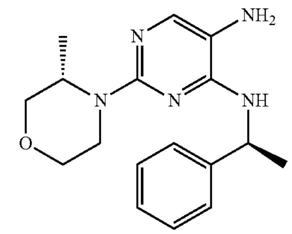 | M + H = 314; tRet. = 0.83 | VAB |
| E-4.12 | 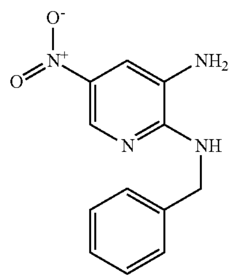 [SMILES: Nc1cc([N+](=O)[O-])cnc1NCc1ccccc1] | M + H = 245 | LCMS FA-2 |
| E-4.13 | 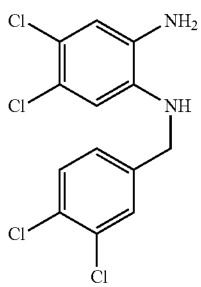 [SMILES: Nc1cc(Cl)c(Cl)cc1NCc1ccc(Cl)c(Cl)c1] | M + H = 335; tRet. = 1.12 | VAB |
| E-4.14 | 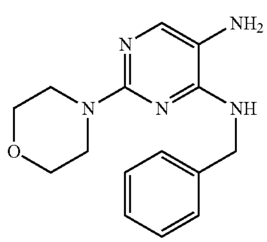 [SMILES: Nc1cnc(N2CCOCC2)nc1NCc1ccccc1] | M + H = 286; tRet. = 0.76 | VAB |
| E-4.15 | 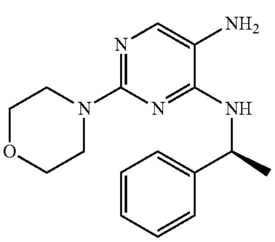 [SMILES: C[C@H](Nc1nc(N2CCOCC2)ncc1N)c1ccccc1] | M + H = 300; tRet. = 0.81 | VAB |

Biological Methods

BRD4-H4 Tetraacetylated Peptide Inhibition AlphaScreen

This assay is used to determine whether the compounds inhibit the interaction between the first (BRD4-BD1) or the second (BRD4-BD2) bromodomain of BRD4 and the tetraacetylated histone H4 peptide.

Compounds are diluted in serial dilution 1:5 in assay buffer from 10 mM stock in DMSO (100 μM start concentration) in white OptiPlate-384 (PerkinElmer). A mix consisting of 15 nM GST-BRD4-BD1 protein (aa 44-168) or 150 nM GST-BRD4-BD2 (aa 333-460) and 15 nM biotinylated Acetyl-Histone H4 (LysS, 8, 12, 16) peptide is prepared in assay buffer (50 mM HEPES pH=7.4; 25 mM NaCl; 0.05% Tween 20; 0.1% bovine serum albumin (BSA); 10 mM dithiothreitol (DTT)). 6 μl of the mix is added to the compound dilutions. Subsequently, 6 μl of premixed AlphaLISA Glutathione Acceptor Beads and AlphaScreen Streptavidin Donor Beads from PerkinElmer (in assay buffer at a concentration of 10 μg/ml each) are added and the samples are incubated for 30 min at RT in the dark (shaking 300 rpm). Afterwards, the signal is measured in a PerkinElmer Envision HTS Multilabel Reader using the AlphaScreen protocol from PerkinElmer.

Each plate contains negative controls where biotinylated Acetyl-Histone H4 peptide and GST-BRD4-BD1 or GST-BRD4-BD2 are left out and replaced by assay buffer. Negative control values are entered as low basis value when using the software GraphPad Prism for calculations. Furthermore, a positive control (probe molecule JQ1+ with protein/peptide mix) is pipetted. Determination of $IC_{50}$ values are carried out using GraphPad Prism 3.03 software (or updates thereof).

Table summarizing the $IC_{50}$ of the compounds of the invention exemplified above

| Ex # | BRD4-BD1 $IC_{50}$ [nM] | Ex # | BRD4-BD1 $IC_{50}$ [nM] |
|---|---|---|---|
| I-1 | 12 | I-2 | 1535 |
| I-3 | 109 | I-4 | 515 |
| I-5 | 547 | I-6 | 19 |
| I-7 | 95 | I-8 | 609 |
| I-9 | 58 | I-10 | 49 |
| I-11 | 12 | I-12 | 18 |
| I-13 | 68 | I-14 | 36 |
| I-15 | 1385 | I-16 | 192 |
| I-17 | 218 | I-18 | 1114 |
| I-19 | 298 | I-20 | 121 |
| I-21 | 201 | I-22 | 44 |
| I-23 | 190 | I-24 | 128 |
| I-25 | 72 | I-26 | 96 |
| I-27 | 103 | I-28 | 174 |
| I-29 | 180 | I-30 | 63 |
| I-31 | 75 | I-32 | 268 |
| I-33 | 47 | I-34 | 49 |
| I-35 | 23 | I-36 | 65 |
| I-37 | 103 | I-38 | 32 |
| I-39 | 142 | | |
| II-1 | 19 | II-2 | 54 |
| II-3 | 18 | II-4 | 55 |
| II-5 | 12 | II-6 | 163 |
| II-7 | 175 | II-8 | 148 |
| II-9 | 30 | II-10 | 45 |
| II-11 | 102 | II-12 | 49 |
| II-13 | 102 | II-14 | 63 |
| II-15 | 42 | II-16 | 68 |
| II-17 | 160 | II-18 | 233 |
| II-19 | 27 | II-20 | 33 |
| II-21 | 42 | II-22 | 34 |
| II-23 | 33 | II-24 | 38 |
| II-25 | 8 | II-26 | 16 |
| II-27 | 166 | II-28 | 128 |
| II-29 | 130 | II-30 | 62 |
| II-31 | 40 | II-32 | 105 |
| II-33 | 169 | II-34 | 120 |
| II-35 | 211 | II-36 | 650 |
| II-37 | 172 | II-38 | 205 |
| II-39 | 211 | II-40 | 295 |
| II-41 | 1201 | II-42 | 35 |
| II-43 | 50 | II-44 | 188 |
| II-45 | 95 | | |
| III-1 | 697 | III-2 | 1777 |
| III-3 | 45 | III-4 | 118 |
| III-5 | 117 | III-6 | 108 |
| III-7 | 220 | III-8 | 200 |
| III-9 | 217 | | |
| IV-1 | 313 | IV-2 | 218 |
| IV-3 | 188 | IV-4 | 60 |

-continued

| Ex # | BRD4-BD1 IC$_{50}$ [nM] | Ex # | BRD4-BD1 IC$_{50}$ [nM] |
|---|---|---|---|
| IV-5 | 32 | IV-6 | 23 |
| IV-7 | 16 | IV-8 | 70 |
| IV-9 | 119 | IV-10 | 109 |
| IV-11 | 12 | IV-12 | 38 |
| IV-13 | 4810 | IV-14 | 50 |
| IV-15 | 17 | | |
| V-1 | 145 | V-2 | 1350 |
| V-3 | 73 | V-4 | 133 |
| VI-1 | 136 | | |

On the basis of their biological properties the compounds of general formula (1) according to the invention, their tautomers, racemates, enantiomers, diastereomers, mixtures thereof and the salts of all the above-mentioned forms are suitable for treating diseases characterised by virus infection, inflammatory diseases and abnormal cell proliferation, such as cancer.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma (MM)), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (A ML); chronic leukaemias such as chronic lymphatic leukaemia (CLL), chronic myeloid leukaemia (C ML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

Preferred cancers, which may be treated with compounds according to the invention, are hematopoietic malignancies (including but not limited to A ML, MM), as well as solid tumors including but not limited to lung, liver, colon, brain, thyroid, pancreas, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxycamptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992 (afatinib), BIBF 1120 (Vargatef™), bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, mlN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, Volasertib (or other polo-like kinae inhibitors), xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples Of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (I)

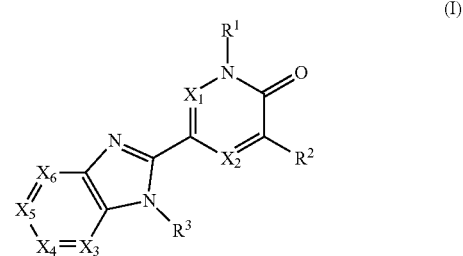

wherein, $R^1$ is —$C_{1-3}$alkyl and $R^2$ is selected from —$C_{1-3}$alkyl, —$C_{1-3}$haloalkyl, —$NH_2$, —NH—$C_{1-3}$alkyl, and halogen;

$R^3$ is —$C_{1-4}$alkyl substituted with one or more groups independently selected from halogen, —$C_{1-2}$haloalkyl, —O—$C_{1-3}$alkyl, —O—$C_{1-3}$haloalkyl, 4-7 membered heterocycloalkyl, —$C_{3-7}$ cycloalkyl, phenyl and 5-6 membered heteroaryl, wherein the phenyl and the 5-6 membered heteroaryl groups can be optionally substituted with one or more groups independently selected from halogen and —$C_{1-2}$alkyl;

$X_1$ is —CH= or —N=

$X_2$ is —$CR^7$= or —N=, wherein $X_1$ is —CH= and $X_2$ is —N=, or $X_1$ is —N= and $X_2$ is —CH=, or $X_1$ is —CH= and $X_2$ is =$CR^7$=

$X_3$ is —$CR^8$= or —N=;

$X_4$ is —$CR^4$= or —N=;

$X_5$ is —$CR^5$= or —N=;

$X_6$ is —CH= or —N=;

with the proviso that none or only one or two among $X_3$, $X_4$, $X_5$ and $X_6$ are —N=;

$R^4$ is selected from —H, halogen, —CN, —$NH_2$, —O—$R^6$, —N($C_{1-3}$alkyl)$_2$, —C(O)N($C_{1-3}$alkyl)$_2$ and —$C_{1-5}$alkyl, wherein the —$C_{1-5}$alkyl group can be optionally and independently substituted with one or more groups independently selected from halogen or —CN, or $R^4$ is selected from 5-6 membered heteroaryl and 4-7 memebered heterocycloalkyl, wherein the heteroaryl groups can be optionally and independently substituted with one or more groups independently selected from —$C_{1-3}$alkyl, and the heterocycloalkyl group can be optionally and independently substituted with one or more groups independently selected from —$C_{1-3}$alkyl or =O, or $R^4$ is a —$C_{3-6}$cycloalkyl wherein the cycloalkyl group can be optionally and independently substituted with one or more groups independently selected from $C_{1-3}$alkyl, —$C_{1-3}$haloalkyl and halogen;

$R^5$ is selected from —H, halogen, —$NH_2$, —$C_{1-3}$alkyl, —$SO_2$N($C_{1-3}$alkyl)$_2$ and 5-6 membered heterocycloalkyl, which heterocycloalkyl can be optionally substituted with one or more groups independently selected from =O, —$C_{1-3}$alkyl, and —$C_{1-5}$haloalkyl;

$R^6$ is selected from 4-7 membered heterocycloalkyl, —$C_{3-7}$ cycloalkyl and —$C_{1-5}$alkyl, wherein the —$C_{1-5}$alkyl group can be optionally substituted with —$C_{3-7}$ cycloalkyl, $R^7$ is selected from —H, —$C_{1-5}$alkyl and —O—$C_{1-5}$alkyl;

$R^8$ is —H or —$C_{1-3}$ alkyl;

or a pharmaceutically acceptable salt thereof.

2. A compound according to claim 1, of a formula selected from the group consisting of.

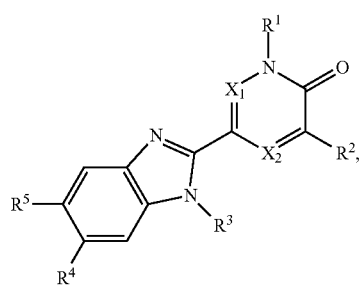
(Ia)

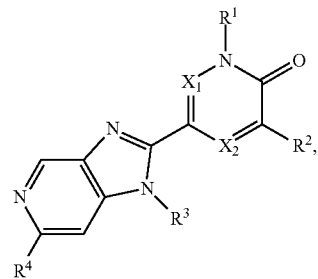
(Ib)

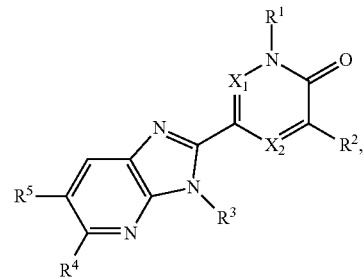
(Ic)

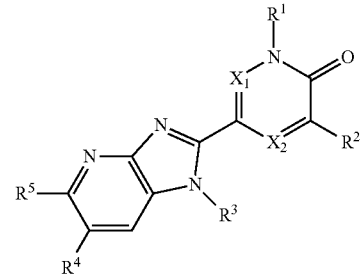
(Id)

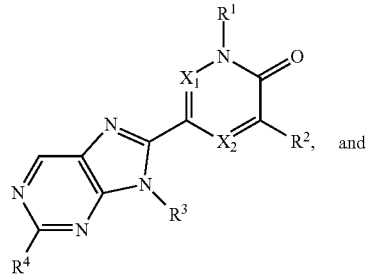
(Ie)

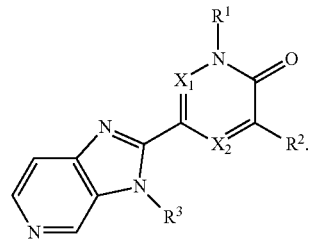
(If)

3. A compound according to claim 2, of a formula selected from the group consisting of.
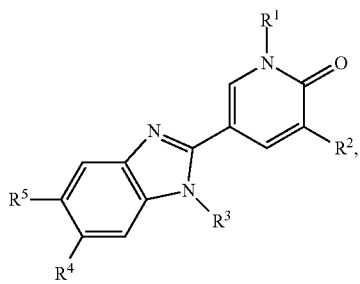
(Ia1)
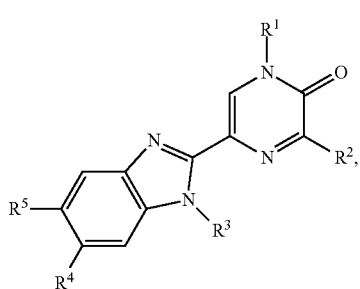
(Ia2)
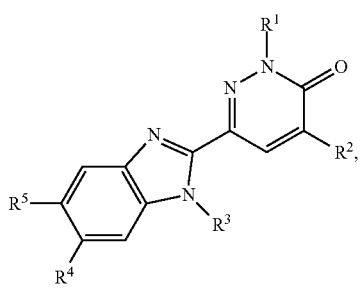
(Ia3)
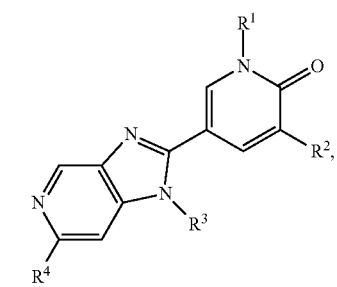
(Ib1)
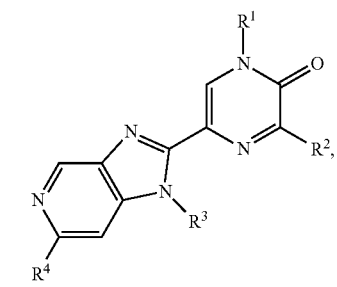
(Ib2)
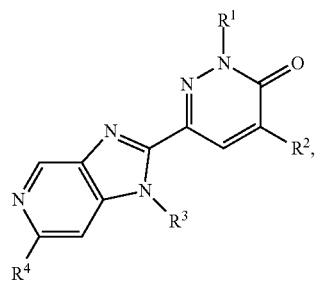
(Ib3)
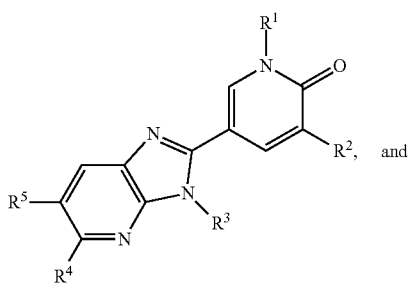
(Ic1) and
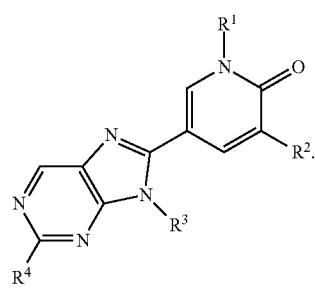
(Ie1)
4. A compound according to claim 1, of the formula.
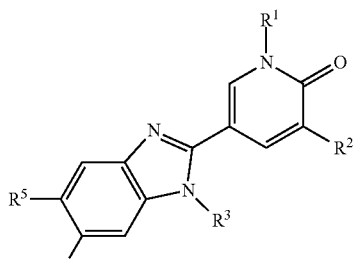
(Ia1)
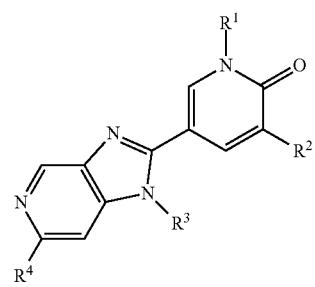
(Ib1)

-continued

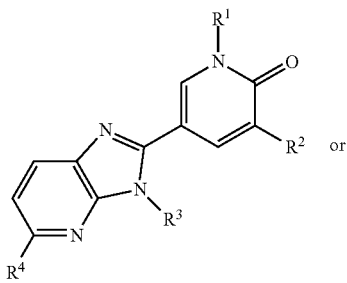

(Ic1)

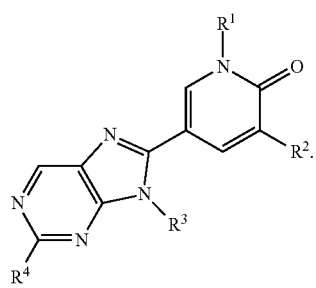

(Ie1)

5. A compound according to claim 1, wherein R¹ is —CH₃.
6. A compound according to claim 1, wherein R² is —NH₂, —NH—C₁₋₃ alkyl or —C₁₋₃ alkyl.
7. A compound according to claim 6, wherein R² is —NH₂, —NHCH₃ or —CH₃.
8. A compound according to claim 7, wherein R² is —CH₃.
9. A compound according to claim 1, wherein wherein R³ is —CH(CH₃)—CH₂—O—CH₃, —CH(CH₃)—CH₂-cyclopropyl, —CH₂-phenyl, —CH₂-pyridyl, —CH(CH₃)phenyl, or —CH(CH₃)-pyridyl, wherein the phenyl and pyridyl groups are optionally and independently substituted with —Cl or with one or two —F.
10. A compound according to claim 9, wherein R³ is —CH₂-phenyl, —CH₂-pyridyl, —CH(CH₃)phenyl or —CH(CH₃)-pyridyl.
11. A compound according to claim 10, wherein R³ is —CH₂-phenyl or —CH(CH₃)phenyl.
12. A compound according to claim 1, wherein R⁴ is —H, halogen, —CN, —NH₂, —C₁₋₅alkyl, —N(C₁₋₃alkyl)₂, —C(O)N(C₁₋₃alkyl)₂, —O—C₁₋₅alkyl, —O—CH₂ -cyclopropyl, —O—(6 membered heterocycloalkyl), —O—cyclopropyl, 5-6 membered heteroaryl or 4-7 memebered heterocycloalkyl, wherein the heterocycloalkyl is optionally substituted with one or more groups independently selected from —C₁₋₃alkyl.
13. A compound according to claim 12, wherein R⁴ is selected from —H, —F, —Cl, —CN, isopropyl, —NH₂, —N(CH₃)₂, —C(O)N(CH₃)₂, —O—CH₃, —O—(CH₂)₂CH₃, —O-piperidine, —O-cyclopropyl, —O—CH₂-cyclopropyl, imidazole, tetrahydropyran, piperazine substituted with —CH₃, and morpholine optionally substituted with —CH₃.
14. A compound according to claims 12, wherein R⁴ is selected from —C₁₋₅alkyl or 4-7 memebered heterocycloalkyl, which heterocycloalkyl can be optionally substituted with one or more groups independently selected from —C₁₋₃alkyl.
15. A compound according to claim 14, wherein R⁴ is selected from isopropyl, tetrahydropyran, piperazine substituted with —CH₃ and morpholine optionally substituted with —CH₃.

16. A compound according to claim 1, wherein R⁵ is selected from —H, —Cl, —NH₂, —SO₂N(CH₃), piperazine optionally substituted with —CH₃, tetrahydropyran and

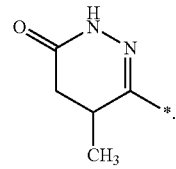

17. A compound according to claim 1 selected from the group consisting of

| EX# | Structure |
|---|---|
| I-1 | 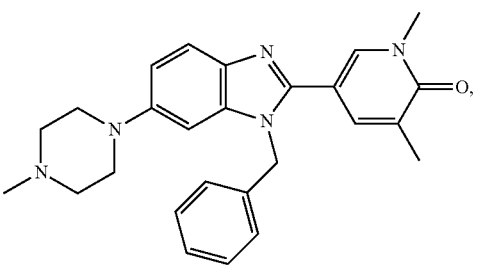 |
| I-6 | 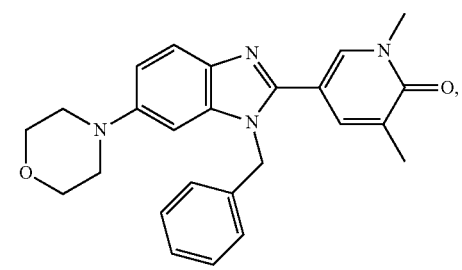 [SMILES: Cc1cc(-c2nc3ccc(N4CCOCC4)cc3n2Cc2ccccc2)cn(C)c1=O] |
| I-9 | 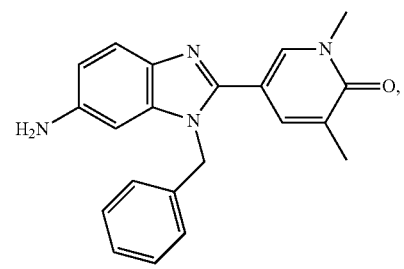 |
| I-10 | 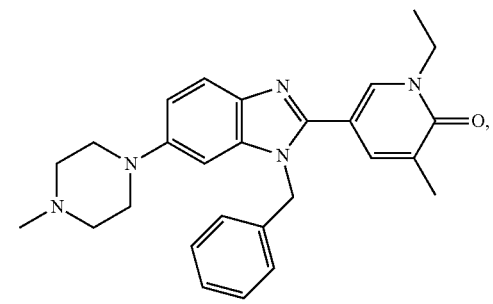 [SMILES: CCn1cc(-c2nc3ccc(N4CCN(C)CC4)cc3n2Cc2ccccc2)cc(C)c1=O] |

| EX# | Structure |
|---|---|
| I-11 | 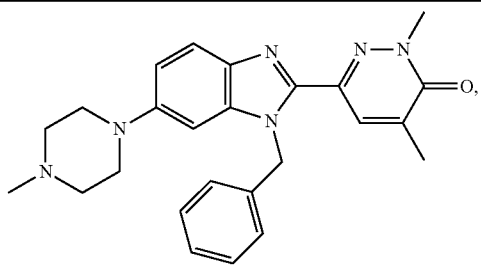 |
| I-12 | 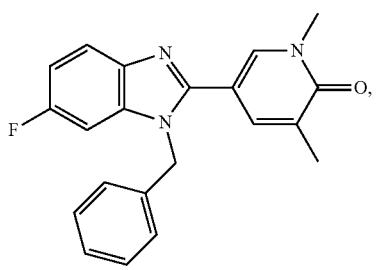 [SMILES: Cc1cc(-c2nc3ccc(F)cc3n2Cc2ccccc2)cn(C)c1=O] |
| I-13 | 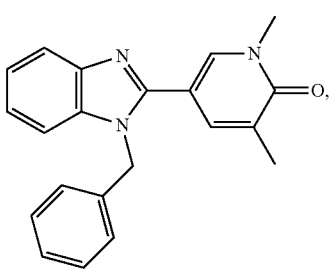 [SMILES: Cc1nc(-c2nc3ccccc3n2Cc2ccccc2)cn(C)c1=O] |
| I-14 | 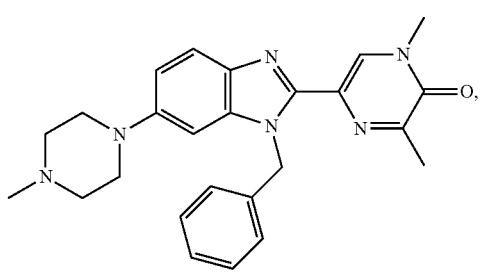 |
| I-21 | 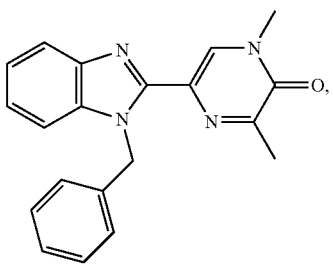 |
| I-22 | 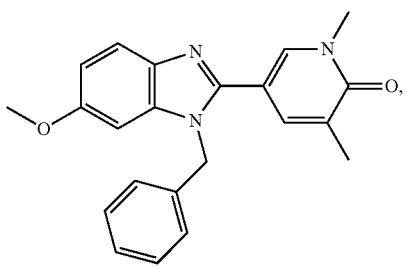 [SMILES: COc1ccc2nc(-c3cc(C)c(=O)n(C)c3)n(Cc3ccccc3)c2c1] |
| I-23 | 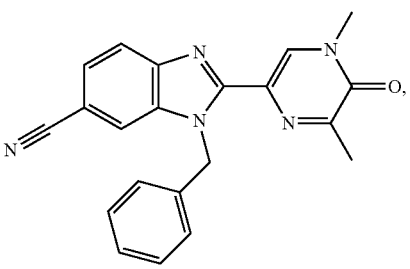 [SMILES: Cc1nc(-c2nc3ccc(C#N)cc3n2Cc2ccccc2)cn(C)c1=O] |
| I-24 | 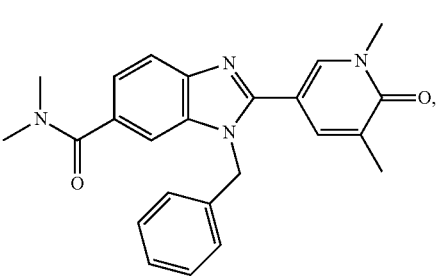 [SMILES: Cc1cc(-c2nc3ccc(C(=O)N(C)C)cc3n2Cc2ccccc2)cn(C)c1=O] |
| I-25 | 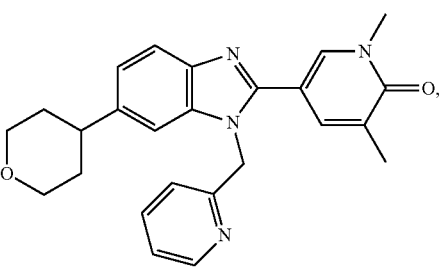 [SMILES: Cc1cc(-c2nc3ccc(C4CCOCC4)cc3n2Cc2ccccn2)cn(C)c1=O] |
| I-26 | 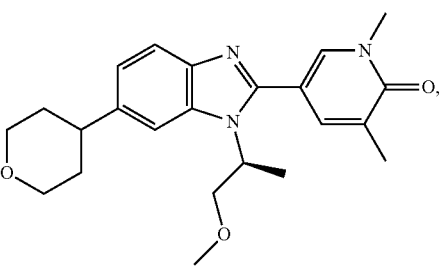 [SMILES: COC[C@H](C)n1c(-c2cc(C)c(=O)n(C)c2)nc2ccc(C3CCOCC3)cc21] |

| EX# | Structure |
|---|---|
| I-27 | 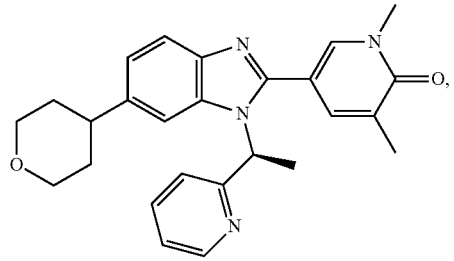 |
| I-28 | 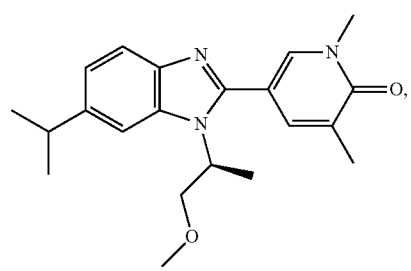 [SMILES: COC[C@H](C)n1c(-c2cc(C)c(=O)n(C)c2)nc2ccc(C(C)C)cc21] |
| I-29 | 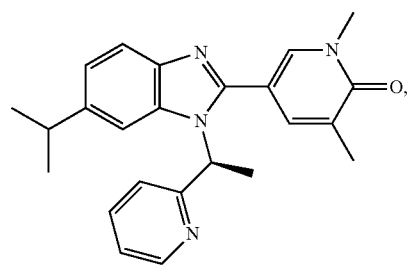 [SMILES: Cc1cc(-c2nc3ccc(C(C)C)cc3n2[C@@H](C)c2ccccn2)cn(C)c1=O] |
| I-30 | 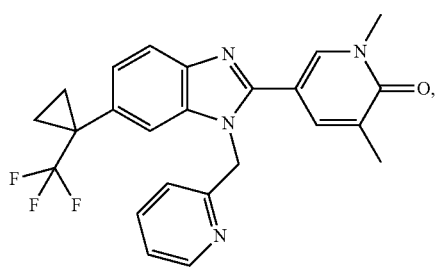 [SMILES: Cc1cc(-c2nc3ccc(C4(C(F)(F)F)CC4)cc3n2Cc2ccccn2)cn(C)c1=O] |
| I-31 | 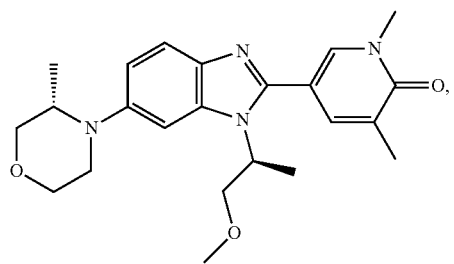 [SMILES: COC[C@H](C)n1c(-c2cc(C)c(=O)n(C)c2)nc2ccc(N3CCOC[C@@H]3C)cc21] |
| EX# | Structure |
|---|---|
| I-32 | 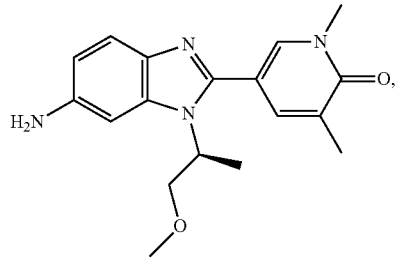 [SMILES: COC[C@H](C)n1c(-c2cc(C)c(=O)n(C)c2)nc2ccc(N)cc21] |
| I-33 | 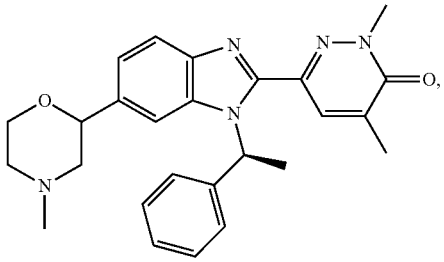 |
| I-34 | 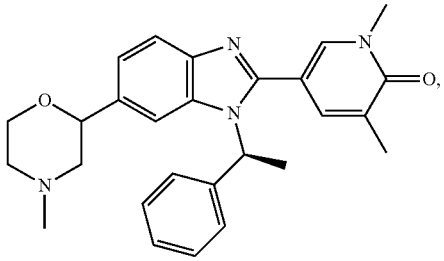 [SMILES: Cc1cc(-c2nc3ccc(C4CN(C)CCO4)cc3n2[C@@H](C)c2ccccc2)cn(C)c1=O] |
| I-35 | 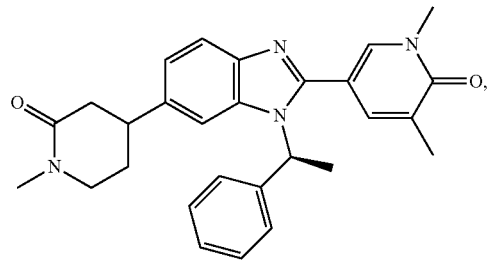 [SMILES: Cc1cc(-c2nc3ccc(C4CCN(C)C(=O)C4)cc3n2[C@@H](C)c2ccccc2)cn(C)c1=O] |
| I-36 | 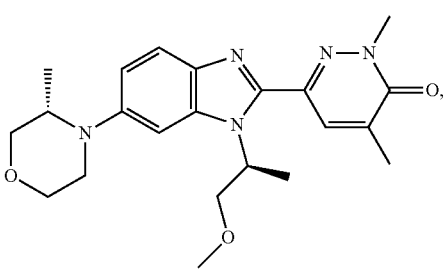 |

| EX# | Structure |
|---|---|
| I-37 | 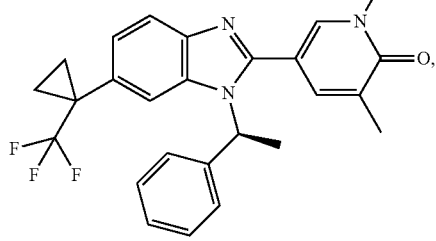 |
| I-38 | 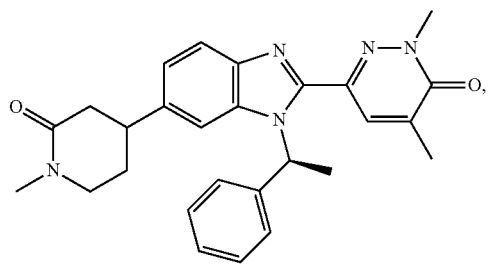 [SMILES: Cc1cc(-c2nc3ccc(C4CCN(C)C(=O)C4)cc3n2[C@@H](C)c2ccccc2)nn(C)c1=O] |
| I-39 | 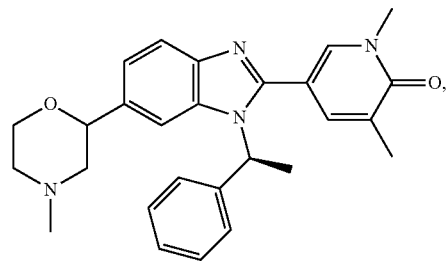 [SMILES: Cc1cc(-c2nc3ccc(C4CN(C)CCO4)cc3n2[C@@H](C)c2ccccc2)cn(C)c1=O] |
| II-1 | 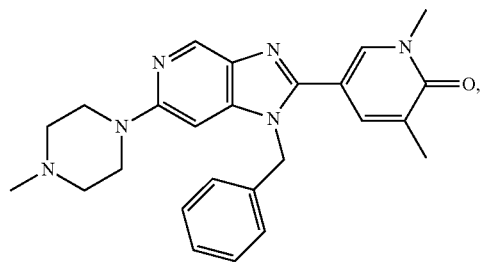 [SMILES: Cc1cc(-c2nc3cnc(N4CCN(C)CC4)cc3n2Cc2ccccc2)cn(C)c1=O] |
| II-2 | 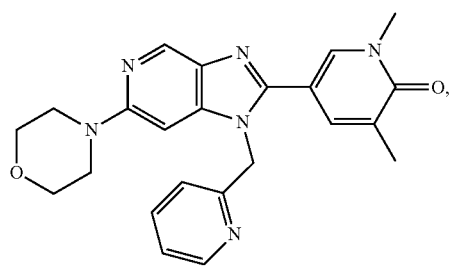 |
| EX# | Structure |
|---|---|
| II-3 | 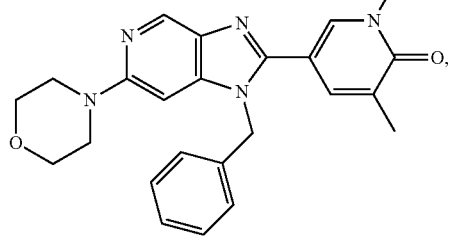 |
| II-4 | 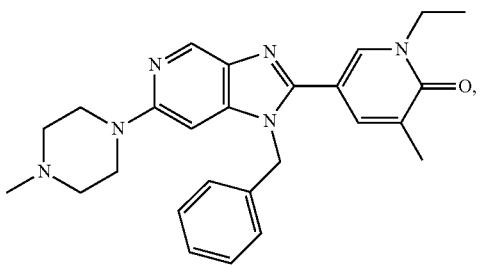 [SMILES: CCn1cc(-c2nc3cnc(N4CCN(C)CC4)cc3n2Cc2ccccc2)cc(C)c1=O] |
| II-5 | 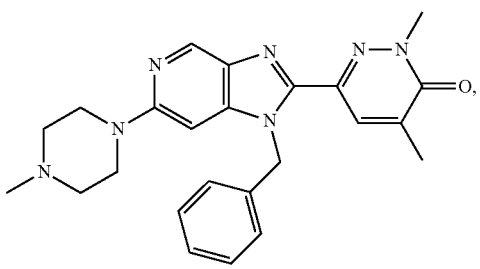 [SMILES: Cc1cc(-c2nc3cnc(N4CCN(C)CC4)cc3n2Cc2ccccc2)nn(C)c1=O] |
| II-6 | 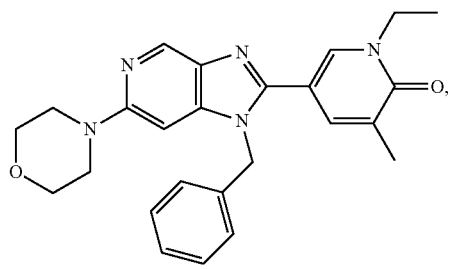 [SMILES: CCn1cc(-c2nc3cnc(N4CCOCC4)cc3n2Cc2ccccc2)cc(C)c1=O] |
| II-7 | 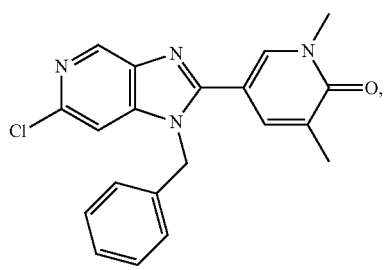 [SMILES: Cc1cc(-c2nc3cnc(Cl)cc3n2Cc2ccccc2)cn(C)c1=O] |

| EX# | Structure |
|---|---|
| II-8 | 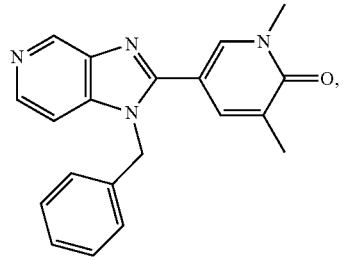 [SMILES: Cc1cc(-c2nc3cnccc3n2Cc2ccccc2)cn(C)c1=O] |
| II-9 | 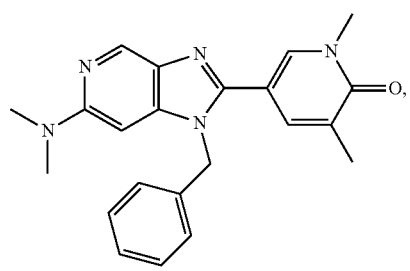 [SMILES: Cc1cc(-c2nc3cnc(N(C)C)cc3n2Cc2ccccc2)cn(C)c1=O] |
| II-10 | 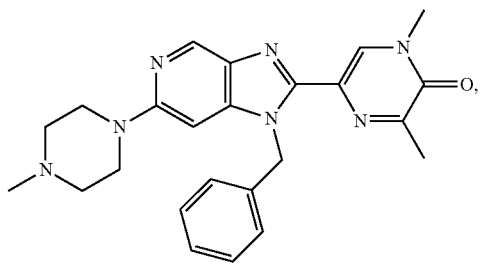 [SMILES: Cc1nc(-c2nc3cnc(N4CCN(C)CC4)cc3n2Cc2ccccc2)cn(C)c1=O] |
| II-11 | 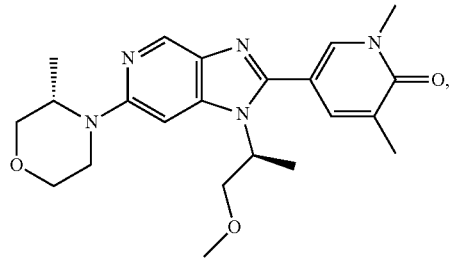 [SMILES: COC[C@H](C)n1c(-c2cc(C)c(=O)n(C)c2)nc2cnc(N3CCOC[C@@H]3C)cc21] |
| II-12 | 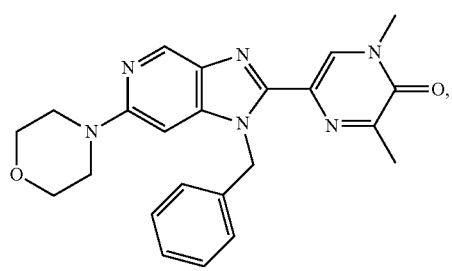 |
| II-13 | 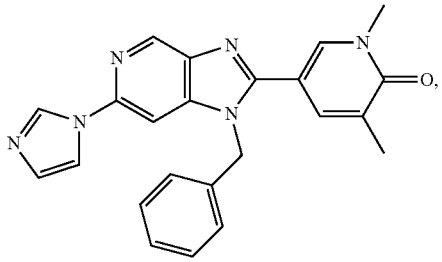 [SMILES: Cc1cc(-c2nc3cnc(-n4ccnc4)cc3n2Cc2ccccc2)cn(C)c1=O] |
| II-14 | 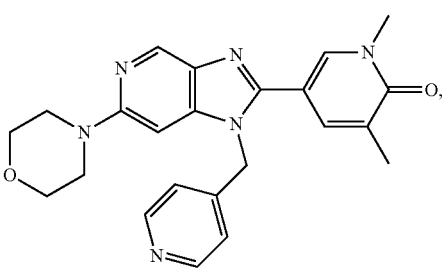 [SMILES: Cc1cc(-c2nc3cnc(N4CCOCC4)cc3n2Cc2ccncc2)cn(C)c1=O] |
| II-15 | 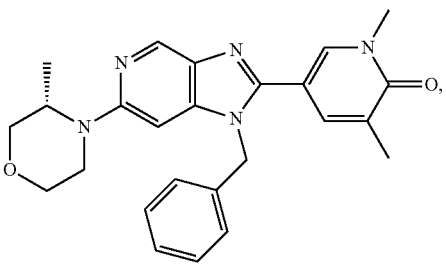 [SMILES: Cc1cc(-c2nc3cnc(N4CCOC[C@@H]4C)cc3n2Cc2ccccc2)cn(C)c1=O] |
| II-16 | 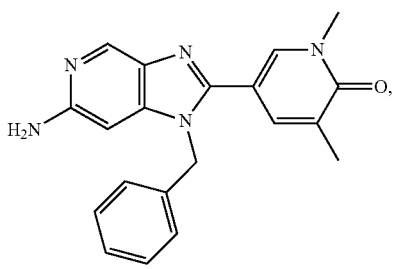 |
| II-17 | 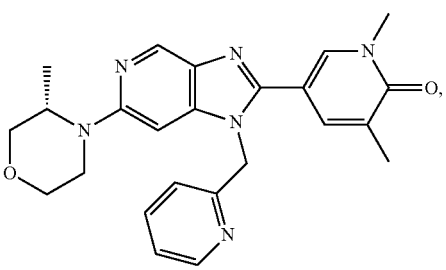 [SMILES: Cc1cc(-c2nc3cnc(N4CCOC[C@@H]4C)cc3n2Cc2ccccn2)cn(C)c1=O] |

| EX# | Structure |
|---|---|
| II-18 | (structure) |
| II-19 | (structure) |
| II-20 | (structure) |
| II-21 | (structure) |
| II-22 | (structure) |
| II-23 | (structure) |
| II-24 | (structure) |
| II-25 | (structure) |
| II-26 | (structure) |
| II-27 | (structure) |

| EX# | Structure |
|---|---|
| II-28 | 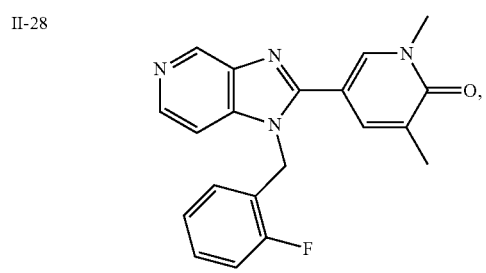 |
| II-29 | 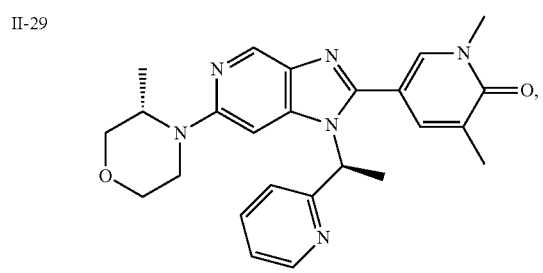 |
| II-30 | 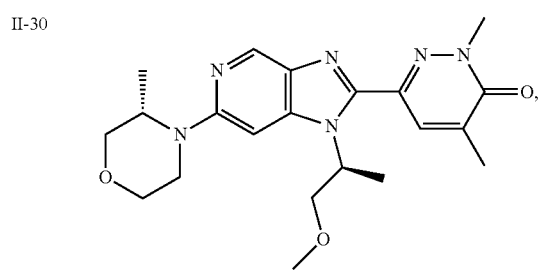 |
| II-31 | 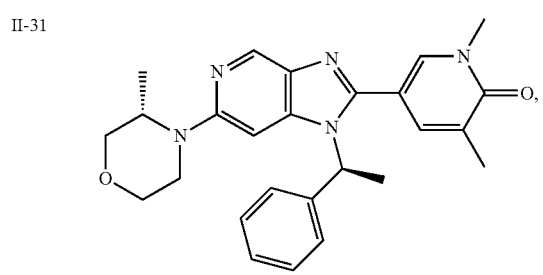 |
| II-32 | 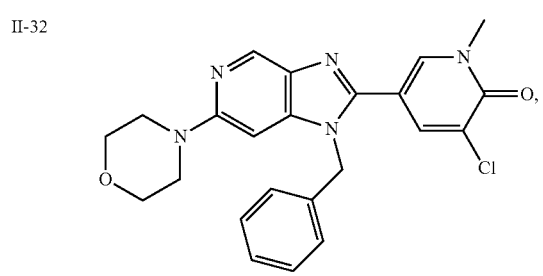 |
| II-33 | 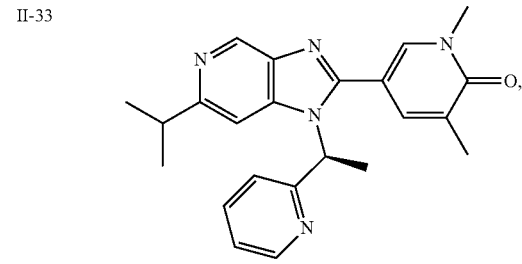 |
| II-34 | 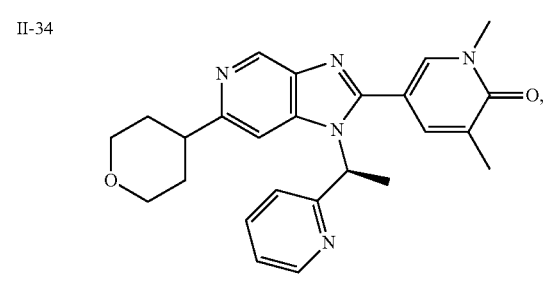 |
| II-35 | 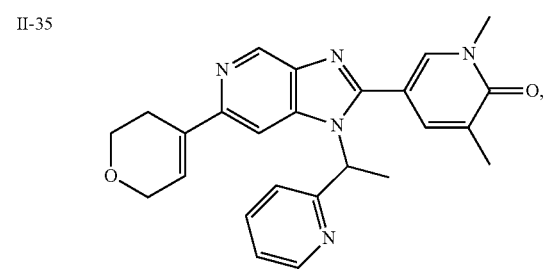 |
| II-36 | 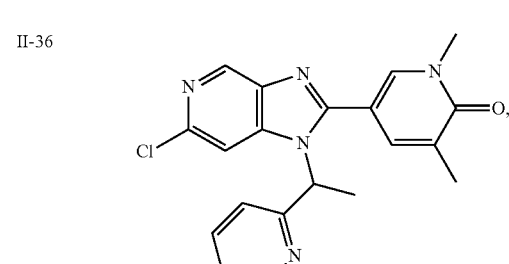 |
| II-37 | 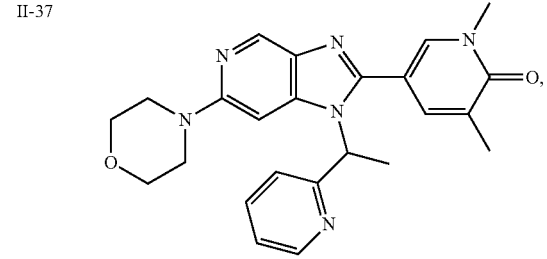 |

-continued

| EX# | Structure |
|---|---|
| II-38 | 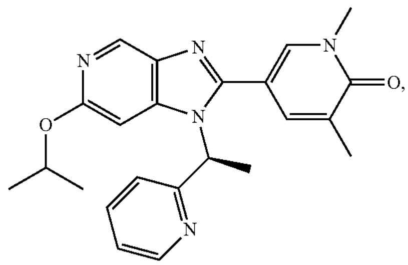 [SMILES: Cc1cc(-c2nc3cnc(OC(C)C)cc3n2[C@@H](C)c2ccccn2)cn(C)c1=O] |
| II-39 | 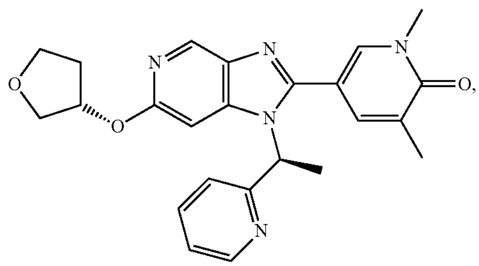 |
| II-40 | 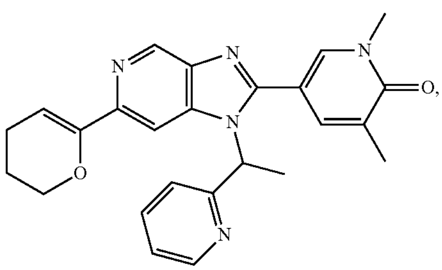 [SMILES: Cc1cc(-c2nc3cnc(C4=CCCCO4)cc3n2C(C)c2ccccn2)cn(C)c1=O] |
| II-41 | 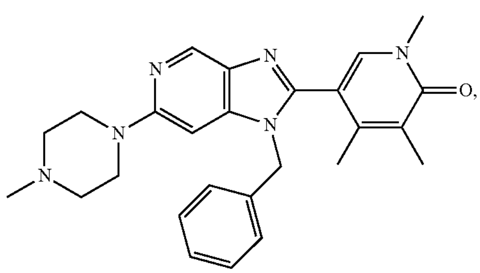 [SMILES: Cc1c(-c2nc3cnc(N4CCN(C)CC4)cc3n2Cc2ccccc2)cn(C)c(=O)c1C] |
| II-42 | 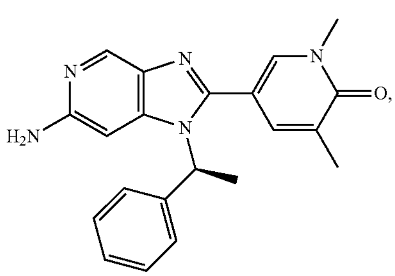 [SMILES: Cc1cc(-c2nc3cnc(N)cc3n2[C@@H](C)c2ccccc2)cn(C)c1=O] |

-continued

| EX# | Structure |
|---|---|
| II-43 | 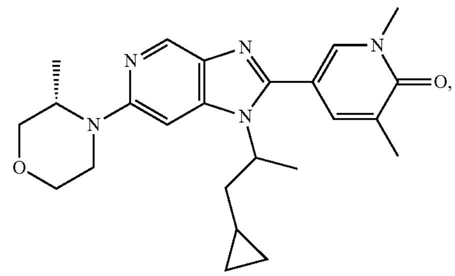 [SMILES: Cc1cc(-c2nc3cnc(N4CCOC[C@@H]4C)cc3n2C(C)CC2CC2)cn(C)c1=O] |
| II-45 | 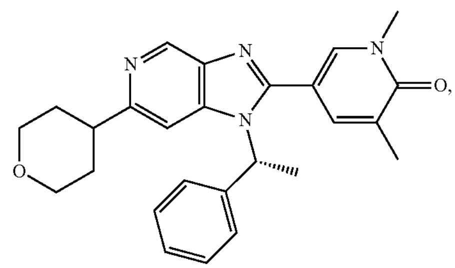 |
| III-3 | 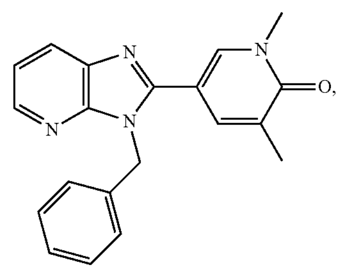 [SMILES: Cc1cc(-c2nc3cccnc3n2Cc2ccccc2)cn(C)c1=O] |
| III-4 | 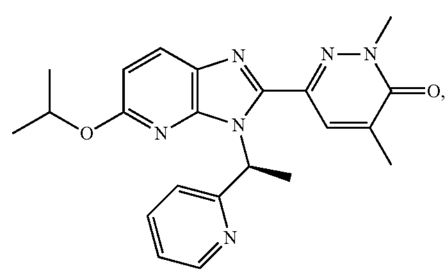 [SMILES: Cc1cc(-c2nc3ccc(OC(C)C)nc3n2[C@@H](C)c2ccccn2)nn(C)c1=O] |
| III-5 | 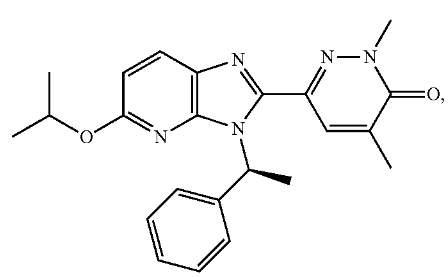 [SMILES: Cc1cc(-c2nc3ccc(OC(C)C)nc3n2[C@@H](C)c2ccccc2)nn(C)c1=O] |

| EX# | Structure |
|---|---|
| III-6 | 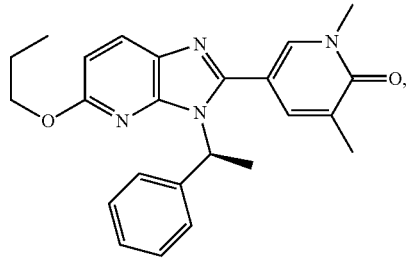 [SMILES: CCCOc1ccc2nc(-c3cc(C)c(=O)n(C)c3)n([C@@H](C)c3ccccc3)c2n1] |
| III-7 | 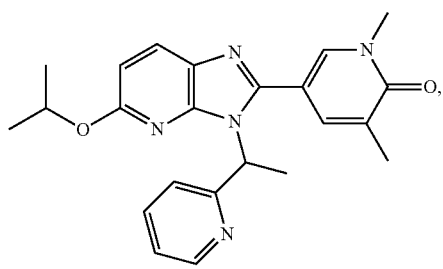 [SMILES: Cc1cc(-c2nc3ccc(OC(C)C)nc3n2C(C)c2ccccn2)cn(C)c1=O] |
| III-8 | 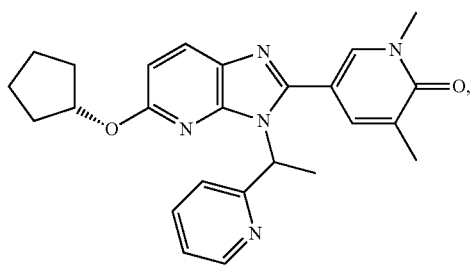 |
| III-9 | 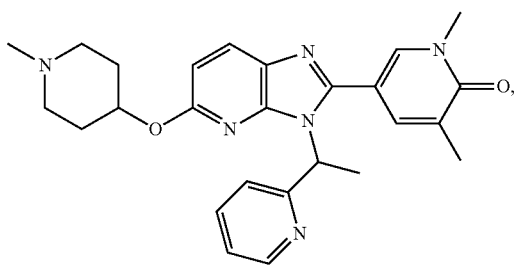 [SMILES: Cc1cc(-c2nc3ccc(OC4CCN(C)CC4)nc3n2C(C)c2ccccn2)cn(C)c1=O] |
| IV-1 | 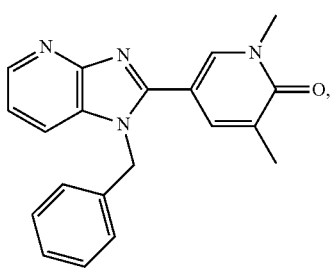 [SMILES: Cc1cc(-c2nc3ncccc3n2Cc2ccccc2)cn(C)c1=O] |
| EX# | Structure |
|---|---|
| IV-3 | 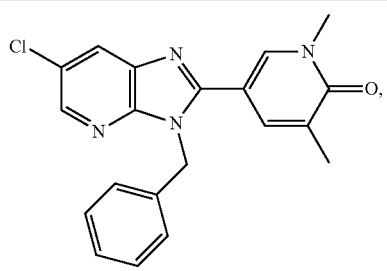 [SMILES: Cc1cc(-c2nc3cc(Cl)cnc3n2Cc2ccccc2)cn(C)c1=O] |
| IV-4 | 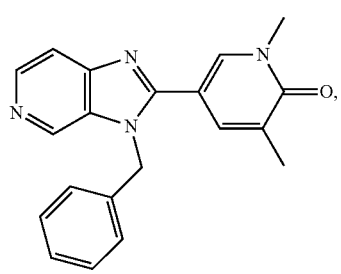 [SMILES: Cc1cc(-c2nc3ccncc3n2Cc2ccccc2)cn(C)c1=O] |
| IV-5 | 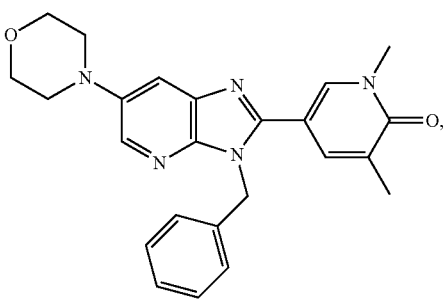 [SMILES: Cc1cc(-c2nc3cc(N4CCOCC4)cnc3n2Cc2ccccc2)cn(C)c1=O] |
| IV-6 | 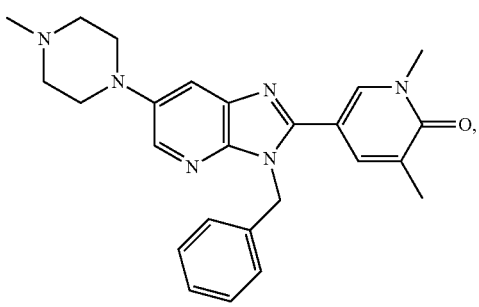 [SMILES: Cc1cc(-c2nc3cc(N4CCN(C)CC4)cnc3n2Cc2ccccc2)cn(C)c1=O] |
| IV-7 | 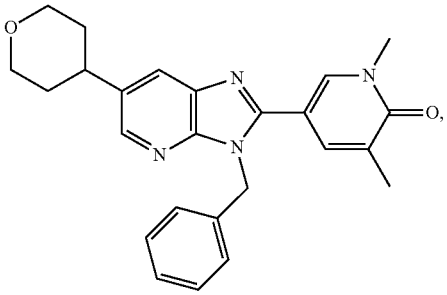 [SMILES: Cc1cc(-c2nc3cc(C4CCOCC4)cnc3n2Cc2ccccc2)cn(C)c1=O] |

175
-continued
| EX# | Structure |
|---|---|
| IV-8 | 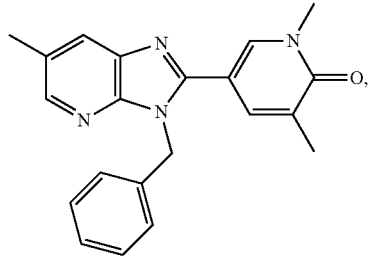 [SMILES: Cc1cnc2c(c1)nc(-c1cc(C)c(=O)n(C)c1)n2Cc1ccccc1] |
| IV-9 | 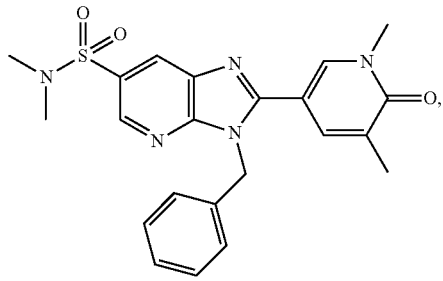 [SMILES: Cc1cc(-c2nc3cc(S(=O)(=O)N(C)C)cnc3n2Cc2ccccc2)cn(C)c1=O] |
| IV-10 | 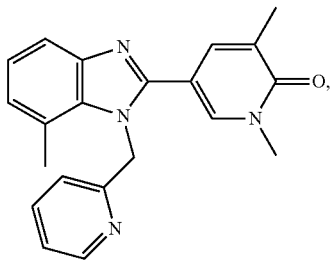 [SMILES: Cc1cc(-c2nc3cccc(C)c3n2Cc2ccccn2)cn(C)c1=O] |
| IV-11 | 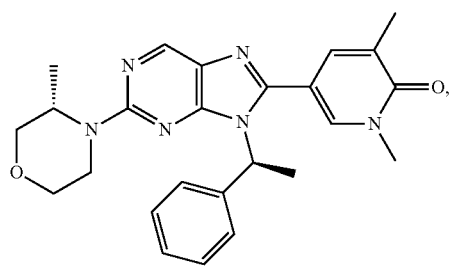 [SMILES: Cc1cc(-c2nc3cnc(N4CCOC[C@@H]4C)nc3n2[C@@H](C)c2ccccc2)cn(C)c1=O] |
| IV-12 | 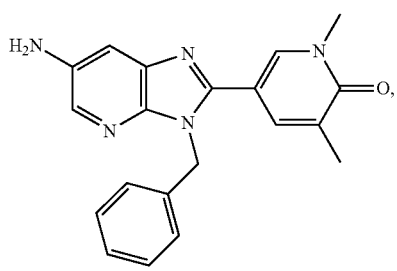 |
176
-continued
| EX# | Structure |
|---|---|
| IV-13 | 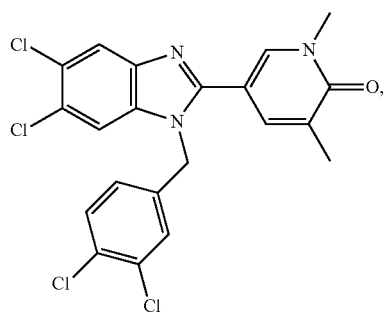 [SMILES: Cc1cc(-c2nc3cc(Cl)c(Cl)cc3n2Cc2ccc(Cl)c(Cl)c2)cn(C)c1=O] |
| IV-14 | 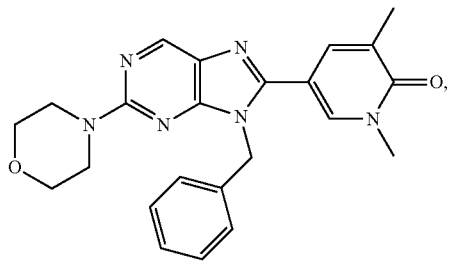 [SMILES: Cc1cc(-c2nc3cnc(N4CCOCC4)nc3n2Cc2ccccc2)cn(C)c1=O] |
| IV-15 | 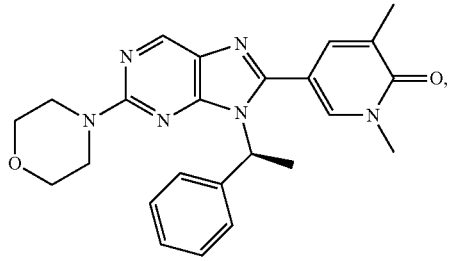 [SMILES: Cc1cc(-c2nc3cnc(N4CCOCC4)nc3n2[C@@H](C)c2ccccc2)cn(C)c1=O] |
| V-1 | 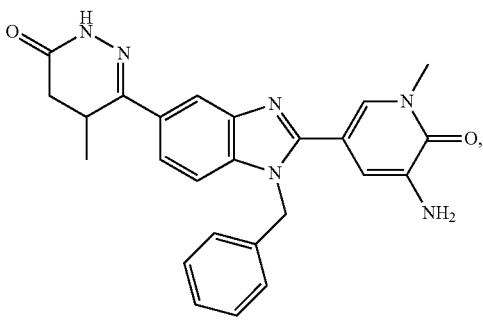 [SMILES: CC1CC(=O)NN=C1c1ccc2c(c1)nc(-c1cc(N)c(=O)n(C)c1)n2Cc1ccccc1] |
| V-2 | 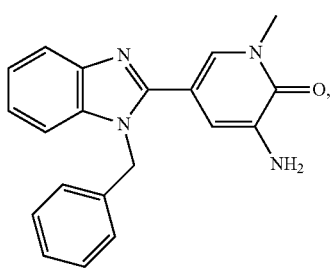 [SMILES: Cn1cc(-c2nc3ccccc3n2Cc2ccccc2)cc(N)c1=O] |

| EX# | Structure |
|---|---|
| V-3 | 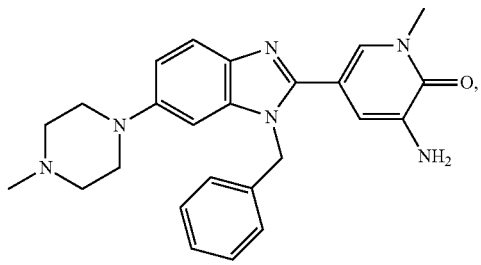 [SMILES: CN1CCN(c2ccc3nc(-c4cc(N)c(=O)n(C)c4)n(Cc4ccccc4)c3c2)CC1] |
| V-4 | 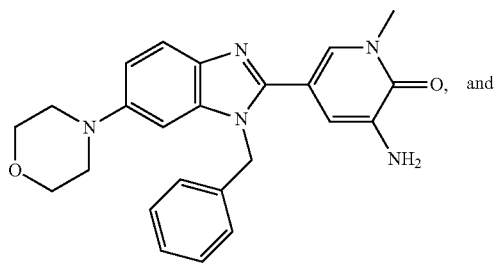 [SMILES: Cn1cc(-c2nc3ccc(N4CCOCC4)cc3n2Cc2ccccc2)cc(N)c1=O ; "and"] and |
| EX# | Structure |
|---|---|
| VI-1 | 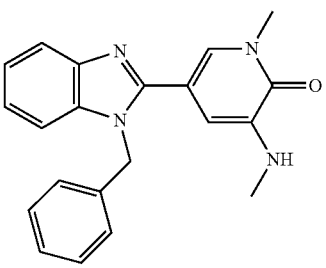 [SMILES: CNc1cc(-c2nc3ccccc3n2Cc2ccccc2)cn(C)c1=O] |
or a pharmaceutically acceptable salt thereof.
18. A pharmaceutical composition comprising a compound according to claim 1 and a pharmaceutically acceptable carrier.
* * * * *